United States Patent
Fujishita et al.

(10) Patent No.: US 6,506,787 B2
(45) Date of Patent: *Jan. 14, 2003

(54) INDOLE DERIVATIVES HAVING AN ANTIVIRAL ACTIVITY

(75) Inventors: Toshio Fujishita, Osaka (JP); Tomokazu Yoshinaga, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/929,486

(22) Filed: Aug. 15, 2001

(65) Prior Publication Data

US 2002/0019434 A1 Feb. 14, 2002

Related U.S. Application Data

(62) Division of application No. 09/622,543, filed as application No. PCT/JP99/01547 on Mar. 26, 1999, now Pat. No. 6,333,323.

(30) Foreign Application Priority Data

Mar. 26, 1998 (JP) .............................. 10-78203

(51) Int. Cl.$^7$ .................. A61K 31/32; C07D 209/12
(52) U.S. Cl. ...................... 514/419; 548/493
(58) Field of Search ................ 548/204, 253, 548/266.6, 312.1, 493; 514/233.5, 414, 419

(56) References Cited

U.S. PATENT DOCUMENTS 5,475,109 A 12/1995 Selnick et al. ............. 546/225
6,333,323 B1 * 12/2001 Fujishita et al. ......... 514/233.5

FOREIGN PATENT DOCUMENTS

| JP | 5-208910 | 8/1993 |
| WO | 99/62513 | 12/1999 |
| WO | 99/62520 | 12/1999 |
| WO | 99/62897 | 12/1999 |
| WO | 01/00578 | 1/2001 |

OTHER PUBLICATIONS

Khim. Geterotsikl. Soedin., vol. 11, pp. 1519–1522 (1973).

* cited by examiner

Primary Examiner—T. A. Solola
Assistant Examiner—Ebenezer Sackey
(74) Attorney, Agent, or Firm—Wenderoth, Lind & Ponack, L.L.P.

(57) ABSTRACT

A compound of the formula:

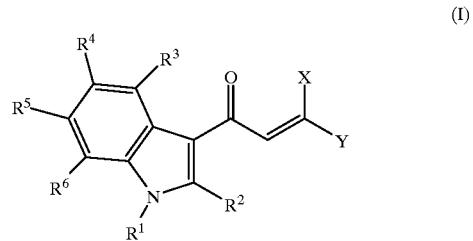

wherein $R^1$ is hydrogen, lower alkyl, or optionally substituted arylsulfonyl, or the like, $R^2$ is hydrogen, lower alkyl, or optionally substituted aralkyl, or the like, $R^3$, $R^4$, $R^5$, and $R^6$ each is independently hydrogen, halogen, trihalogenated lower alkyl, or the like, X is hydroxy or optionally substituted amino, Y is COOR (R is hydrogen or an ester residue), optionally substituted aryl, or optionally substituted heteroaryl, has integrase inhibition activity, and is useful as an anti-HIV drug.

16 Claims, No Drawings

INDOLE DERIVATIVES HAVING AN ANTIVIRAL ACTIVITY

This is a divisional of Ser. No. 09/622,543, filed Aug. 18, 2000, now U.S. Pat. No. 6,333,323 which is a 371 of PCT/JP99/01547, filed Mar. 26, 1999.

TECHNICAL FIELD

This invention relates to novel compounds having an antiviral activity, in detail indole derivatives having an inhibitory activity against viral integrase, and pharmaceutical compositions containing them, especially anti-HIV drugs.

BACKGROUND ART

Among viruses, human immunodeficiency virus (HIV), a kind of retrovirus, is known to cause acquired immunodeficiency syndrome (AIDS). The drug for treatment of AIDS is mainly selected from the group of reverse transcriptase inhibitors (AZT, 3TC, and the like) and protease inhibitors (Indinavir and the like), but they are proved to be accompanied by side effects such as nephropathy and the emergence of resistant virus. Thus, the development of anti-HIV drugs having the other mechanism of action has been desired.

In the above circumstance, integrase has recently been thought to be noteworthy, which is an enzyme relating to the site-specific insertion of viral DNA into chromosome in animal cells, and the research for anti-HIV drugs based on said enzyme inhibition activity is performed ((1) Proc. Natl. Acad. Sci. USA 61 (3), 1013–1020 (1968), KOURILSKY P et al.; (2) J. VIROL. METHODS (NETHERLANDS), 17/1–2(55–61) (1987), F Barin et al.; (3) Proc. Natl. Acad. Sci. USA 90: 2399 (1993), Fesen. MR (1993); (4) CDC AIDS Weekly Pagination:P2 (1990), DeNoon, DJ). Some integrase inhibitors has recently been reported, for example, peptide derivatives described in U.S. Pat. No. 5,578,573, tetrahydronaphthyl derivatives described in GB 2306476A, and acrydone derivatives described in WO 97/38999.

Additionally, in the literature, Khim. Geterotsikl. Soedin. 1973, (11), 1519, some kind of indole derivatives are described, but their therapeutic activity is not described. Moreover, in U.S. Pat. No. 5,475,109, non-condensed heterocyclic compounds substituted with dioxobutanoic acid are described to be useful as an anti influenza viral drug, whose mechanism of the action is the inhibition of cap-dependent endonuclease.

DISCLOSURE OF INVENTION

In the circumstance above, the development of a novel integrase inhibitor is desired. The present inventors have studied intensively to find out that novel indole derivatives have an inhibitory action on integrase, and are useful as antiviral drugs, especially anti-HIV drugs, to accomplish the present invention shown below.

(1) A compound of the formula:

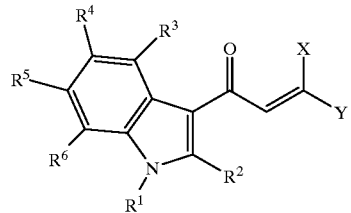

(I)

wherein $R^1$ is hydrogen, lower alkyl, cycloalkyl lower alkyl, lower alkylsulfonyl, lower alkylcarbonyl, optionally substituted aryl, optionally substituted aralkyl, optionally substituted arylsulfonyl, optionally substituted arylcarbonyl, optionally substituted heteroaryl, optionally substituted heteroaralkyl, optionally substituted heteroarylsulfonyl, lower alkoxycarbonyl, optionally substituted sulfamoyl, or optionally substituted carbamoyl;

$R^2$ is hydrogen, lower alkyl, lower alkylcarbonyl, optionally substituted aryl, optionally substituted aralkyl, optionally substituted arylcarbonyl, optionally substituted heteroaryl, optionally substituted heteroaralkyl, optionally substituted arylthio, optionally substituted arylsulfinyl, optionally substituted arylsulfonyl, optionally substituted heterocyclyl lower alkyl, or optionally substituted heterocyclyl sulfonyl;

$R^3$, $R^4$, $R^5$, and $R^6$ each is independently hydrogen, halogen, trihalogenated lower alkyl, hydroxy, lower alkoxy, nitro, amino, optionally esterified carboxy, optionally substituted aralkyloxy, or optionally substituted arylsulfonyloxy;

X is hydroxy or optionally substituted amino;

Y is COOR (R is hydrogen or an ester residue), optionally substituted aryl, or optionally substituted heteroaryl, provided that a compound wherein $R^1$, $R^2$, $R^3$, $R^5$, and $R^6$ each is hydrogen; $R^4$ is hydrogen, methoxy, or chloro; X is hydroxy; and Y is $COOC_2H_5$ is excluded, (hereinafter referred to as a compound (I)), a tautomer, or a pharmaceutically acceptable salt, or a hydrate thereof.

(2) The compound according to above (1) wherein $R^1$ and $R^2$ are not hydrogens at the same time when Y is COOR (R is as defined above).

(3) The compound according to above (1) wherein $R^1$ and $R^2$ are not hydrogens at the same time when X is hydroxy and Y is COOR (R is as defined above).

(4) The compound according to any one of above (1)–(3) wherein $R^1$ is hydrogen or optionally substituted arylsulfonyl.

(5) The compound according to any one of above (1)–(3) wherein $R^2$ is hydrogen, optionally substituted aryl, or optionally substituted aralkyl.

(6) The compound according to any one of above (1)–(3) wherein $R^3$, $R^4$, $R^5$, and $R^6$ each is independently hydrogen or halogen.

(7) The compound according to above (6) wherein $R^3$, $R^5$, and $R^6$ are all hydrogens.

(8) The compound according to any one of above (1)–(3) wherein X is hydroxy.

(9) The compound according to above (1) wherein Y is optionally substituted heteroaryl.

(10) The compound according to above (9) wherein said heteroaryl is a 5–or 6-membered ring containing at least one nitrogen atom.

(11) The compound according to above (10) wherein said heteroaryl is tetrazolyl, triazolyl, or imidazolyl.

(12) The compound according to any one of above (1)–(3) wherein $R^1$ is hydrogen or optionally substituted arylsulfonyl; $R^2$ is hydrogen, optionally substituted aryl, or optionally substituted aralkyl; $R^3$, $R^4$, $R^5$, and $R^6$ each is independently hydrogen or halogen; X is hydroxy.

(13) The compound according to above (1) wherein $R^1$ is hydrogen or optionally substituted arylsulfonyl; $R^2$ is hydrogen, optionally substituted aryl, or optionally substituted aralkyl; $R^3$, $R^4$, $R^5$, and $R^6$ each is independently hydrogen or halogen; X is hydroxy; Y is optionally substituted heteroaryl.

(14) The compound according to above (13) wherein $R^1$ is hydrogen or phenylsulfonyl optionally substituted with halogen; $R^2$ is hydrogen, phenyl optionally substituted with halogen, or phenylmethyl optionally substituted with halogen; $R^4$ is halogen; $R^3$, $R^5$, and $R^6$ are all hydrogens at the same time; X is hydroxy; Y is tetrazolyl.

(15) A pharmaceutical composition containing, as an active ingredient, an indole derivative having a group of the formula: —C(O)CH=C(X)Y (wherein X and Y are as defined above) at the 3-position.

(16) A pharmaceutical composition containing the compound according to any one of above (1)–(14) as an active ingredient.

(17) A composition for inhibiting integrase which contains the compound according to any one of above (1)–(14).

(18) An antiviral composition which contains the compound according to any one of above (1)–(14).

(19) An anti-HIV composition which contains the compound according to any one of above (1)–(14).

(20) An anti-HIV medical mixture comprising a reverse transcriptase inhibitor and/or a protease inhibitor in addition to the integrase inhibitor according to above (17).

The compound (I) of the present invention is characterized in that the indole ring has a group of the formula: —C(O)CH=C(X)Y at the 3-position.

The terms used in the specification are explained below. Each term by itself or as part of (an)other substituent(s) means the same unless particularly mentioned.

The term "lower alkyl" is, for example, a C1–C6 straight or branched chain alkyl group, which includes methyl, ethyl, n-propyl, isopropyl, n-butyl, isobutyl, sec-butyl, tert-butyl, n-pentyl, isopentyl, neopentyl, tert-pentyl, n-hexyl, isohexyl, and the like. A preferable embodiment is C1-C4 alkyl, for example, methyl, ethyl, n-propyl, isopropyl, n-butyl, isobutyl, and tert-butyl.

The term "lower alkoxy" is, for example, a C1–C6 straight or branched chain alkoxy group, which includes methoxy, ethoxy, n-propoxy, isopropoxy, n-butoxy, isobutoxy, sec-butoxy, tert-butoxy, n-pentyloxy, isopentyloxy, n-hexyloxy, isohexyloxy, and the like. A preferable embodiment is C1–C4 alkoxy, for example, methoxy, ethoxy, n-propoxy, isopropoxy, n-butoxy, isobutoxy, tert-butoxy, and the like.

The term "cycloalkyl lower alkyl" is, for example, the above-mentioned lower alkyl group substituted with C3–C6 cycloalkyl, which includes cyclopropyl methyl, 2-cyclopropyl ethyl, 4-cyclopropyl butyl, cyclopentyl methyl, 3-cyclopentyl propyl, cyclohexyl methyl, 2-cyclohexyl ethyl, and the like. A preferable embodiment is C1–C4 alkyl substituted with cyclopropyl, for example, cyclopropyl methyl, 2-cyclopropyl ethyl, and 4-cyclopropyl butyl.

The term "lower alkylsulfonyl" is, for example, a sulfonyl group substituted with the above-mentioned lower alkyl, which includes methylsulfonyl, ethylsulfonyl, n-propylsulfonyl, isopropylsulfonyl, n-butylsulfonyl, isobutylsulfonyl, sec-butylsulfonyl, tert-butylsulfonyl, n-pentylsulfonyl, isopentylsulfonyl, neopentylsulfonyl, tert-pentylsulfonyl, n-hexylsulfonyl, isohexylsulfonyl, and the like. A preferable embodiment is sulfonyl substituted with C1–C4 alkyl, for example, methylsulfonyl, ethylsulfonyl, n-propylsulfonyl, isopropylsulfonyl, n-butylsulfonyl, isobutylsulfonyl, sec-butylsulfonyl, and tert-butylsulfonyl.

The term "lower alkylcarbonyl" is, for example, a carbonyl group substituted with the above-mentioned lower alkyl, which includes, methylcarbonyl, ethylcarbonyl, n-propylcarbonyl, isopropylcarbonyl, n-butylcarbonyl, isobutylcarbonyl, sec-butylcarbonyl, tert-butylcarbonyl, n-pentylcarbonyl, isopentylcarbonyl, neopentylcarbonyl, tert-pentylcarbonyl, n-hexylcarbonyl, isohexylcarbonyl, and the like. A preferable embodiment is carbonyl substituted with C1–C4 alkyl, for example, methylcarbonyl, ethylcarbonyl, n-propylcarbonyl, isopropylcarbonyl, n-butylcarbonyl, isobutylcarbonyl, sec-butylcarbonyl, tert-butylcarbonyl.

The term "lower alkoxycarbonyl" is an carbonyl group substituted with the above-mentioned lower alkoxy, which includes methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, n-pentyloxycarbonyl, isopentyloxycarbonyl, n-hexyloxycarbonyl, isohexyloxycarbonyl, and the like. A preferable embodiment is carbonyl substituted with C1–C4 alkoxy, for example, methoxycarbonyl, ethoxycarbonyl, n-propoxycarbonyl, isopropoxycarbonyl, n-butoxycarbonyl, isobutoxycarbonyl, sec-butoxycarbonyl, t-butoxycarbonyl.

The term "aryl" is, for example, phenyl, naphthyl, or polycyclic aromatic hydrocarbone (phenanthry, and the like), and the like. A preferable embodiment is phenyl and naphthyl.

The term "aralkyl" is, for example, the above-mentioned lower alkyl group substituted with the above-mentioned aryl, which includes benzyl, 2-phenethyl, 1-naphthylmethyl, 2-(2-naphthyl)ethyl, and the like. A preferable embodiment is benzyl.

The term "aralkyloxy" is, for example, an oxy group substituted with the above-mentioned aralkyl, which includes benzyloxy, 2-phenethyloxy, 1-naphthylmethyloxy, 2-(2-naphthyl)ethyloxy, and the like.

The term "arylcarbonyl" is, for example, a carbonyl group substituted with the above-mentioned aryl, which includes benzoyl, naphthylcarbonyl, and the like.

The term "arylthio" is, for example, a thio group substituted with the above-mentioned aryl, which includes phenylthio, naphthylthio, and the like.

The term "arylsulfinyl" is, for example, a sulfinyl group substituted with the above-mentioned aryl, which includes phenylsulfinyl, naphlithylsulfinyl, and the like.

The term "arylsulfonyl" is, for example, a sulfonyl group substituted with the above-mentioned aryl, which includes phenylsulfonyl, naphthylsulfonyl, and the like.

The term "arylsulfonyloxy" is, for example, a sulfonyloxy group substituted with the above-mentioned aryl, which includes phenylsulfonyloxy, naphthylsulfonyloxy, and the like.

The term "heteroaryl" is, for example, a 5- or 6-membered aromatic cyclic group containing 1 to 4 same or different hetero atoms selected from the group of N, O, and S, which includes furyl, thienyl, pyrolyl, oxazolyl, thiazolyl, imidazolyl, pyrazolyl, triazolyl, pyridyl, pyridazinyl, pyrimidinyl, pyrazinyl, triazinyl, tetrazolyl, thiazolyl, and the like. The term "heteroarylsulfonyl" is, for example, a sulfonyl group substituted with the above heteroaryl, which includes furylsulfonyl, thienylsulfonyl, pyrolylsulfonyl, oxazolylsulfonyl, thiazolylsulfonyl, imidazolylsulfonyl, pyrazolylsulfonyl, triazolylsulfonyl, pyridylsulfonyl, pyridazinylsulfonyl, pyrimidinylsulfonyl, pyrazinylsulfonyl, triazinylsulfonyl, tetrazolylsulfonyl, and the like.

The term "heteroaralkyl" is, for example, the above-mentioned lower alkyl group substituted with the above-mentioned heteroaryl, which includes furylmethyl, thienylmethyl, 2-thienylethyl, pyrolylmethyl, 2-pyrolylethyl, oxazolylmethyl, 3-thiazolylpropyl, 4-imidazolylbutyl, pyrazolylmethyl, 2-triazolylethyl, pyridylmethyl, 2-pyridinylethyl, 3-pyridazinylpropyl, pyrimidinylmethyl, 2-pyrazinylethyl, 3-triazinylpropyl, 4-tetrazolylbutyl, and the like.

The term "heterocyclyl" is a 5- to 7-membered non-aromatic cyclic group containing 1 to 3 same or different hetero atoms selected from the group of N, O, and S, which includes, for example, morpholinyl, piperadinyl, dioxanyl, piperidinyl, pyrolidinyl, thiazolidinyl, oxazolidinyl, imidazolidinyl, thiazolinyl, oxazolinyl, imidazolinyl, and the like.

The term "heterocyclyl lower alkyl" is the above-mentioned lower alkyl group substituted with heterocyclic, preferably, morpholinomethyl, and the like.

The above-mentioned "aryl", "arylcarbonyl", "arylsulfonyl", "arylsulfonyloxy", "aralkyl", "aralkyloxy", "heteroaryl", "heteroarylsulfonyl", "heteroaralkyl", "arylthio", "arylsulfinyl", "arylsulfonyl", "heterocyclyl lower alkyl", and "heterocyclyl sulfonyl", if substituted, each may be substituted with same or different 1 to 4 substituent(s) at any substitutable position (ortho, meta, and/or para), which includes, for example, hydroxy, carboxy, halogen (e.g., F, Cl, and Br), trihalogenated lower alkyl (e.g., $CF_3$, $CH_2CF_3$), lower alkyl (e.g., methyl, ethyl, isopropyl, tert-butyl), lower alkoxy (e.g., methoxy, ethoxy, propoxy, butoxy), lower alkoxycarbonyl (e.g., methoxycarbonyl, ethoxycarbonyl, tert-butoxycarbonyl), nitro, amino, amino substituted with lower alkyl (e.g., methylamino, ethylamino, dimethylamino), azido, aryl (e.g., phenyl), aralkyl (e.g., benzyl), an amino-protective group (e.g., trityl), and the like.

"Halogen" includes F, Cl, Br, and I.

"Trihalogenated lower alkyl" includes trifluoromethyl, trichloromethyl, tribromomethyl, trifluoroethyl, and the like.

The substituent of "optionally substituted sulfamoyl" and "optionally substituted carbamoyl" in $R^1$ includes optionally substituted phenyl and lower alkyl (e.g., methyl, ethyl, isopropyl, tert-butyl).

The substituent of "optionally substituted amino" in X includes lower alkyl (e.g., methyl, ethyl), lower alkoxyalkyl (e.g., ethoxymethyl, ethoxyethyl), aralkyl (e.g., benzyl), and the like.

The ester residue of R in Y, or that of "optionally esterified carboxy" in $R^3$, $R^4$, $R^5$, and $R^6$ includes lower alkyl (e.g., methyl, ethyl, tert-butyl), aralkyl (e.g., benzyl, diphenylmethyl), and the like.

Preferable examples of each substituent of the compound (I) are shown below.

A preferable example of $R^1$ includes hydrogen, methyl, n-butyl, cyclopropylmethyl, dimethylsulfamoyl, dimethylcarbamoyl, isopropylsulfonyl, morpholinosulfonyl, tert-butoxycarbonyl, optionally substituted phenylcarbamoyl (the substituent: e.g., halogen), optionally substituted phenylsulfonyl (the substituent: e.g., trifluoromethyl, methyl, isopropyl, benzyl, halogen, methoxy, carboxy, methoxycarbonyl), optionally substituted benzyl (the substituent: azido, halogen, phenyl, carboxy, methoxycarbonyl, nitro, amino), 2-phenethyl, 1-naphthylmethyl, pyridylmethyl, optionally substituted thienyl (the substituent: e.g., carboxy, methoxycarbonyl), and the like. More preferable example includes hydrogen or optionally substituted phenylsulfonyl.

A preferable example of $R^2$ includes hydrogen, n-butyl, optionally substituted phenyl (the substituent: e.g., halogen, methoxy, dimethylamino), optionally substituted benzyl, or phenylpropyl (the substituent: e.g., halogen, methoxy, carboxy, methoxycarbonyl), phenylcarbonyl, optionally substituted phenylthio (the substituent: e.g., halogen, methoxy), optionally substituted phenylsulfinyl (the substituent: e.g., halogen), optionally substituted phenylsulfonyl (the substituent: e.g., halogen, methoxy), morpholinomethyl, and the like. More preferable example includes hydrogen, optionally substituted phenyl, and optionally substituted benzyl.

A preferable embodiment of $R^3$, $R^4$, $R^5$, and $R^6$ is that all are hydrogens or that $R^4$ is halogen (especially, chlorine) and the others are hydrogens.

Preferable example of X is hydroxy.

Preferable example of Y includes COOR (R is hydrogen or an ester residue), or optionally substituted heteroaryl. Preferable example of R is hydrogen in light of the anti viral activity. Moreover the compound wherein R is an ester residue is useful as a synthetic intermediate. Preferable example of heteroaryl in Y is a 5- or 6-membered cyclic group containing at least one nitrogen atom in the ring, more preferably, tetrazolyl, triazolyl, imidazolyl, and thiazolyl, especially, tetrazolyl.

The compound (I) usually shows chemical equilibrium in a solution and the like as shown below.

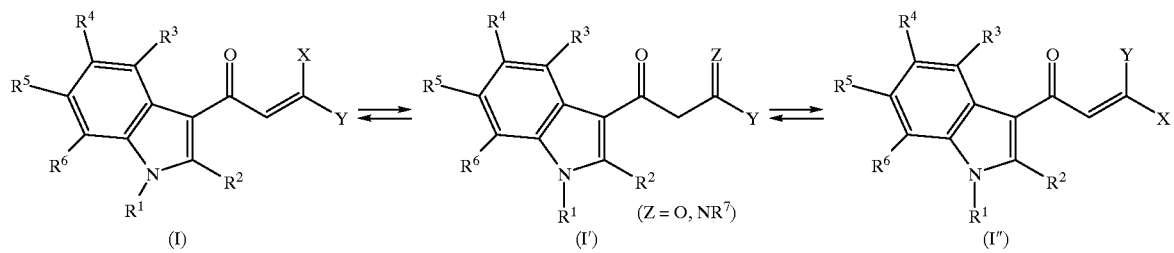

wherein $R^7$ is hydrogen or the substituent on the imino group.

In the chemical equilibrium shown above, the compound (I', wherein Z=O) is the diketone derivative of the compound (I, wherein X=OH), and the compound (I") and the compound (I) are cis-trans isomers with respect to the olefin part of the 3-side chain. All the theoretically possible tautomers of the compound (I) including these compounds are in the scope of the present invention. In the specification, the term "the compound (I)" may be merely used as general term of the compound (I) and its all tautomers. Moreover, most of N.M.R. data in the following examples correspond to the above-described form (I) depending on the measuring condition.

As a salt of the compound (I), any of pharmaceutically acceptable salts can be used, including base addition salts, for example, alkali metal salts such as sodium or potassium salts; alkaline-earth metal salts such as calcium or magnesium salts; ammonium salts; aliphatic amine salts such as trimethylamine, triethylamine, dicyclohexylamine, ethanolamine, diethanolamine, triethanolamine, or procaine salts; aralkylamine salts such as N,N-dibenzylethylenediamine salts; heterocyclic aromatic amine salts such as pyridine, picoline, quinoline, or isoquinoline salts; quaternary ammonium salts such as tetramethylammonium, tetraethylammonium, benzyltrimethylammonium, benzyltriethylammonium, benzyltributylammonium, methyltrioctylammonium or tetrabutylammonium salts; and basic amino acid salts such as arginine or lysine salts. Acid addition salts include, for example, mineral acid salts such as hydrochlorides, sulfates, nitrate, phosphates, carbonates, hydrogen carbonates or perchlorates; organic acid salts such as acetates, propionates, lactates, maleates, fumarates, tartrates, malates, succinates, or ascorbates; sulfonates such as methanesulfonates, isethionates, benzenesulfonates, or p-toluenesulfonates; and acidic amino acid salts such as aspartates or glutamates.

Furthermore, hydrates and various solvates of the compound (I) are in the scope of the present invention.

The method of the preparation of the compound (I) is explained below.

The compounds (I) are novel indole derivatives, on the other hand, known compounds having indole structure as a basic skeleton have already been reported (Hetrocyclic Compounds, Indoles Part 1–3, (Wiley Interscience), The chemistry of Indoles (Academic Press), etc). Accordingly, a person skilled in the art can easily prepare the compounds (I), for example, by applying these known compounds as starting materials to widely known organic reactions. The representative general method of the preparation of the compound (I) is shown below.

(1) Forming of the 3-side chain (The basic synthetic route)

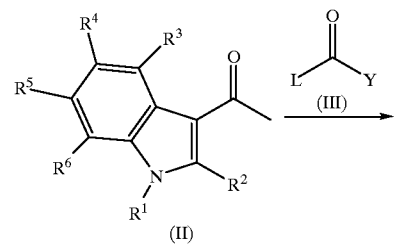

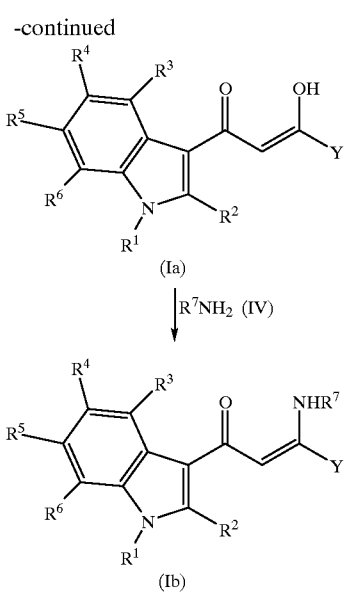

(A) In case of X=OH

For example, various 3-acetylindole derivatives (II) obtained in accordance with the methods described in the literature (Tetrahedron 48, 10645(1992)) and the like, react with the above compound (III) (wherein L is a leaving group, for example, a halogen or $OR^8$ ($R^8$ is a lower alkyl and the like) and the like), preferably in the presence of base, to give the compound (Ia).

Examples of the reaction solvent include tetrahydrofuran (THF), dioxane, and the like. Examples of the base include sodium ethoxide, potassium t-butoxide, lithium bis(trimethylsilyl)amide (LHMDS), and the like. The reaction temperature is approximately –100 to 100° C., preferably –70 to 60° C.

Examples of the compound (III) include dimethyl oxalate, (diethyl oxalate), methyl oxalyl chloride, (ethyl oxalyl chloride), 2-trityl-2H-tetrazole-5-carboxylic acid ethyl ester, 1-trityl-1H-1,2,4-triazole-3-carboxylic acid ethyl ester, 1-tritylimidazole-2-carboxylic acid ethyl ester, phthalic anhydride, o-methoxybenzoyl chloride, and the like.

(B) In case of X=NHR$^7$

The above compound (Ia) reacts with the above compound (IV) ($R^7$ is a hydrogen or the substituent on the amino group) or their acid addition salt to give the compound (Ib).

Examples of the reaction solvents include methanol, ethanol, and the like. The reaction temperature is approximately –10 to 100° C., preferably room temperature to 100° C.

(2) The introduction of the substituent ($R^1$) at the 1-positon

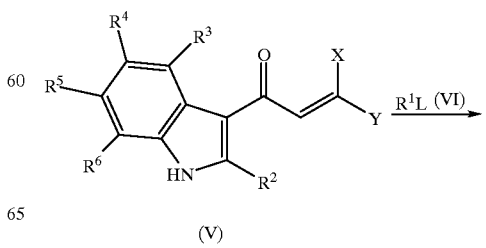

-continued

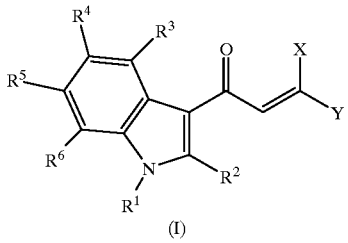

(I)

For example, the above compound (V) obtained in accordance with the method described in (1) can react with the compound (VI) (wherein L is a leaving group), or isocyanate derivatives which can be introduced as $R^1$, or the like, if desired in the presence of base, to give the compound (I).

Examples of the bases include NaH, $K_2CO_3$, and the like. Examples of the solvents include THF, dioxane, and the like.

Examples of the compound (VI) include various kinds of sulfonyl chloride (e.g., (substituted) benzenesulfony chloride, 2-thiophenesulfonyl chloride, (substituted) aminosulfonyl chloride, alkylsulfonyl chloride, and the like), halogenated alkyl (e.g., methyl iodide, butyl bromide, cyclopropyl bromide, and the like), halogenated aralkyl (e.g., (substituted) benzyl, picolyl, naphthyl, biphenylmethyl, and the like), carbamoyl chloride (e.g., dimethylcarbamoyl chloride and the like), halogenated acyl (e.g., p-p-fluorobenzoyl chloride and the like), and the like.

Examples of isocyanate derivatives include (substituted) aryl isocyanate (e.g., phenyl isocyanate and the like), and the like.

The reaction temperature is approximately −100 to 100° C., preferably −20 to 60° C. Moreover, this reaction is suitable for the case of X=OH.

Before the reaction described in any one of (1) or (2), if desired, the functional group may be protected in accordance with methods widely known to a person skilled in the art, and after that, if desired, ester hydrolysis or deprotection may be carried out.

Use of the compounds of the present invention is explained below.

The compounds (I) are useful as pharmaceutical compositions such as antiviral drugs. The compounds (I) have remarkable inhibition activity against viral integrase. Accordingly, the compounds (I) can be used for the prevention or treatment of various diseases caused by virus which at least produce integrase to grow in infected animal cells. For example, the compounds are useful as integrase inhibitors against retrovirus (e.g., HIV-1 and the like) and as anti-HIV drugs.

Furthermore, the compounds (I) can be used in the combination therapy with anti-HIV drugs having a different mechanism of action such as reverse transcriptase and/or protease inhibitor.

The compounds (I) of the present invention can be administered orally or parenterally. For oral administration, the compounds of the present invention can be used in any form of usual formulations, for example, solid formulations such as tablets, powders, granules, capsules; aqueous formulations; oleaginous suspensions; solutions such as syrup or elixir. For parenteral administration, the compounds of the present invention can be used as an aqueous or oleaginous suspension injection, or nose drops. In the preparation of such formulations, conventional excipients, binding agents, lubricants, aqueous solvents, oleaginous solvents, emulsifying agents, preservatives, stabilizers, and the like can be optionally used.

Although an appropriate dosage of the compound of the present invention varies depending on the administration route, age, body weight, conditions of the patient, and kind of disease, in the case of oral administration, the daily dosage can be between approximately 0.05–3000 mg, preferably approximately 0.1–1000 mg, an adult a day. The daily dosage can be administered in divisions. In the case of parenteral administration, the daily dosage can be between approximately 0.01–1000 mg, preferably approximately 0.05–500 mg.

Furthermore, all kinds of indole derivatives having the group of the formula: —C(O)CH=C(X)Y wherein X and Y are defined above, at the 3-position of the indole can be used as pharmaceutical compositions such as antiviral drugs, as well as the compound (I). In said indole derivative, a wide variety of substituents can be introduced at any position other than the 3-position, as far as they do not have a negative effect on the pharmacological activity. The above indole derivatives can be prepared in accordance with the preparation of the compound (I).

The compound (I) are useful as intermediates of drug, starting materials of the preparation, and the like. For example, the compounds (I) wherein R defined in Y is an ester residue can be easily derived to the compound wherein R is a hydrogen by deprotection.

BEST MODE FOR CARRYING OUT THE INVENTION

Examples of the present invention are shown below. Reactions are usually carried out under nitrogen atmosphere, and reaction solvents are used as dried over molecular sieve and the like. Extracts are dried over sodium sulfate or magnesium sulfate and the like.

(Abbreviation)

Me=methyl; Et=ethyl; iPr=isopropyl; Ph=phenyl; Bn=benzyl; Ac=acetyl; Boc=t-butoxycarbonyl; MeOH=methanol; EtOH=ethanol; MEK=methyl ethyl ketone; EtOAc=ethyl acetate; $CHCl_3$=chloroform; MeCN=acetonitrile; DMF=N,N-dimethylformamide; DMA=N,N-dimethylacetamide; $Et_2O$=ethylether; i-$Pr_2O$=isopropylether; LHMDS=lithium bis(trimethylsilyl)amide; Hex=n-hexane; THF=tetrahydrofuran; DMSO=dimethylsulfoxide; aq.dioxane=aqueous dioxane; Tet=2-H-tetrazol-5-yl; Tri=1H-[1,2,4]-triazol-3-yl; Imi=2-imidazolyl. Furthermore, as an example for expression of the substituents, Ph(2,5-Cl) represents phenyl group substituted with Cl at 2- and 5-position.

REFERENCE EXAMPLE 1

3-Acetyl-2-benzylindole

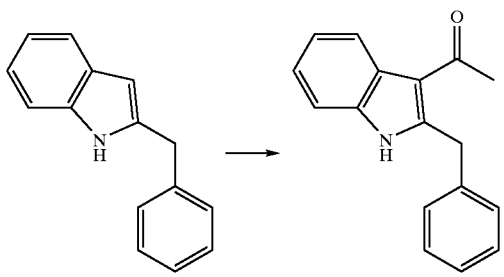

To a solution of 29.5 g (39 mmol) of dimethylacetamide was added dropwise under ice-cooling 7.00 g (76.9 mmol) of phosphorus oxychloride. After stirring for 30 min at room temperature, to the mixture was added 8,00 g (38.6 mmol) of 2-benzylindole (prepared in accordance with the literature (Khim.Geterotsikl.Soedin.1994,p133)). After stirring for 2 hours at 100° C., the mixture was poured to ice-water, neutralized with 2N NaOH, extracted with ethyl acetate. The extract was washed with water, dried, and concentrated. The obtained crystal was washed with n-hexane to give 5.1 g of the titled compound. Yield: 52%.

NMR(CDCl$_3$) δ:2.72(3H, s), 4.60(2H, s), 7.10–7.48(8H, m), 7.94–8.20(1H, m),8.20(1H, brs).

REFERENCE EXAMPLE 2

3-Acetyl-1-benzenesulfonylindole-5-carboxylic acid diphenylmethyl ester

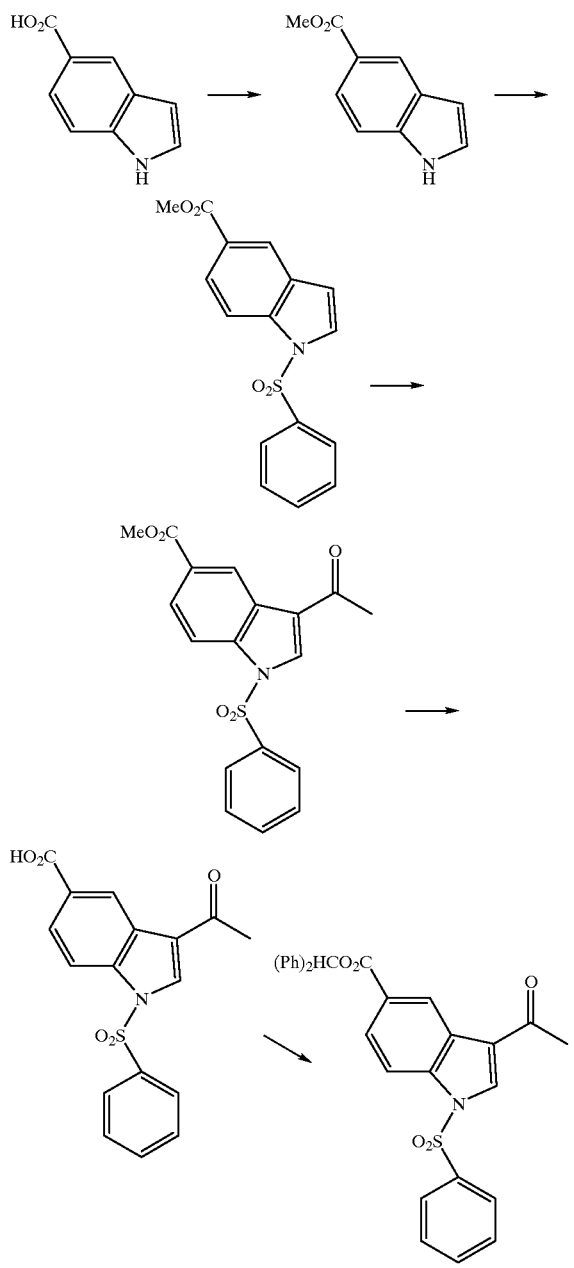

(1) To a solution of 4.8 g (29.8 mmol) of indole-5-carboxylic acid in ether (200 ml) was added dropwise etheral diazomethane until the yellow color of diazomethane did not disappear. The mixture was concentrated and the obtained residue was chromatographed on silica gel (ethyl acetate as an eluant) to give 4.5 g of indole-5-carboxylic acid methyl ester. Yield: 86%.

NMR(CDCl$_3$) δ: 3.93(3H, s), 6.65(1H, m), 7.27(1H, m), 7.40(1H, d, J=8.4 Hz), 7.91(1H, d, J=8.4 Hz, 1.2 Hz), 8.40(1H, brm), 8.42(1H, m).

(2) To a solution of 5.3 g (30 mmol) of the above-mentioned compound in THF (150 ml) was added 6.05 g (150 mmol) of powderd NaOH and 0.51 g of tetra-n-butylammonium bromide. To the above suspension was added under ice-cooling, a solution of 6.41 g (36 mmol) of benzenesulfonyl chloride in THF (10 ml). After stirring for 30 min at the same temperature, the resulting inorganic salt was filtered off, and the THF solution was concentrated under reduced pressure. The obtained crystal was washed with ethyl acetate to give 7.24 g of 1-benezenesulfonylindole-5-carboxylic acid methyl ester. Furthermore, the ethyl acetate solution used for washing was washed with aqueous ammonia, washed with water, and dried. The solution was concentrated and the residue was crystallized with ether, then washed with ether to give 2.0 g of the above-mentioned compound. Total yield: 97%.

NMR(CDCl$_3$) δ:3.92(3H, s), 6.73(1H, d, J=3.8 Hz), 7.45–8.03(8H, m),8.26(1H, m).

(3) To a suspension of 10.7 g (80 mmol) of aluminum chloride in dichloroethane (80 ml) was added dropwise 4.83 g (40 mmol) of acetic anhydride. After stirring for 15 min, to the mixture was added dropwise 6.31 g (20 mmol) of the above-mentioned 1-benzenesulfonylindole-5-carboxylic acid methyl ester in dichloroethane (60 ml). After stirring for 2 hours at room temperature, to the mixture were added 5.33 g (40 mmol) of aluminum chloride and 2.04 g (20 mmol) of acetic anhydride. After stirring for 30 min, the mixture was poured into ice-water, extracted with ethyl acetate. The extract was washed twice with water, aqueous sodium bicarbonate and dried, and then concentrated. The obtained crystal was washed with isopropyl ether to give 6.82 g of 3-acetyl-1-benzenesulfonylindole-5-carboxylic acid methyl ester. Yield: 96%.

NMR(CDCl$_3$) δ: 2.60(3H, s), 3.93(3H, s), 7.48–7.68(3H, m), 7.94–8.00(2H, m), 8.09(1H, dd, J=8.8 Hz, 1.6 Hz), 8.26(1H, s), 9.00(1H, d, J=1.6 Hz).

(4) To a solution of 0.18 g (0.5 mmol) of the above-mentioned compound in dichloromethane (2 ml) was added at −35–−40° C., 1.5 ml of boron tribromide(1 M solution in dichloromethane). After warming to room temperature, the mixture was refluxed for 15 min. The mixture was diluted with water, extracted with ethyl acetate. The extract was washed with water and dried, and concentrated. The obtained crystal was washed with ether to give 0.1 g of 3-acetyl-1-benzenesulfonylindole-5-carboxylic acid. Yield: 60%.

NMR(d$_6$-DMSO) δ: 2.62(3H, s), 7.62–8.23(7H, m), 8.81 (1H, m), 8.93(1H, s).

(5) To a solution of 750 mg (2.2 mmol) of the above-mentioned compound in THF (25 ml) was added 510 mg (2.64 mmol) of diphenyldiazomethane. After stirring for 16 hours at 60° C., the mixture was concentrated under reduced pressure. The obtained residue was chromatographed on silica gel (¼ ethyl acetate/toluene as eluant) to give 530 mg of the titled compound as an oil. Yield: 48%.

NMR(CDCl$_3$) δ: 2.60(3H, s), 7.14–7.66(14H, m), 7.93–8.01(3H, m), 8.16(1H, dd, J=8.0, 1.4 Hz), 8.26(1H, s), 9.13(1H, d, J=1.4 Hz).

REFERENCE EXAMPLE 3

3-Acetyl-5-chloro-1-phenethylindole

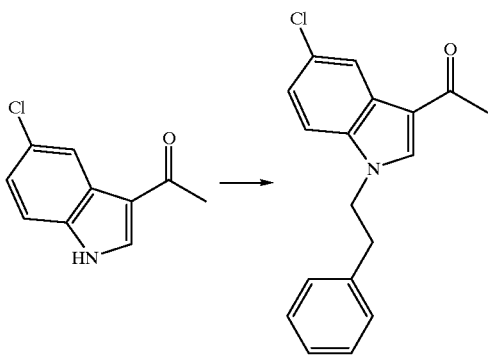

(1) To a mixture of 0.58 g (3 mmol) of 3-acetyl-5-chloroindole, 1.42 g (5.4 mmol) of triphenylphosphine and 0.66 g (5.4 mmol) of phenethyl alcohol in THF (12 ml) was added under ice-cooling, 1.09 g (5.4 mmol) of diisopropyl azodicarboxylate. After stirring for 3 hours at room temperature, the mixture was concentrated under reduced pressure. The obtained residue was chromatographed on silica gel (¼ ethyl acetate/toluene as eluant) to give 0.58 g of the titled compound as an oil. Yield: 65%.

NMR(CDCl$_3$) δ:2.38(1H, s), 3.12(2H, t, J=7.2 Hz), 4.36 (2H, t, J=7.2 Hz), 6.97–7.01(2H, m), 7.20–7.30(5H, m), 7.38(1H, s), 8.38(1H, d, J=1.8 Hz).

REFERENCE EXAMPLE 4

3-Acetyl-6-benzenesulfonyloxy-1-benzylindole

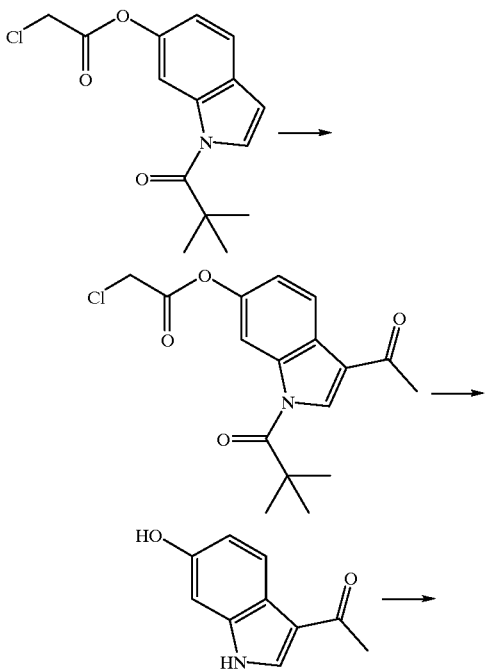

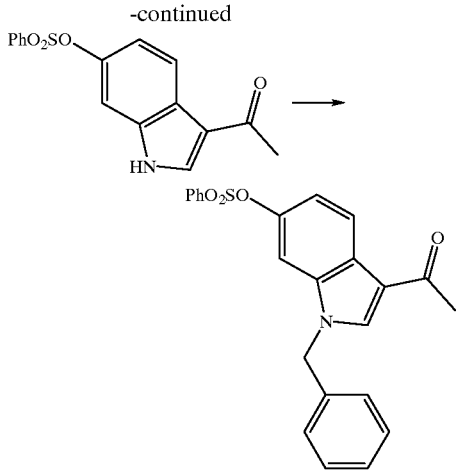

(1) To a suspension of 9.5 g (72 mmol) of aluminum chloride in dichloroethane (47.5 ml) was added dropwise 3.64 g (36 mmol) of acetic anhydride. After stirring for 15 min at room temperature, to the above mixture was added dropwise 3.3 g (11 mmol) of 6-chloroacetoxy-1-pivaloylindole (prepared in accordance with the literature (SYNTHESIS, p1018, 1994) in dichloroethane (33 ml). After stirring for 1 hour at room temperature, the mixture was poured into ice-water. The mixture was extracted with ethyl acetate. The extract was washed twice with water and aqueous sodium bicarbonate, and dried. The solution was concentrated and the obtained residue was chromatographed on silica gel (ethyl acetate as eluant) to give 1.23 g of 3-acetyl-6-chloroacetoxy-1-pivaloylindole as an oil. Yield: 36%.

NMR(CDCl$_3$) δ: 1.56(9H, s), 2.59(3H, s), 4.33(2H, s), 7.17(1H, dd, J=8.8 Hz, 2.1 Hz), 8.28(1H, d, J=2.1 Hz), 8.34(1H, s), 8.35(1H, d, J=8.8 Hz).

(2) To a solution of 0.278 g (1 mmol) of the above-mentioned compound in THF (5 ml) was added 2.5 ml of 1N lithium hydroxide. After stirring for 30 min at room temperature, to the reaction mixture was added 2.6 ml of 1N hydrochloric acid. The solution was concentrated under reduced pressure and the obtained crystal was dissolved into ethyl acetate. The ethyl acetate was washed with aqueous sodium bicarbonate, saturated brine, and dried. The solution was concentrated to give 0.145 g of 3-acetyl-6-hydroxyindole as crystal. Yield: 83%. m.p.: 135–140° C.

NMR(d$_6$-DMSO) δ: 2.39(3H, s), 6.66(1H, dd, J=8.6 Hz, 2.2 Hz), 6.79(1H, d, J=2.22 Hz), 7.91(1H, d, J=8.6 Hz), 8.08(1H, d, J=2.4 Hz), 11.6(1H, s).

(3) In a manner similar to that described in Reference example 2 (2), the above-mentioned compound was reacted with benzenesulfonyl chloride to give 3-acetyl-6-benzenesulfonyloxyindole.

NMR(CDCl$_3$) δ: 2.52(3H, s), 6.67(1H, dd, J=8.6 Hz, 1.8 Hz), 7.30(1H, d, J=1.8 Hz), 7.47–7.83(5H, m), 7.87(1H, d, J=3.0 Hz), 8.21(1H, d, J=8.6 Hz), 9.0(1H, brm).

(4) To a solution of 0.63 g (2 mmol) of the above-mentioned compound in acetonitrile (8 ml) were added 0.41 g (2.4 mmol) of benzyl bromide and 0.55 g (4 mmol) of potassium carbonate. After stirring under refluxing for 30 min, the reaction mixture was poured into ice-water, extracted with ethyl acetate. The extract was washed with water and dried. The solution was concentrated and the obtained residue was chromatographed on silica gel (½ ethyl acetate/toluene as eluant) to give 0.72 g of the titled compound as an oil. Yield: 89%.

NMR(CDCl$_3$) δ: 2.48(3H, s), 5.27(2H, s), 6.73(1H, dd, J=8.6 Hz, 2.0 Hz), 7.08–7.78(12H, m), 8.23(1H, d, J=8.6 Hz).

REFERENCE EXAMPLE 5

3-Acetyl-1-tert-butoxycarbonyl-5-methoxymethyloxyindole

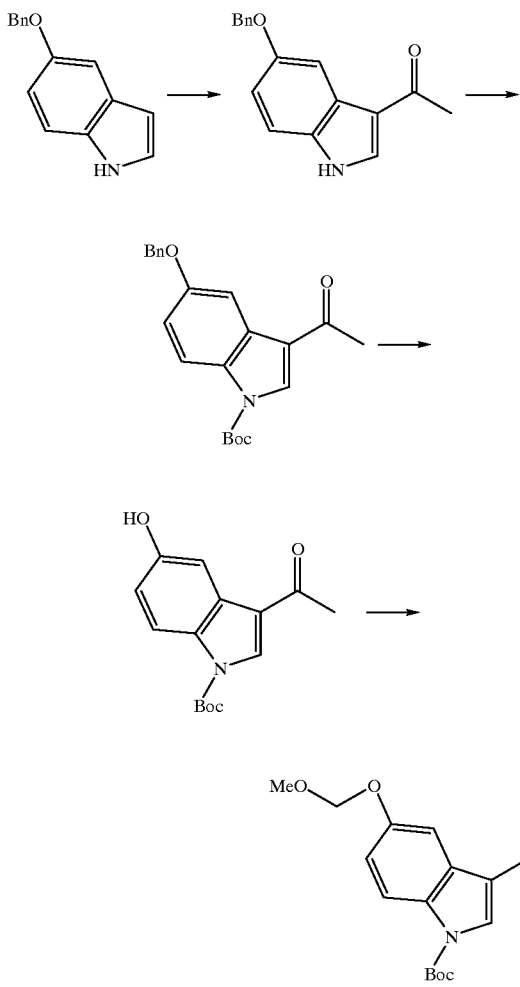

(1) In a manner similar to that described in Reference example 1, 5-benzyloxyindole was reacted with DMA/POCl$_3$ to give 3-acetyl-5-benzyloxyindole.

NMR(CDCl$_3$) δ: 2.53(3H, s), 5.14(2H, s), 7.01(1H, dd, J=8.8 Hz, 2.4 Hz), 7.26–7.52(6H, m), 7.80(1H, d, J=3.2 Hz), 8.01(1H, d, J=2.4 Hz), 8.65(1H, brm).

(2) To a solution of 2.0 g (7.54 mmol) of the above-mentioned compound and 0.05 g (0.4 mmol) of 4-dimethylaminopyridine in THF (20 ml) was added dropwise at room temperature 1.97 g (9.05 mmol) of di-tert-butyl dicarbonate in THF (5 ml). After stirring for 30 min, the reaction mixture was concentrated under reduced pressure. The obtained crystal was washed with isopropyl ether to give 2.58 g of 3-acetyl-5-benzyloxyl-tert-butoxycarbonylindole. Yield: 94%. m.p.: 114–116° C.

NMR(CDCl$_3$) δ: 1.70(9H, s), 2.55(3H, s), 5.15(2H, s), 7.06(1H, dd, J=9.2 Hz, 2.6 Hz), 7.30–7.51(5H, m), 7.98(1H, d, J=9.2 Hz), 7.99(1H, d, J=2.6 Hz), 8.19(1H, s).

(3) To a solution of 2.58 g (7.06 mmol) of the above-mentioned compound in ethyl acetate (51 ml) was added 0.13 g of palladium oxide. Hydrogen gas was introduced to this mixture under atmospheric pressure at room temperature. It absorbed 196 ml of hydrogen gas during 20 min. The catalyst was filtered off, and the filtrate was concentrated. The obtained crystal was washed with isopropyl ether to give 1.7 g 3-acetyl-1-tert-butoxycarbonyl-5-hydroxyindole. Yield: 88%.

(4) To a solution of 1.8 g (6.54 mmol) of the above-mentioned compound in dichloromethane(18 ml) were addled successively 2 ml of 50% NaOH aqueous solution, 0.28 g (10% mole) of tetra-n-hexylammonium bromide and 8 ml of methoxymethyl chloride (1M solution in dichloromethane) at room temperature, and the mixture was stirred. After confirming the disappearance of the starting material, to the reaction mixture was added ice-water, and the dichloromethane layer was washed with water, saturated brine, and dried. The solvent was concentrated and the obtained crystal was washed with chilled n-hexane to give 1.98 g of the titled compound. Yield: 95%

REFERENCE EXAMPLE 6

3-Acetyl-5-chloro-2-(4-fluorophenethyl)-indole

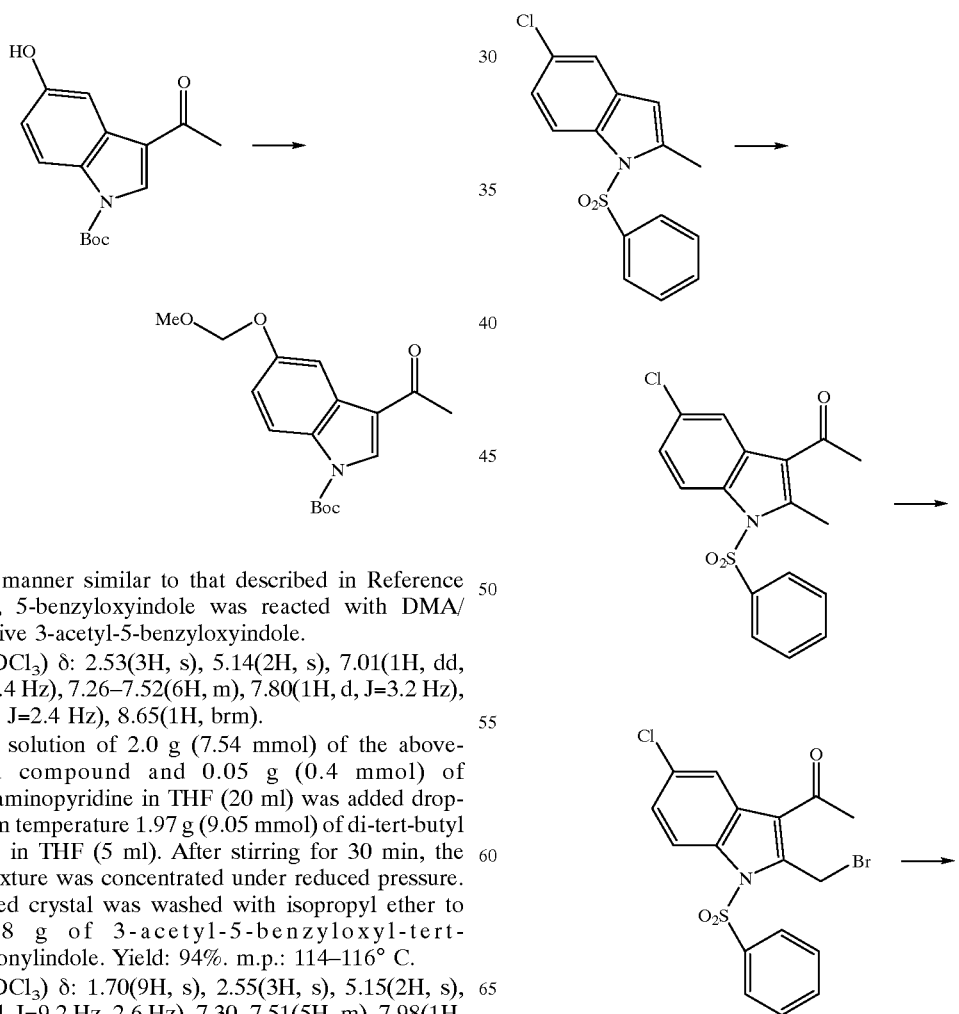

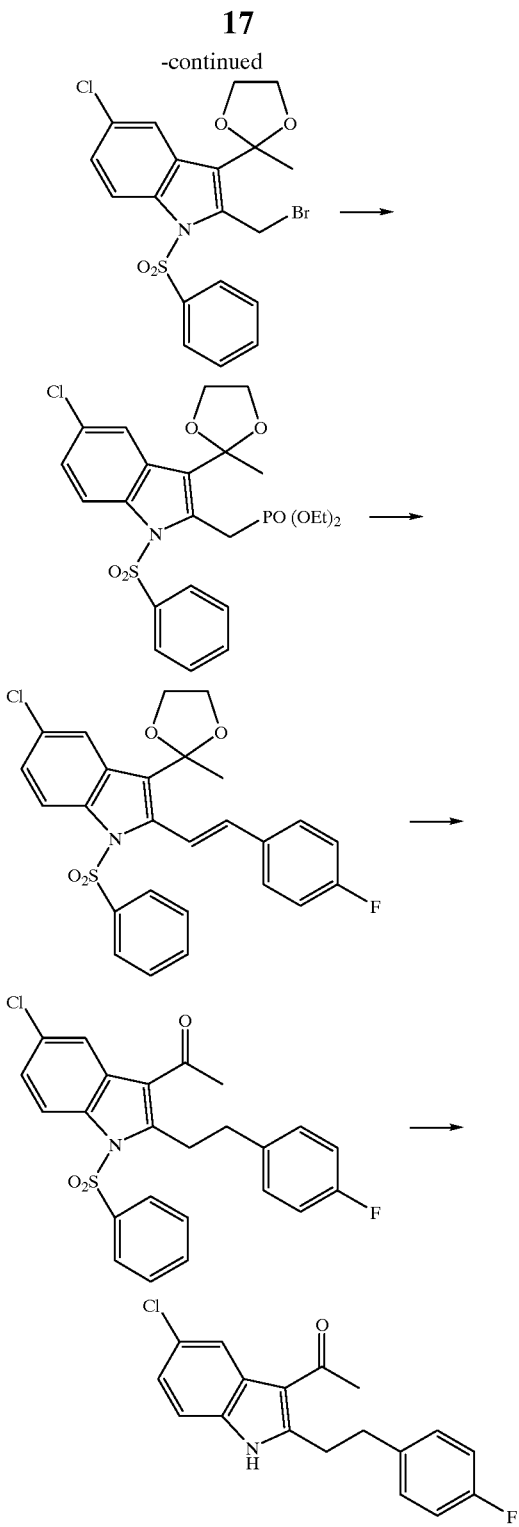

(1) 1-Benzenesulfonyl-5-chloro-2-methylindole prepared in accordance with the literature (J. Org. Chem., 47, 757 (1982) was reacted with Ac₂O/AlCl₃ in a similar manner described in Reference example 2 (3) to give 3-acetyl-1-benzenesulfonyl-5-chloro-2-methylindole. Yield: 86%.

NMR(CDCl₃) δ: 2.61(3H, s), 2.89(3H, s), 7.32(1H, dd, J=9.0 Hz, 2.1 Hz), 7.46–7.65(3H, m), 7.79–7.83(2H, m), 7.91(1H, d, J=2.1 Hz), 8.23(1H, d, J=9.0 Hz).

(2) To a solution of 1.40 g (4 mmol) of the above-mentioned compound in carbon tetrachloride (50 ml) were added 0.71 g of N-bromosuccinimide and 10 mg of benzoyl peroxide, and the mixture was stirred at reflux for 3.5 hours. The reaction mixture was cooled and the precipitated crystal was filtered off. The filtrate was concentrated and allowed to stand. The obtained crystal was washed with a small amount of ethyl acetate to give 1.51 g of 3-acetyl-1-benzenesulfonyl-2-bromomethyl-5-chloroindole. Yield: 88%.

m.p.:155° C. NMR(CDCl₃) δ: 2.73(3H, s), 5.40(2H, s), 7.37(1H, dd, J=9.0 Hz, 2.1 Hz), 7.47–7.66(3H, m), 7.93(1H, d, J=2.1 Hz), 7.95–7.99(2H, m), 8.11(1H, d, J=9.0 Hz).

(3) To a solution of 1.42 g (3.35 mmol) of the above-mentioned compound in benzene (50 ml) were added 1.04 g of ethylene glycol and 0.06 g of pyridinium p-toluenesulfonate, and the mixture was refluxed azeotropically for 18 hours. After cooling, the reaction mixture was poured into aqueous sodium bicarbonate and extracted with ethyl acetate. The extract was washed with water and dried, and then concentrated. The residue was washed with ether to give 1.45 g of 1-benzenesulfonyl-2-bromomethyl-5-chloro-3-(2-methyl[1,3]dioxoran-2-yl)-indole. Yield: 92%. m.p.: 145–146° C.

NMR(CDCl₃) δ: 1.73(3H, s), 3.78(2H, brs), 4.06(2H, brs), 5.35(2H, brs), 7.27–7.60(4H, m), 7.85–7.89(2H, m), 7.94(1H, d, J=2.1 Hz), 8.02(1H, d, J=9.0 Hz).

(4) The mixture of 0.85 g (1.8 mmol) of the above-mentioned compound and 0.36 g (2.2 mmol) of triethyl phosphite was stirred at 145–150° C. for 1.5 hours. After cooling, the reaction mixture was diluted with ether/n-hexane(1:1, v/v) to give 0.91 g of [1-benzenesulfonyl-5-chloro-3-(2-methyl[1,3]dioxoran-2-yl)-indole-2-ylmethyl]-phosphonic acid diethyl ester as a crystal. Yield: 96%. m.p.: 126–127° C.

NMR(CDCl₃) δ: 1.31(6H, t, J=7.2 Hz), 1.79(3H, s), 3.93–4.25(10H,m), 7.20–7.58(6H, m), 7.76(1H, d, J=2.1 Hz), 7.98(1H, d, J=9.0 Hz).

(5) To a mixture of 1.43 g (2.71 mmol) of the above-mentioned compound and 0.40 g (3.25 mmol) of 4-fluorobenzaldehyde in THF (27 ml) was added 0.22 g (5.5 mmol) of sodium hydride (60% dispersion in mineral oil) under ice-cooling. After stirring at room temperature for 18 hours, to the above mixture were added 2 ml of DMF and 0.11 g of 4-fluorobenzaldehyde. After stirring for 3 hours, the reaction mixture was treated with aqueous solution of ammonium chloride and extracted with ethyl acetate. The extract was washed with water, saturated brine and dried, and then concentrated. The residue was crystallized with ethyl acetate/n-hexane (1/4, v/v) to give 1.02 g of 1-benzenesulfonyl-5-chloro-2-[2-(4-fluorophenyl)-vinyl]-3-(2-methyl[1,3]dioxoran-2-yl)-indole. Yield: 76%.

m.p.: 149–151° C. NMR(CDCl₃) δ: 1.63(3H, s), 3.45–3.50(2H,m), 3.91–3.96(2H, m), 6.87(1H, d, J=16.5 Hz), 7.10(2H, t, J=9.0 Hz), 7.26–7.36(4H, m), 7.46–7.55 (5H, m), 7.82(1H, d, J=2.4 Hz), 8.18(1H, d, J=9.0 Hz).

(6) To a solution of 0.82 g (1.64 mmol) of the above-mentioned compound in ethyl acetate (10 ml) and ethanol (20 ml) was added 82 mg of 10% Pd-C, and the mixture was hydrogenated for 18 hours under atmospheric pressure at room temperature. The solution was filtered and concentrated. The residue was crystallized from ethanol to give 0.41 g of 1-benzenesulfonyl-5-chloro-2-[2-(4-fluorophenethyl)]-3-(2-methyl[1,3]dioxoran-2-yl)-indole. Yield: 51%. m.p.: 175–177° C. Then to a solution of 0.244 g of the above compound in dioxane (6 ml) was added 2 ml of 1N hydrochloric acid. After refluxing for 30 min at 80–85° C., the solution was concentrated under reduced pressure. The residue was extracted with ethyl acetate, and dried to give quantitatively 3-acetyl-1-benzenesulfonyl-5-chloro-2-[2-(4-fluorophenethyl)]-indole.

(7) To a solution of 0.24 g of the above-mentioned compound in dioxane (5 ml) was added 1.2 ml of 1N lithium hydroxide. After refluxing for 1 hour under heating, the reaction mixture was extracted with ethyl acetate. The extract was washed with water and dried. The solvent was concentrated and the residue was washed with ether to give 0.135 g of the titled compound. Yield: 88%. m.p.: 170–172° C.

NMR(CDCl$_3$) δ: 2.68(3H, s), 3.02(2H, t, J=7.8 Hz), 3.39 (2H, t, J=7.8 Hz), 6.95(2H, t, J=8.4 Hz), 7.09–7.22(4H, m), 7.93(1H, d, J=1.8 Hz), 8.25(1H, brs).

REFERENCE EXAMPLE 7

3-Acetyl-5-chloro-2-(morpholin-4-yl)methylindole

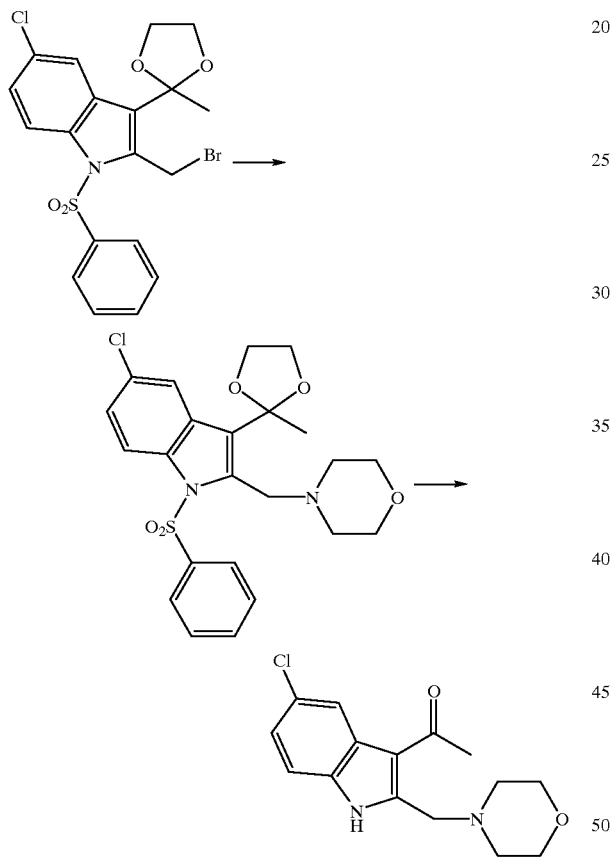

(1) To a solution of 0.236 g (0.5 mmol) of 1-benzenesulfonyl-2-bromomethyl-5-chloro-3-(2-methyl[1,3]dioxoran-2-yl)-indole prepared in Reference example 6 (3) in THF (4 ml) was added 0.11 g (1.25 mmol) of morpholine, and the mixture was stirred at room temperature for 2 hours. The solution was concentrated and the residue was dissolved into ether. The ether was washed with water and dried, and then concentrated. The obtained crystal was collected by filtration and washed with a small account of ether to give 0.214 g 1-benzenesulfonyl-5-chloro-3-(2-methyl[1,3]dioxoran-2-yl)-2-(morpholin-4-yl)methylindole. Yield: 90%. m.p.: 195–198° C.

NMR(CDCl$_3$) δ: 1.74(3H, s), 2.35–2.40(4H, m), 3.17–3.25(4H, m), 3.70–3.78(2H, m), 4.01–4.07(2H, m), 4.11(2H, s), 7.24–7.60(4H, m), 7.85–7.90(2H, m), 7.96(1H, d, J=2.1 Hz), 8.06(1H, d, J=9.0 Hz).

(2) To a solution of 0.186 g (3 mmol) of ethanethiol in DMF (2 ml) was added 0.12 g (3 mmol) of sodium hydride (60% dispersion in mineral oil). To this solution was added 0.475 g (1 mmol) of the above-mentioned compound and the mixture was heated at 80° C. for 30 min. The DMF was evaporated under reduced pressure and the residue was dissolved into ethyl acetate. The ethyl acetate was washed with water and dried. The solvent was concentrated and the residue was crystallized from diisopropyl ether to give 0.296 g of crystal. The mixture of this compound in dioxane (8 ml) and 1N hydrochloric acid (3 ml) was stirred at room temperature for 30 min. The usual work-up gave 0.23 g of the above-mentioned compound. Yield: 81%. m.p.: 120–121° C.

NMR(CDCl$_3$) δ: 2.60–2.64(4H, m), 2.65(3H, s), 3.77–3.82(4H, m), 4.12(2H, s), 7.21(1H, dd, J=8.7 Hz, 2.1 Hz), 7.34(1H, d, J=8.7 Hz), 7.93(1H, d, J=2.1 Hz), 9.50(1H, brs).

REFERENCE EXAMPLE 8

3-Acetyl-5-chloro-2-(3,5-dichlorophenylthio)-indole

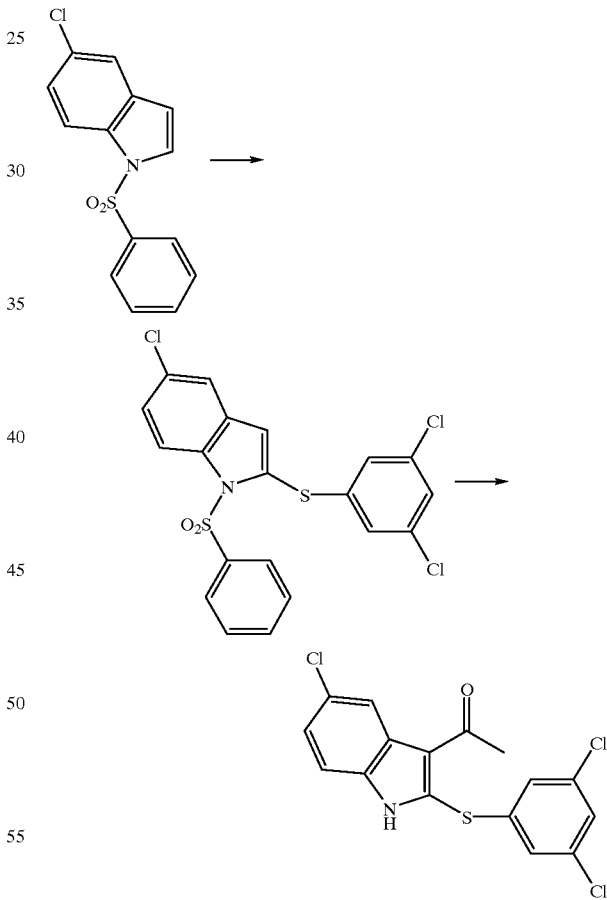

(1) According to the literature described in Reference example 6 (1), 1-benzenesulfonyl-5-chloroindole was reacted with 3,5-dichlorophenyl disulfide to give 1-benzenesulfonyl-5-chloro-2-(3,5-dichlorophenylthio)-indole. Yield: 71%. m.p.: 121–122° C.

NMR(CDCl$_3$) δ: 6.68(1H, s), 6.97(2H, d, J=1.2Hz), 7.19 (1H, t, J=1.2 Hz), 7.35–7.57(4H, m), 7.85–7.88(2H, m), 8.26(2H, d, J=9.0 Hz).

(2) In a manner similar to that described in Reference example 2 (3), the above-mentioned compound was reacted with Ac$_2$O/AlCl$_3$ and deprotected with lithium hydroxide to give the titled compound. Yield: 27%. m.p.: 180–185° C.

NMR(CDCl$_3$) δ: 2.69(3H, s), 7.20–7.22(2H, m), 7.41(1H, d, J=1.8 Hz), 7.45(1H, t, J=1.8 Hz), 8.01(1H, brs), 8.10(1H, brs).

REFERENCE EXAMPLE 9

3-Acetyl-5-chloro-2-benzenesulfonylindole

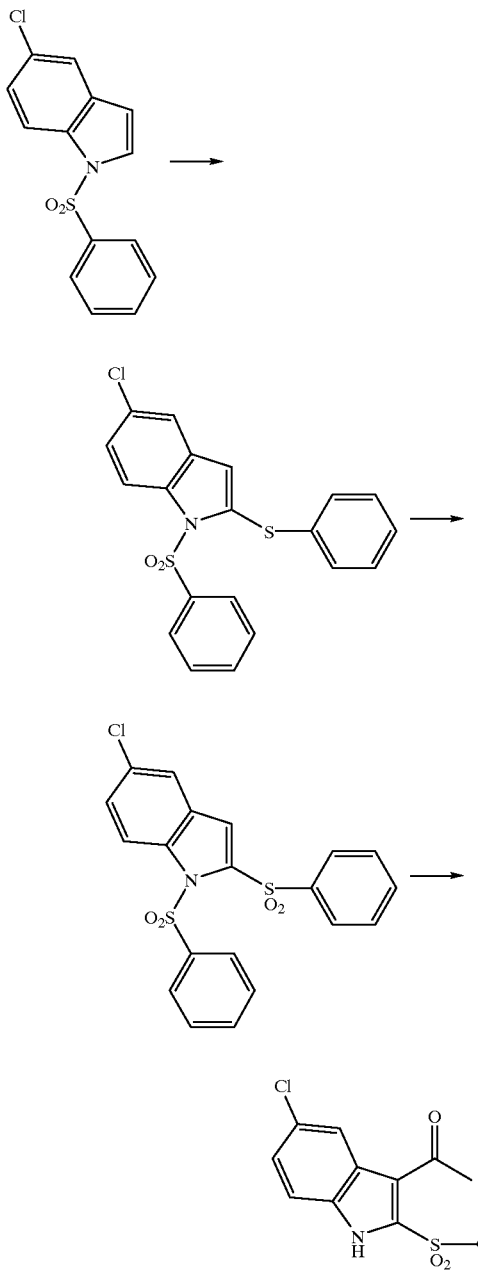

(1) 1-Benzenesulfonyl-5-chloro-2-phenylthio-indole was obtained in a manner similar to that described in Reference example 8 (1). Yield: 92%.

NMR(CDCl$_3$) δ: 6.14(1H, s), 7.22–7.60(10H, m), 7.93–7.98(2H, m), 8.15(1H, d, J=8.8 Hz).

(2) To a solution of 3.65 g (9.12 mmol) of the above-mentioned compound in dichloromethane (50 ml) was added 5.19 g (27.4 mmol) of m-chloroperbenzoic acid under ice-cooling. After stirring for 18 hours at room temperature, the reaction mixture was diluted with ethyl acetate, and then washed with aqueous sodium bicarbonate and water. The solvent was dried and concentrated. The obtained crystal was washed with diisopropyl ether to give 1-benzenesulfonyl-5-chloro-2-phenylsulfonylindole. Subsequently, the compound was deprotected with lithium hydroxide to give 5-chloro-2-phenylsulfonylindole. Yield: 86%. m.p.: 137–138° C.

NMR(CDCl$_3$) δ: 7.12(1H, d, J=3.3 Hz), 7.26–7.65(6H, m), 7.98–8.03(2H, m), 9.23(1H, brs).

(3) To a suspension of 2.0 g (15 mmol) of aluminum chloride and 1.18 g (15 mmol) of acetylchloride in carbon disulfide (21 ml) was added dropwise at room temperature, a solution of 0.87 g (3 mmol) of the above-mentioned compound in dichloromethane (7 ml). After stirring for 1.5 hours, the titled compound was obtained by the work-up described in Reference example 2 (3). Yield: 85%.

NMR(CDCl$_3$) δ: 2.64(3H, s), 7.40(1H, dd, J=8.7 Hz, 1.8 Hz), 7.48–7.67(4H, m), 7.99(1H, d, J=1.8 Hz), 8.06–8.10 (2H, m), 10.1(1H, brs).

The compounds of Example 1–22 were prepared in accordance with reaction route shown below.

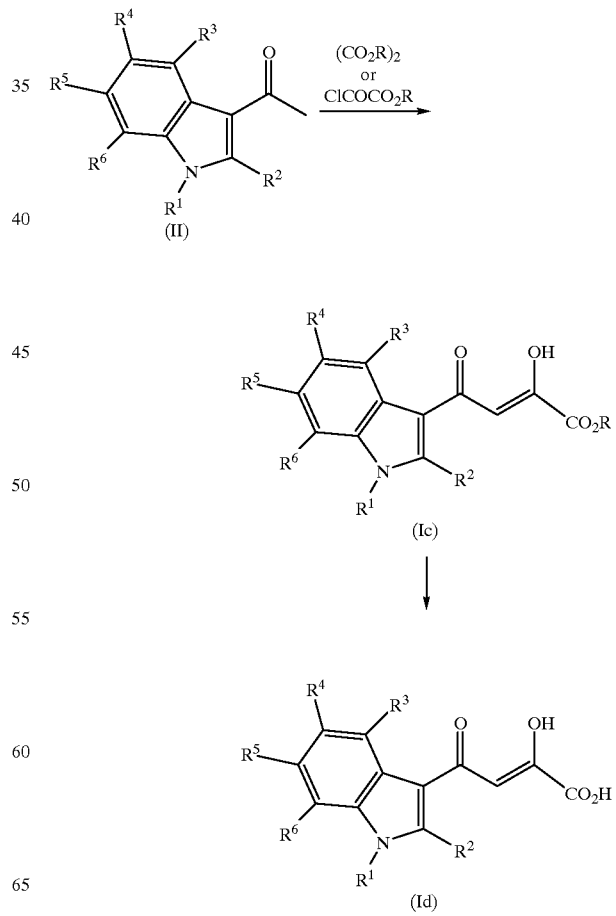

EXAMPLE 1

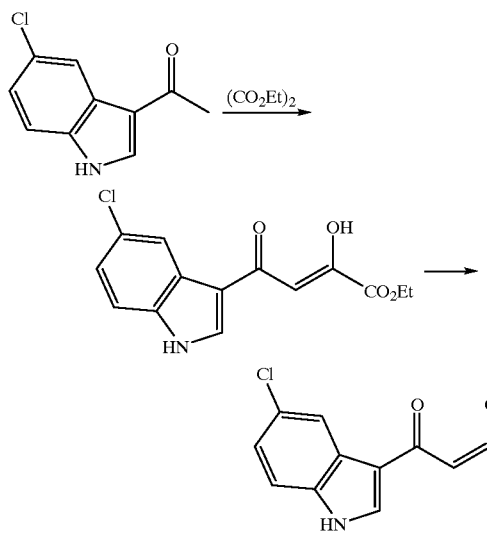

(1) 4-(5-Chloroindol-3-yl)-2-hydroxy-4-oxo-2-butenoic acid ethyl ester

In 100 ml of EtOH was dissolved 2.99 g (126 mmol) of sodium under heating. The EtOH was evaporated under reduced pressure and the residue was suspended in THF (200 ml). The THF was evaporated. To the suspension of the residue in THF (124 ml) was added 18.1 g (124 mmol) of diethyl oxalate. Subsequently, to the above suspension was added at room temperature, 12 g (62 mmol) of 3-acetyl-5-chloroindole. After stirring for 3 hours, the mixture was stirred at 50° C. for additional 16 hours. The solvent was removed under reduced pressure. The resulting residue was washed with ether, and added to 1N hydrochloric acid (120 ml). The precipitated crystal was collected by filtration, and washed with water and ethyl acetate. Then the crystal was purified by recrystallization from dioxane and dried at 80° C. under reduced pressure to give 14.7 g of the titled compound. Yield: 81%.

m.p.: 219–225° C. (decomposition) NMR($d_6$-DMSO) δ:1.32(3H, t, J=7.2 Hz), 4.31(2H, q, J=7.2 Hz), 7.03(1H, s),7.30(1H, dd, J=8.4 Hz, 2.1 Hz), 7.54(1H, d, J=8.4 Hz), 8.21(1H, d, J=2.1 Hz), 8.83(1H, s), 12.6(1H, s). Elemental Analysis for $C_{14}H_{12}ClNO_4$ Calcd. (%):C,57.25; H,4.12; N,4.77; Cl,12.07. Found. (%):C,57.14; H,4.20; N,4.97; Cl,12.01.

(2) 4-(5-Chloroindol-3-yl)-2-hydroxy-4-oxo-2-butenoic acid

To a suspension of 300 mg (1.02 mmol) of the above-obtained ester in dioxane (30 ml) was added 1N hydrochloric acid (3 ml). After the mixture was refluxed for 4 hours, the solvent was removed under reduced pressure. The residue was diluted with water, and the precipitated crystal was collected by filtration. The crystal was washed with water and dioxane, and then dried to give 230 mg of the titled compound as a yellow crystal. Yield: 80%.

m.p.: 220–225° C. (decomposition) NMR($d_6$-DMSO) δ: 7.00(1H, s),7.29(1H, dd, J=8.7 Hz, 2.4 Hz), 7.53(1H, d, J=8.7 Hz), 8.21(1H, d, J=2.4 Hz), 8.77(1H, d, J=3.6 Hz), 12.5(1H, brm), 13.6(1H, brs). Elemental Analysis for $C_{14}H_{12}ClNO_4$ Calcd. (%):C,57.25; H,4.12; N,4.77; Cl,12.07. Found. (%):C,57.14; H,4.20; N,4.97; Cl,12.01.

EXAMPLE 2–22

The other ester derivatives (Ic) were prepared in accordance with Example 1 (1), and the corresponding carboxylic acid derivatives (Id) were prepared in accordance with the above (2). The structures and physical properties of the compounds in example 2–22 are shown in Table 1.

The compounds of Example 23–59 were prepared in accordance with the following route.

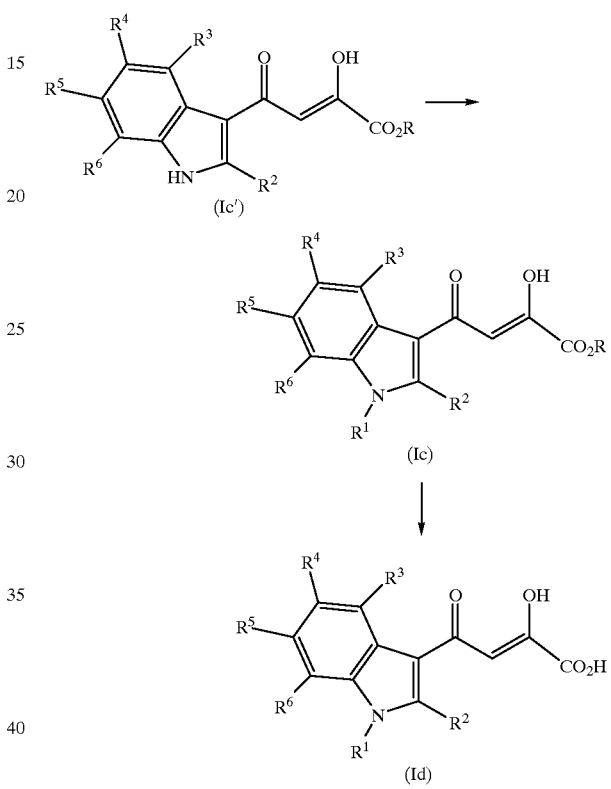

EXAMPLE 23

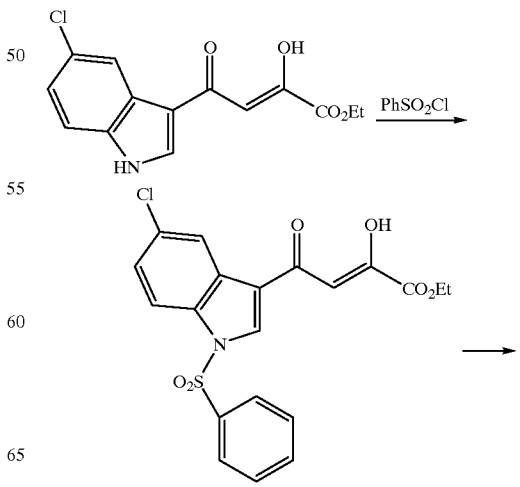

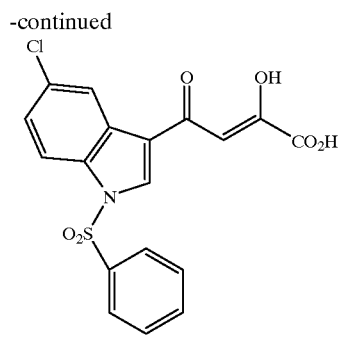

(1) 4-(1-Benzenesulfonyl-5-chloroindol-3-yl)-2-hydroxy-4-oxo-2-butenoic acid ethyl ester To a suspension of 0.88 g (22 mmol) of sodium hydride (60% dispersion in mineral oil) in THF (50 ml) was added under ice-cooling, 2.94 g (10 mmol) of 4-(5-chloroindol-3-yl)-2-hydroxy-4-oxo-2-butenoic acid ethyl ester prepared in Example 1 (1). After stirring for 15 min at room temperature, to the mixture was added dropwise a solution of 2.12 g (12 mmol) of benzenesulfonyl chloride in THF (20 ml). After stirring for 2 hours at room temperature, to the mixture was added DMF (8 ml). After stirring for additional 30 min, the reaction mixture was poured into ice-water containing 1N hydrochloric acid, and extracted with ethyl acetate. The organic layer was washed with water and saturated brine, and then dried. The solvent was concentrated and the residue was crystallized from ether to give crude crystal, which was washed with ether to give 3.75 g of the titled compound. Yield: 87%. Subsequent recrystallization from ethyl acetate afforded the pure ester, melted at. 156–157° C.

NMR($d_6$-DMSO) δ: 1.45(3H, t, J=7.4 Hz), 4.44(2H, q, J=7.4 Hz), 6.89(1H, s),7.38(1H, dd, J=9.0 Hz, 2.4 Hz), 7.50–7.70(3H, m), 7.88–7.99(3H, m), 8.35(1H, s), 8.36(1H, d, J=2.4 Hz), 14.7(1H, brs). Elemental Analysis for $C_{20}H_{16}ClNO_6S$ $0.2H_2O$ Calcd. (%):C,54.91; H,3.78; N,3.20; Cl,8.10, S,7.33. Found. (%):C,54.83; H,3.78; N,3.16; Cl,8.13. S,7.42.

(2) 4-(1-Benzenesulfonyl-5-chloroindol-3-yl)-2-hydroxy-4-oxo-2-butenoic acid

To a suspension of 0.8 g (1.97 mmol) of the ester obtained in the above (1) in dioxane (40 ml) was added 1N hydrochloric acid (8 ml). After the mixture was refluxed for 4 hours, the solvent was removed under reduced pressure. The residue was diluted with water and extracted with ethyl acetate. The organic layer was washed with water and saturated brine, and then dried, The solvent was concentrated and the resulting crystal was purified by recrystallization from ethyl acetate to give 0.6 g the titled compound.

Yield: 80%. m.p.: 210–218° C. (decomposition) NMR ($d_6$-DMSO) δ:7.29(1H, s),7.51(1H, dd, J=8.7 Hz, 2.4 Hz), 7.65–7.82(3H, m), 8.03(1H, d, J=8.7 Hz), 8.20–8.25(3H, m), 9.33(1H, s), 12.0–14.0(1H, brs). Elemental Analysis for $C_{18}H_{12}ClNO_6S$ Calcd. (%):C,53.28; H,2.98; N,3.45; Cl,8.74, S,7.90. Found. (%):C,53.33; H,3.06; N,3.40; Cl,8.56. S,7.85.

EXAMPLE 24–59

The other ester derivatives (Ic) were prepared in accordance with Example 23 (1), and the corresponding carboxylic acid derivatives (Id) were prepared in accordance with the above (2). The substituents and the physical properties of each compound are shown in Table 2–3. The NMR data of the above-mentioned compounds are shown in Table 4, and the elemental analysis data thereof are shown in Table 5.

TABLE 1

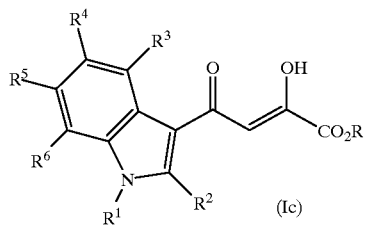 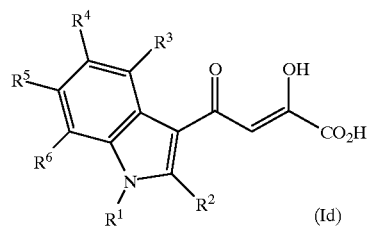

| Example No. | $R^1$ | $R^2$ | $R^3$ | $R^4$ | $R^5$ | $R^6$ | R | Recrystallization/M.p. (° C.) (Ic) | | (Id) | |
|---|---|---|---|---|---|---|---|---|---|---|---|
| 2 | H | H | H | H | H | H | Et | MeOH-Hex | >300 | EtOAc | 202–209 |
| 3 | H | H | Cl | H | H | H | Me | | powder | EtOAc | 185–187 |
| 4 | H | H | H | F | H | H | Me | MEK | 202–204 | EtOAc | 202–204 |
| 5 | H | H | H | Br | H | H | Et | EtOH | 238–246 | dioxane | 236–237 |
| 6 | H | H | H | H | Cl | H | Me | EtOAc | 185–190 | MEK | 240–245 |
| 7 | H | H | H | H | H | Cl | Me | EtOAc | 190–191 | MeCN | 203–205 |
| 8 | H | H | H | OMe | H | H | Me | EtOAc | 202–206 | EtOAc | 209–211 |
| 9 | H | H | H | OBn | H | H | Et | | powder | EtOAc | 211–212 |
| 10 | —(CH$_2$)$_3$Ph | H | H | Cl | H | H | Me | EtOAc | 214–217 | EtOH | 95–100 |
| 11 | —Ph(4-F) | H | H | H | H | H | Me | EtOAc | 204–206 | EtOAc | 194–195 |
| 12 | 4-picolyl | H | H | Cl | H | H | Me | EtOAc | 208–215 | EtOH—H$_2$O | 230–232 |
| 13 | Bn | H | H | NO$_2$ | H | H | Me | MEK | 210–211 | EtOAc | 201–210 |
| 14 | Bn | H | H | H | —O(CH$_2$)$_2$Ph | H | Me | EtOAc—Et$_2$O | 125–128 | EtOAc | 193–196 |
| 15 | Bn | H | H | H | —OSO$_2$Ph | H | Me | EtOAc | 186–187 | EtOAc | 201–203 |
| 16 | H | Ph(2-Cl) | H | H | H | H | Me | EtOAc—Hex | 198–202 | EtOAc—Hex | 180–182 |
| 17 | H | Ph(3-Cl) | H | H | H | H | Me | EtOAc—Hex | 202–204 | EtOAc—Hex | 109–110 |
| 18 | H | Ph(4-F) | H | H | H | H | Me | EtOAc—Hex | 202–204 | EtOAc—Hex | 195–197 |
| 19 | H | Ph(4-Cl) | H | H | H | H | Me | EtOAc—Hex | 220–222 | EtOAc—Hex | 187–190 |
| 20 | H | Ph(4-OMe) | H | H | H | H | Me | EtOAc—Hex | 203–205 | EtOAc—Hex | 172–174 |

TABLE 1-continued (Ic) structure with R groups and CO₂R; (Id) structure with R groups and CO₂H

| Example No. | R¹ | R² | R³ | R⁴ | R⁵ | R⁶ | R | Recrystallization (Ic) | M.p. (°C) (Ic) | Recrystallization (Id) | M.p. (°C) (Id) |
|---|---|---|---|---|---|---|---|---|---|---|---|
| 21 | H | Ph(3-NMe₂) | H | H | H | H | Me | EtOAc—Hex | 162–165 | EtOAc—Hex | 150–155 |
| 22 | Me | Ph(3-Cl) | H | H | H | H | Me | EtOAc—Hex | 151–152 | EtOAc—Hex | 167–168 |

TABLE 2

| Example No. | R¹ | R² | R³ | R⁴ | R⁵ | R⁶ | R | Recrystallization (Ic) | M.p. (°C) (Ic) | Recrystallization (Id) | M.p. (°C) (Id) |
|---|---|---|---|---|---|---|---|---|---|---|---|
| 24 | —SO₂Ph | H | H | F | H | H | Me | | powder | EtOAc | 186–196 |
| 25 | —SO₂Ph | H | H | Br | H | H | Me | EtOAc | 212–213 | EtOAc | 212–217 |
| 26 | —SO₂Ph | H | H | H | Cl | H | Me | Et₂O | 176–178 | EtOAc | 222–226 |
| 27 | —SO₂Ph | H | H | OBn | H | H | Et | | oil | EtOAc | 210–214 |
| 28 | —SO₂Ph(4-F) | H | H | Cl | H | H | Et | EtOAc | 169–170 | EtOH—EtOAc | 229–230 |
| 29 | —SO₂Ph(2-F) | H | H | Cl | H | H | Et | EtOAc—Et₂O | 134–135 | EtOAc | 231–232 |
| 30 | —SO₂Ph(2,4-F) | H | H | Cl | H | H | Et | EtOAc—Et₂O | 179–181 | EtOH—EtOAc | 228–229 |
| 31 | —SO₂Ph(4-Cl) | H | H | Cl | H | H | Et | EtOAc | 169–170 | EtOH—EtOAc | 214 |
| 32 | —SO₂Ph(2,5-Cl) | H | H | Cl | H | H | Et | EtOAc—Et₂O | 179–180 | EtOH | 243–244 |
| 33 | —SO₂Ph(2-Br) | H | H | Cl | H | H | Et | | power | EtOH—EtOAc | 222–223 |
| 34 | —SO₂Ph(3-NO₂) | H | H | Cl | H | H | Et | EtOAc | 185–186 | EtOH—EtOAc | 257–258 |
| 35 (Ic) | —SO₂Ph(4-NHAc) | H | H | Cl | H | H | Et | EtOH | 125–126 | | |
| (Id) | —SO₂Ph(4-NH₂) | H | H | Cl | H | H | | | | EtOH—EtOAc | >300 |
| 36 | —SO₂Ph(4-Bn) | H | H | Cl | H | H | Et | EtOH—EtOAc | 120–121 | EtOH—EtOAc | 169–170 |
| 37 | —SO₂Ph(4-OMe) | H | H | Cl | H | H | Et | Et₂O | 157–158 | EtOAc—Et₂O | 194–195 |
| 38 | —SO₂Ph(2-CO₂Me) | H | H | Cl | H | H | Et | EtOAc—Et₂O | 167–168 | Et₂O | 184–185 |
| 39 | —SO₂Ph(2,4,6-Me) | H | H | Cl | H | H | Et | EtOAc—Et₂O | 105–106 | Et₂O | 264–267 |

TABLE 3

| Example No. | R¹ | R² | R³ | R⁴ | R⁵ | R⁶ | R | Recrystallization (Ic) | M.p. (°C) (Ic) | Recrystallization (Id) | M.p. (°C) (Id) |
|---|---|---|---|---|---|---|---|---|---|---|---|
| 40 | —SO₂iPr | H | H | Cl | H | H | Et | | oil | EtOAc—Et₂O | 183–184 |
| 41 | —SO₂NMe₂ | H | H | Cl | H | H | Et | EtOAc | 162–163 | EtOAc—Et₂O | 209–210 |

TABLE 3-continued

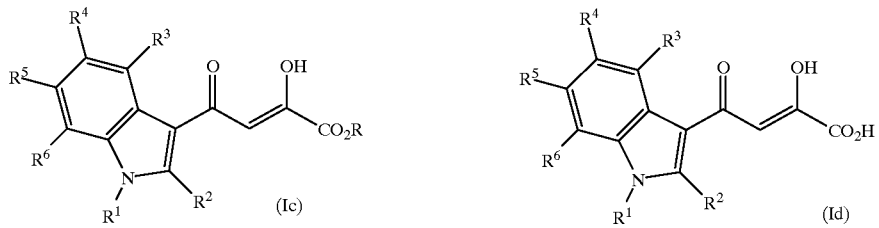

| Example No. | R¹ | R² | R³ | R⁴ | R⁵ | R⁶ | R | Recrystallization/M.p. (° C.) (Ic) | | (Id) | |
|---|---|---|---|---|---|---|---|---|---|---|---|
| 42 | N-morpholino sulfonyl | H | H | Cl | H | H | Et | EtOAc | 202–205 | EtOAc | 205–208 |
| 43 | Me | H | H | H | H | H | Et | | powder | EtOH | 180–185 |
| 44 | Me | H | Cl | H | H | H | Me | | powder | EtOAc | 176–178 |
| 45 | Me | H | H | Cl | H | H | Me | | powder | EtOH | 178–183 |
| 46 | Bu | H | H | Br | H | H | Me | EtOAc | 155–157 | EtOAc | 168–173 |
| 47 | —CH₂Ph | H | H | Cl | H | H | Et | EtOAc | 176–177 | EtOAc | 183–185 |
| 48 | —CH₂Ph(4-N₃) | H | H | Br | H | H | Me | | oil | EtOAc | 185–195 |
| 49 | 2-naphthylmethyl | H | H | Cl | H | H | Et | EtOAc | 183–184 | EtOAc | 203–209 |
| 50 | —CH₂Ph(4-Ph) | H | H | Cl | H | H | Et | EtOAc | 145–150 | EtOAc | 190–195 |
| 51 | —CH₂Ph(2-Ph) | H | H | Cl | H | H | Me | EtOAc | 143–145 | EtOAc | 190–195 |
| 52 | cyclopropylmethyl | H | H | Cl | H | H | Et | EtOH—EtOAc | 177–179 | EtOAc—Et₂O | 194–195 |
| 53 | —CH₂Ph(3-CO₂Me) | H | H | Cl | H | H | Et | EtOAc—Et₂O | 179–180 | Et₂O | 196–197 |
| 54 | —CH₂Ph(4-CO₂Me) | H | H | Cl | H | H | Et | | powder | EtOAc | 199–200 |
| 55 | 2-methoxycarbonyl-5-thienylmethyl | H | H | Cl | H | H | Et | EtOAc—Et₂O | 166–167 | EtOAc—Et₂O | 178–179 |
| 56 | —CONHPh | H | H | Cl | H | H | Et | Et₂O | 193–195 | EtOAc | 203–205 |
| 57 | —CH₂Ph | Ph(2-Cl) | H | H | H | H | Me | EtOAc—Hex | 169–170 | EtOAc—Hex | 185–188 |
| 58 | —SO₂Ph | Ph(4-F) | H | H | H | H | Me | | powder | EtOAc—Hex | 180–185 |
| 59 | —CH₂Ph | —CH₂Ph | H | H | H | H | Me | EtOAc—Hex | 125–127 | EtOAc—Hex | 175–180 |

TABLE 4-1

| Example | ester derivative (I c) | carboxylic acid (I d) |
|---|---|---|
| 2 | | (d₆-DMSO)δ: 7.03(1H, s), 7.10–7.70(3H, m), 8.10–8.50(2H, m), 8.70(1H, d, J=3.0Hz). |
| 3 | (CDCL₃)δ: 3.93(3H, s), 7.00(1H, s), 7.19–7.39(3H, m), 7.95(1H, d, J=2.4Hz), 9.92(1H, brs). | (d₆-DMSO)δ: 7.00(1H, s), 7.25–7.28(2H, m), 7.42–7.52(1H, m), 8.62(1H, d, J=3.0Hz). |
| 4 | (d₆-DMSO)δ: 3.95(3H, s), 7.03(1H, s), 7.14(1H, dd, J=8.8Hz, 2.8Hz), 7.53(1H, dd, J=9.0Hz, 4.4Hz), 7.89(1H, dd, J=10Hz, 2.6Hz), 8.81(1H, s), 12.4(1H, brs). | (d₆-DMSO)δ: 7.00(1H, s), 7.13(1H, dt, J=8.8Hz, 2.8Hz), 7.52(1H, dd, J=8.7Hz, 4.8Hz), 7.89(1H, dd, J=9.6Hz, 2.4Hz), 8.78(1H, s), 12.5(1H, s), 13.6(1H, brs). |
| 5 | (d₆-DMSO)δ: 1.30(3H, t, J=5.9Hz), 4.28(2H, q, J=5.9Hz), 6.90(1H, s), 7.25–7.60(2H, m), 8.30–8.40(1H, m), 8.70–8.80(1H, m). | (d₆-DMSO)δ: 7.01(1H, s), 7.41(1H, dd, J=8.8Hz, 2.1Hz), 7.49(1H, d, ) J=8.8Hz), 8.37(1H, d, J=2.1Hz), 8.77(1H, d, J=2.7Hz), 12.6(1H, brs), 13.5(1H, brs). |
| 6 | (d₆-DMSO)δ: 3.85(3H, s), 7.05(1H, s), 7.29(1H, dd, J=8.7Hz, 1.8Hz), 7.56(1H, d, J=1.8Hz), 8.21(1H, d, J=8.7Hz), 8.81(1H, s), 12.6(1H, brs). | (d₆-DMSO)δ: 7.01(1H, s), 7.28(1H, dd, J=8.6Hz, 1.8Hz), 7.55(1H, d, J=1.8Hz), 8.21(1H, d, J=8.6Hz), 8.76(1H, d, J=3.2Hz), 12.5(1H, brs). |
| 7 | (CDCL₃)δ: 3.95(3H, s), 6.90(1H, s), 7.25–7.35(2H, m), 8.04(1H, d, J=3.0Hz), 8.29(1H, dd, J=7.4Hz, 1.6Hz), 8.95(1H, brs). | (d₆-DMSO)δ: 7.09(1H, s), 7.22–7.39(2H, m), 8.21(1H, d, J=7.8Hz), 8.80(1H, dd, J=3.2Hz), 12.8(1H, s), 13.9(1H, brs). |
| 8 | (d₆-DMSO)δ: 3.80(3H, s), 3.85(3H, s), 6.90(1H, dd, J=8.8Hz, 2.4Hz), 7.02(1H, s), 7.40(1H, d, J=8.8Hz), 7.73(1H, d, J=2.4Hz), 8.68(1H, d, J=3.2Hz), 12.4(1H, brs). | (d₆-DMSO)δ: 3.81(3H, s), 6.90(1H, dd, J=8.6Hz, 2.2Hz), 6.99(1H, s), 7.40(1H, d, J=8.6Hz), 7.73(1H, d, J=2.2Hz), 8.64(1H, d, J=3.6Hz), 12.3(1H, brs). |
| 9 | (d₆-DMSO)δ: 1.32(3H, t, J=7.4Hz), 4.31(2H, q, J=7.4Hz), 5.14(2H, s), 6.98(1H, d, J=9.0Hz, 2.4Hz), 7.00(1H, s), 7.30–7.54(6H, m), 7.83(1H, d, J=2.4Hz), 8.68(1H, s), 12.3(1H, brs). | (d₆-DMSO)δ: 5.14(2H, s), 6.98(1H, s), 6.99(1H, dd, J=9.0Hz, 2.4Hz), 7.30–7.52(6H, m), 7.84(1H, d, J=2.4Hz), 8.63(1H, d, J=3.0Hz), 12.9(1H, d, J=3.0Hz), 13.7(1H, brs). |
| 10 | (d₆-DMSO)δ: 3.16(2H, t, J=7.8Hz), 3.86(3H, s), 4.53(2H, t, J=7.8Hz), 6.93(1H, s), 7.17–7.34(6H, m), 7.71(1H, d, J=8.6Hz), 8.19(1H, d, J=2.2Hz), 8.81(1H, s). | (d₆-DMSO)δ: 3.16(2H, t, J=7.4Hz), 4.52(2H, t, J=7.4Hz), 6.91(1H, s), 7.18–7.36(6H, m), 7.72(1H, d, J=8.6Hz), 8.21(1H, d, J=2.1Hz), 8.79(1H, s), 13.8(1H, brs). |
| 11 | (d₆-DMSO)δ: 3.85(3H, s), 7.20(1H, s), 7.35–7.55(5H, m), 7.76–7.83(2H, m), 8.33–8.38(1H, m), 9.09(1H, s). | (d₆-DMSO)δ: 7.16(1H, s), 7.36–7.39(2H, m), 7.46–7.52(3H, m), 7.76–7.81(2H, m), 8.35–8.39(1H, m), 9.04(1H, s), 13.8(1H, brs). |
| 12 | (CDCL₃)δ: 3.69(3H, s), 5.56(2H, s), 6.33(1H, s), 7.12–7.20(3H, m), 7.45(1H, d, J=8.8Hz), 8.33(1H, d, J=2.2Hz), 8.37(1H, s), 8.48–8.52(2H, m). | (d₆-DMSO)δ: 5.83(2H, s), 6.97(1H, s), 7.35(1H, dd, J=8.7Hz, 2.1Hz), 7.61–7.66(3H, m), 8.26(1H, d, J=2.1Hz), 8.77(2H, d, J=6.0Hz), 9.05(1H, s). |

TABLE 4-2

| Example | ester derivative (I c) | carboxylic acid (I d) |
|---|---|---|
| 13 | (d₆-DMSO)δ: 3.86(3H, s), 5.62(2H, s), 7.06(1H, s), 7.25–8.20(7H, m), 9.10(1H, d, J=2.1Hz), 9.25(1H, s). | (d₆-DMSO)δ: 5.62(2H, s), 7.06(1H, s), 7.25–8.20(5H, m), 7.89(1H, d, J=9.0Hz), 8.17(1H, dd, J=9.0Hz, 2.4Hz), 9.11(1H, d, J=2.4Hz), 9.25(1H, s), 14.0(1H, brs). |
| 14 | (CDCL₃)δ: 3.09(2H, t, J=6.9Hz), 3.92(3H, s), 4.18(2H, t, J=6.9Hz), 5.29(2H, s), 6.76(1H, d, J=1.8Hz), 6.79(1H, s), 6.98(1H, dd, J=8.7Hz, 1.8Hz), 7.14–7.37(10H, m), 7.79(1H, s), 8.26(1H, d, J=8.7Hz). | (d₆-DMSO)δ: 3.04(2H, t, J=6.6Hz), 4.20(2H, t, J=6.6Hz), 5.50(2H, s), 6.90(1H, dd, J=9.0Hz, 2.1Hz), 6.95(1H, s), 7.19(1H, d, J=2.1Hz), 7.21–7.36(10H, m), 8.08(1H, d, J=9.0Hz), 8.83(1H, s). |
| 15 | (CDCL₃)δ: 3.92(3H, s), 5.29(2H, s), 6.78(1H, s), 6.78(1H, dd, J=9.0Hz, 2.1Hz), 7.10–7.80(11H, m), 7.90(1H, s), 8.24(1H, d, J=9.0Hz). | (d₆-DMSO)δ: 5.43(2H, s), 6.95(1H, dd, J=9.0Hz, 2.4Hz), 6.98(1H, s), 7.22–7.80(11H, m), 8.16(1H, d, J=9.0Hz), 9.04(1H, s), 13.8(1H, brs). |
| 16 | (d₆-DMSO)δ: 3.66(3H, s), 6.02(1H, s), 7.26–7.40(2H, m), 7.48–7.80(5H, m), 8.23–8.38(1H, m), 12.7(1H, s). | (d₆-DMSO)δ: 6.05(1H, s), 7.22–7.40(2H, m), 7.42–7.78(5H, m), 8.22–8.34(1H, m), 12.6(1H, s), 13.4(1H, brs). |
| 17 | (d₆-DMSO)δ: 3.70(3H, s), 6.28(1H, s), 7.24–7.38(2H, m, 7.46–7.74(4H, m), 7.81(1H, s), 8.20–8.32(1H, m), 12.7(1H, s). | (d₆-DMSO)δ: 5.95(1H, s), 7.32–7.46(2H, m), 7.52–7.58(1H, m), 7.62–7.80(5H, m), 8.30–8.38(1H, m), 13.4(1H, brs). |
| 18 | (d₆-DMSO)δ: 3.69(3H, s), 6.21(1H, s), 7.24–7.38(2H, m), 7.39–7.58(3H, m), 7.70–7.80(2H, m), 8.21–8.28(1H, m), 12.6(1H, brs). | (d₆-DMSO)δ: 6.23(1H, s), 7.20–7.38(2H, m), 7.38–7.58(3H, m), 7.70–7.80(2H, m), 8.18–8.30(1H, m), 12.5(1H, s), 13.4(1H, brs). |
| 19 | (d₆-DMSO)δ: 3.70(3H, s), 6.24(1H, s), 7.20–7.40(2H, m), 7.42–7.60(1H, m), 7.62–7.80(5H, m), 8.20–8.30(1H, m). | (CDCL₃)δ: 6.64(1H, s), 7.33–7.60(7H, m), 8.24–8.30(1H, m), 8.75(1H, brs) |
| 20 | (d₆-DMSO)δ: 3.68(3H, s), 3.88(3H, s), 6.31(1H, s), 7.16(2H, d, J=8.7Hz), 7.22–7.34(2H, m), 7.45(1H, dd, J=6.5Hz, 2.1Hz), 7.61(2H, d, J=8.7Hz), 8.23(1H, dd, J=6.5Hz, 2.1Hz), 12.5(1H, s) | (d₆-DMSO)δ: 3.85(3H, s), 6.32(1H, s), 7.14(2H, d, J=7.8Hz), 7.20–7.32(2H, m), 7.42–7.50(1H, m), 7.61(2H, d, J=7.8Hz), 8.22(1H, dd, J=7.8Hz, 1.2Hz), 12.4(1H, s), 13.4(1H, brs). |
| 21 | (CDCL₃)δ: 3.02(6H, S), 3.78(3H, s), 6.54(1H, s), 6.90–7.06(3H, brm), 7.30–7.48(4H, m), 8.32–8.44(1H, m, 8.76(1H, brs). | (d₆-DMSO)δ(HCl free): 3.20(6H, S), 6.60(1H, s), 7.13(1H, d, J=7.8Hz), 7.29(1H, t, J=8.1Hz), 7.45(1H, t, J=8.1Hz), 7.57(1H, s), 7.65(2H, t, J=8.1Hz), 8.60(1H, d, J=7.8Hz), 12.5(1H, s), 13.8(1H, brs). |
| 22 | (d₆-DMSO)δ: 3.60(3H, s), 3.66(3H, s), 5.90(1H, s), 7.30–7.48(3H, m), 7.56(1H, dt, J=11.1Hz, 1.6Hz), 7.62–7.82(3H, m), 8.30–8.40(1H, m). | (d₆-DMSO)δ: 3.60(3H, s), 5.94(1H, s), 7.36(1H, td, J=7.2Hz, 1.5Hz), 7.41(1H, td, J=7.2Hz, 1.5Hz), 7.56(1H, dt, J=2.7Hz, 1.5Hz), 7.60–7.75(4H, m), 8.33(1H, dd, J=7.2Hz, 1.5Hz), 13.4(1H, brs). |
| 24 | (CDCL₃)δ: 3.75(3H, s), 6.75(1H, s), 7.38–8.00(8H, m), 8.26(1H, s). | (d₆-DMSO)δ: 7.30(1H, s), 7.33–8.25(8H, m), 9.34(1H, s), 13.8(1H, brd). |
| 25 | (CDCL₃)δ: 3.98(3H, s), 6.89(1H, s), 7.50–7.68(4H, m), 7.85(1H, d, J=9.0Hz), 7.94–7.98(2H, m), 8.32(1H, s), 8.51(1H, t, J=1.8Hz). | (d₆-DMSO)δ: 7.29(1H, s), 7.60–7.83(4H, m), 7.98(1H, d, J=9.0Hz), 8.19–8.23(2H, m), 8.40(1H, d, J=2.1Hz), 9.31(1H, s), 13.8(1H, brs). |

TABLE 4-3

| Example | ester derivative (I c) | carboxylic acid (I d) |
|---|---|---|
| 26 | (CDCL₃)δ: 3.97(3H, s), 6.90(1H, s), 7.36(1H, dd, J=8, 7Hz, 1.8Hz), 7.53–7.70(3H, m), 7.96–8.00(3H, m), 8.25(1H, d, J=8.1Hz), 8.31(1H, s), 14.7(1H, brs). | (d₆-DMSO)δ: 7.29(1H, s), 7.49(1H, dd, J=8.4Hz, 2.1Hz), 7.66–7.72(4H, m), 8.01(1H, d, J=2.1Hz), 8.26(2H, d, J=8.7Hz), 9.31(1H, s), 14.0(1H, brs). |
| 27 | (d₆-DMSO)δ: 1.35(3H, t, J=7.4Hz), 4.35(2H, q, J=7.4Hz), 5.14(2H, s), 7.13–8.20(14H, m), 9.23(1H, s). | (d₆-DMSO)δ: 5.14(2H, s), 7.15(1H, dd, J=9.0Hz, 2.4Hz), 7.27(1H, s), 7.30–7.80(8H, m), 7.85(1H, d, J=2.4Hz), 7.91(1H, d, J=9.0Hz), 8.16–8.22(2H, m), 9.20(1H, s), 13.8(1H, brs). |
| 28 | (d₆-DMSO)δ: 1.34(3H, t, J=9.0Hz), 4.36(2H, q, J=9.0Hz), 7.30(1H, s), 7.45–7.60(3H, m), 8.04(1H, d, J=9.0Hz), 8.25(1H, d, J=3.0Hz), 8.32(2H, dd, J=12.0Hz, 7.2Hz), 9.34(1H, s). | (d₆-DMSO)δ: 7.27(1H, s), 7.52(1H, d, J=8.7Hz), 7.55(1H, d, J=8.7Hz), 8.05(1H, d, J=9.0Hz), 8.25(1H, d, J=2.1Hz), 8.33(2H, q, J=4.5Hz), 9.31(1H, s), 14.0(1H, brs). |
| 29 | (d₆-DMSO)δ: 1.34(3H, t, J=6.9Hz), 4.34(2H, q, J=6.9Hz), 7.35(1H, s), 7.40–7.60(3H, m), 7.80–7.95(2H, m), 8.2–8.35(2H, m), 8.26(2H, d, J=1.8Hz), 9.36(1H, s). | (d₆-DMSO)δ: 7.32(1H, s), 7.44–7.60(3H, m), 7.80–7.95(1H, m), 7.87(1H, J=9.3Hz), 9.32(1H, d, J=1.8Hz). |
| 30 | (d₆-DMSO)δ: 1.34(3H, t, J=6.9Hz), 4.34(2H, q, J=6.9Hz), 7.34(1H, s), 7.72(1H, dd, J=9.0Hz, 2.4Hz), 7.51(1H, dd, J=8.7Hz, 2.1Hz), 7.64(1H, dt, J=9.0Hz, 2.4Hz), 7.88(1H, d, J=8.4Hz), 8.29(1H, d, J=2.1Hz), 8.40(1H, m), 9.34(1H, s). | (d_f-DMSO)δ: 7.30(1H, s), 7.45(1H, d, J=9.0Hz), 7.51(1H, dd, J=9.0Hz, 2.4Hz), 7.64(1H, m), 7.89(1H, d, J=9.0Hz), 8.29(1H, d, J=2.1Hz), 8.40(1H, m), 9.31(1H, s), 13.6(1H, brs) |
| 31 | (d₆-DMSO)δ: 1.34(3H, t, J=6.9Hz), 4.36(2H, q, J=6.9Hz), 7.30(1H, s), 7.52(1H, dd, J=9.0, 2.4Hz), 7.76(2H, d, J=9.0Hz), 8.03(1H, d, J=9.0Hz), 8.23(2H, d, J=9.0Hz), 8.25(1H, d, J=2.1Hz), 9.34(1H, s). | (d₆-DMSO)δ: 7.27(1H, s), 7.52(1H, dd, J=9.0, 2.1Hz), 7.76(2H, d, J=9.0Hz), 8.03(1H, d, J=9.0Hz), 8.24(2H, d, J=9.0Hz), 8.25(1H, d, J=2.1Hz), 9.31(1H, s), 14.0(1H, s). |
| 32 | (d₆-DMSO)δ: 1.33(3H, t, J=6.9Hz), 4.34(2H, q, J=6.9Hz), 7.35(1H, s), 7.49(1H, dd, J=8.7Hz, 2.4Hz), 7.75(1H, d, J=8.7Hz), 7.85(1H, d, J=8.7Hz), 7.92(1H, dd, J=8.7Hz, 2.7Hz), 8.30(1H, d, J=2.4Hz), 8.52(1H, d, J=2.7Hz), 9.40(1H, s) | (d₆-DMSO)δ: 7.30(1H, d, J=10Hz), 7.49(1H, dd, J=9.0Hz, 1.6Hz), 7.75(1H, d, J=8.4Hz), 7.85(1H, d, J=9.0Hz), 7.92(1H, dd, J=8.4Hz, 2.7Hz), 8.30(1H, d, J=2.1Hz), 8.52(1H, d, J=2.7Hz), 9.36(1H, d, J=10Hz), 14.0(1H, brs). |
| 33 | (d₆-DMSO)δ: 1.33(3H, t, J=6.9Hz), 4.34(2H, q. J=6.9Hz), 7.35(1H, s), 7.45(1H, dd, J=9.0Hz, 2.1Hz), 7.66(1H, d, J=9.0Hz), 7.74(2H, brt, J=8.7Hz), 7.91(1H, dd, J=7.8Hz, 1.8Hz), 8.31(1H, d, J=1.8Hz), 8.41(1H, dd, J=7.8Hz, 1.8Hz), 9.38(1H, s). | (d₆-DMSO)δ: 7.31(1H, s), 7.44(1H, dd, J=9.0Hz, 2.1Hz), 7.65(1H, d, J=9.0Hz), 7.73(2H, td, J=8.7Hz, 2.1Hz), 7.90(1H, dd, J=7.8Hz, 1.8Hz), 8.31(1H, d, J=2.1Hz), 8.42(1H, dd, J=7.8Hz, 2.1Hz), 9.33(1H, s), 14.0(1H, brs). |
| 34 | (d₆-DMSO)δ: 1.34(3H, t, J=7.2Hz), 4.36(2H, q, J=7.2Hz), 7.30(1H, s), 7.54(1H, dd, J=9.0, 2.1Hz), 7.97(1H, t, J=8.4Hz), 8.10(1H, d, J=8.4Hz), 8.25(1H, d, J=2.1Hz), 8.57(1H, dd, J=8.4Hz, 2.1Hz), 8.66(1H, d, J=8.4Hz), 8.89(1H, d, J=2.1Hz), 9.45(1H, s). | (d₆-DMSO)δ: 7.28(1H, s), 7.54(1H, dd, J=9.0, 2.1Hz), 7.96(1H, t, J=7.8Hz), 8.11(1H, d, J=9.0Hz), 8.25(1H, d, J=2.1Hz), 8.57(1H, dd, J=7.8Hz, 2.1Hz), 8.66(1H, dd, J=7.8Hz, 2.1Hz), 8.91(1H, d, J=2.1Hz), 9.42(1H, s), 13.8(1H, brs). |

TABLE 4-4

| Example | ester derivative (I c) | carboxylic acid (I d) |
|---|---|---|
| 35 | (d$_6$-DMSO)δ: 1.35(3H, t, J=6.9Hz), 2.06(3H, s), 4.36(2H, q, J=6.9Hz), 7.30(1H, s), 7.50(1H, dd, J=8.7, 2.1Hz), 7.81(2H, d, J=8.7Hz), 8.00(1H, d, J=8.7Hz), 8.13(2H, d, J=8.7Hz), 8.25(1H, d, J=2.1Hz), 9.28(1H, s), 10.5(1H, s) | (d$_6$-DMSO)δ: 6.61(2H, d, J=8.7Hz), 7.26(2H, s), 7.49(1H, dd, J=8.7, 2.1Hz), 7.79(2H, d, J=8.7Hz), 7.98(1H, d, J=8.7Hz), 8.25(1H, d, J=2.1Hz), 9.19(1H, s), 13.6(1H, s). |
| 36 | (d$_6$-DMSO)δ: 1.34(3H, t, J=6.9Hz), 4.02(2H, s), 4.35(2H, q, J=6.9Hz), 7.10–7.38(6H, m), 7.45–7.55(3H, m), 8.01(1H, d, J=8.4Hz), 8.13(2H, d, J=8.4Hz), 8.24(1H, d, J=2.1Hz), 9.32(1H, s). | (d$_6$-DMSO)δ: 4.01(2H, s), 7.10–7.30(6H, m), 7.45–7.55(3H, m), 8.02(1H, d, J=8.4Hz), 8.14(2H, d, J=8.4Hz), 8.24(1H, d, J=2.1Hz), 9.29(1H, s), 13.6(1H, brs), 14.0(1H, brs). |
| 37 | (d$_6$-DMSO)δ: 1.35(3H, t, J=6.9Hz), 3.82(3H, s), 4.35(2H, q, J=6.9Hz), 7.16(1H, d, J=9.0Hz), 7.30(1H, s), 7.50(1H, dd, J=9.0Hz, 2.4Hz), 8.03(1H, d, J=9.0Hz), 8.15(2H, d, J=9.0Hz), 8.25(1H, d, J=2.4Hz), 9.33(1H, s). | (d$_6$-DMSO)δ: 3.82(3H, s), 7.16(1H, d, J=9.0Hz), 7.28(1H, s), 7.50(1H, dd, J=9.0Hz, 2.4Hz), 8.03(1H, d, J=9.3Hz), 8.15(2H, d, J=9.3Hz), 8.25(1H, d, J=2.4Hz), 9.30(1H, s), 13.6(1H, brs). |
| 38 | (d$_6$-DMSO)δ: 1.34(3H, t, J=8.7Hz), 3.94(3H, s), 4.34(2H, q, J=8.7Hz), 7.31(1H, s), 7.50(1H, dd, J=9.0Hz, 2.1Hz), 7.76–7.94(4H, m), 8.15(1H, d, J=8.1Hz), 8.29(1H, d, J=2.1Hz), 9.11(1H, s). | (d$_6$-DMSO)δ: 3.95(3H, s), 7.27(1H, 5), 7.49(1H, dd, J=9.0Hz, 2.4Hz), 7.74–7.94(4H, m), 8.17(1H, d, J=7.5Hz), 8.31(1H, d, J=2.4Hz), 9.13(1H, s). |
| 39 | (d$_6$-DMSO)δ: 1.33(3H, t, J=6.9Hz), 2.29(3H, s), 2.47(6H, s), 4.34(2H, q, J=6.9Hz), 7.20(2H, s), 7.25–7.50(3H, m), 8.31(1H, d, J=1.5Hz), 9.38(1H, s). | (d$_3$-DMSO)δ: 2.29(3H, s), 2.48(6H, s), 7.20(2H, s), 7.32(1H, d, J=9.0Hz), 7.33(1H, s), 7.44(1H, dd, J=9.0Hz, 2.1Hz), 8.32(1H, d, J=2.1Hz), 9.33(1H, s), 13.8(1H, brs) |
| 40 | (d$_6$-DMSO)δ: 1.20–1.35(9H, m), 4.05(1H, sept, J=6.3Hz), 4.34(2H, q, J=7.2Hz), 7.29(1H, s), 7.55(1H, dd, J=8.7Hz, 2.1Hz), 7.95(1H, d, J=8.7Hz), 8.34(1H, d, J=2.1Hz), 9.13(1H, s). | |
| 41 | (d$_6$-DMSO)δ: 1.33(3H, t, J=7.2Hz), 2.91(6H, s), 4.34(2H, q, J=7.2Hz), 7.32(1H, s), 7.51(1H, dd, J=8.7Hz, 2.4Hz), 7.98(1H, d, J=8.7Hz), 8.33(1H, d, J=2.4Hz), 9.17(1H, s). | (d$_6$-DMSO)δ: 7.29(1H, s), 7.51(1H, dd, J=9.0Hz, 2.1Hz), 7.97(1H, d, J=9.0Hz), 8.34(1H, dd, J=9.0Hz, 2.1Hz), 9.14(1H, s), 13.4(1H, brs). |
| 42 | (CDCL$_3$)δ: 1.44(3H, t, J=7.2Hz), 3.24(4H, t, J=5.1Hz), 3.71(4H, t, J=5.1Hz), 4.30(2H, q, J=7.2Hz), 6.86(1H, s), 7.39(1H, dd, J=9.0Hz, 2.1Hz), 7.83(1H, d, J=9.0Hz), 8.17(1H, s), 8.44(1H, d, J=2.1Hz). | (d$_6$-DMSO)δ: 3.25–3.29(4H, m), 3.56–3.58(4H, m), 7.27(1H, s), 7.51(1H, dd, J=8.7Hz, 2.1Hz), 7.95(1H, d, J=8.7Hz), 8.35(1H, d, J=2.1Hz), 9.12(1H, s) |
| 43 | (CDCL$_3$)δ: 1.42(3H, t, J=7.0Hz), 3.90(3H, s), 4.39(2H, q, J=7.0Hz), 6.85(1H, s), 7.35–7.40(3H, m), 7.87(1H, s), 8.36–8.41(1H, m). | (CDCL$_3$)δ: 3.92(3H, s), 6.94(1H, s), 7.38–7.42(3H, m), 7.96(1H, s), 8.26–8.33(1H, m). |
| 44 | (CDCL$_3$)δ: 3.87(3H, s), 3.93(3H, s), 6.97(1H, s), 7.26–7.35(3H, m), 7.82(1H, s). | (CDCL$_3$)δ: 3.88(3H, s), 7.01(1H, s), 7.26–7.35(3H, m), 7.87(1H, s). |

TABLE 4-5

| Example | ester derivative (I c) | carboxylic acid (I d) |
|---|---|---|
| 45 | (d$_6$-DMSO)δ: 3.85(3H, s), 3.90(3H, s), 6.96(1H, s), 7.38(1H, dd, J=8.6Hz, 2.0Hz), 7.66(1H, d, J=8.6Hz), 8.20(1H, d, J=2.0Hz), 8.85(1H, s) | (d$_6$-DMSO)δ: 3.90(3H, s), 6.93(1H, s), 7.38(1H, dd, J=9.0Hz, 2.0Hz), 7.66(1H, d, J=9.0Hz), 8.21(1H, d, J=2.0Hz), 8.82(1H, s), 13.6(1H, brs). |
| 46 | (d$_6$-DMSO)δ: 0.90(3H, t, J=7.2Hz), 1.19–1.30(2H, m), 1.70–1.84(2H, m), 3.86(3H, s), 4.25(2H, t, J=7.2Hz), 7.01(1H, s), 7.47(1H, dd, J=9.0Hz, 2.0Hz), 7.69(1H, s), 8.38(1H, d, J=2.0Hz). | (d$_6$-DMSO)δ: 0.89(3H, t, J=7.6Hz), 1.25(2H, dt, J=7.8Hz, 7.8Hz), 1.80(2H, dd, J=7.6Hz, 7.61Hz), 4.27(2H, t, J=7.2Hz), 6.99(1H, s), 7.47(1H, dd, J=9.0Hz, 2.1Hz), 7.68(1H, d, J=9.0Hz), 8.38(1H, d, J=2.1Hz), 8.87(1H, s). |
| 47 | (CDCL$_3$)δ: 1.41(3H, t, J=7.2Hz), 4.39(2H, q, J=7.2Hz), 5.36(2H, s), 6.78(1H, s), 7.13–7.40(7H, m), 7.89(1H, s), 8.42(1H, s). | (d$_6$-DMSO)δ: 5.54(2H, s), 7.01(1H, s), 7.25–7.40(6H, m), 7.66(1H, d, J=8.4Hz), 7.89(1H, s), 8.22(1H, d, J=2.0Hz), 9.08(1H, s), 13.9(1H, s). |
| 48 | (d$_6$-DMSO)δ: 3.86(3H, s), 5.52(2H, s), 7.01(1H, s), 7.10(2H, d, J=7.8Hz), 7.41(2H, d, J=7.8Hz), 7.44(1H, dd, J=9.0Hz, 1.8Hz), 7.62(1H, d, J=9.0Hz), 8.37(1H, d, J=1.8Hz), 9.07(1H, s). | (d$_6$-DMSO)δ: 5.51(2H, s), 6.99(1H, s), 7.10(2H, d, J=8.4Hz), 7.41(2H, d, J=8.4Hz), 7.44(1H, dd, J=9.0Hz, 1.8Hz), 7.62(1H, d, J=9.0Hz), 8.39(1H, d, J=1.8Hz), 9.00(1H, s) |
| 49 | (CDCL$_3$)δ: 1.39(3H, t, J=7.2Hz), 4.37(2H, q, J=7.2Hz), 5.51(2H, s), 6.78(1H, s), 7.20–7.86(9H, m), 7.94(1H, s), 8.44(1H, d, J=1.8Hz). | (d$_6$-DMSO)δ: 5.71(2H, s), 7.03(1H, s), 7.27–7.94(9H, m), 8.23(1H, d, J=2.2Hz), 9.15(1H, s). |
| 50 | (CDCL$_3$)δ: 1.41(3H, t, J=7.2Hz), 4.38(2H, q, J=7.2Hz), 5.40(2H, s), 6.80(1H, s), 7.20–7.61(11H, m), 7.93(1H, s), 8.44(1H, d, J=1.5Hz). | (d$_6$-DMSO)δ: 5.58(2H, s), 7.02(1H, s), 7.30–7.75(11H, m), 8.24(1H, d, J=2.0Hz), 9.11(1H, s). |
| 51 | (CDCL$_3$)δ: 3.95(3H, s), 5.29(2H, s), 6.62(1H, s), 6.98–7.45(11H, m), 8.18(1H, d, J=1.6Hz). | (d$_6$-DMSO)δ: 5.52(2H, s), 6.79(1H, s), 7.03–7.53(11H, m), 8.18(1H, s), 8.38(1H, d, J=1.6Hz). |
| 52 | (d$_6$-DMSO)δ: 0.30–0.60(4H, m), 1.20–1.40(1H, m), 1.32(3H, t, J=7.2Hz), 4.16(2H, d, J=7.2Hz), 4.32(2H, q, J=7.2Hz), 6.99(1H, s), 7.36(1H, dd, J=8.7Hz, 2.1Hz), 7.77(1H, d, J=8.7Hz), 8.23(1H, d, J=2.1Hz), 8.90(1H, s). | (d$_6$-DMSO)δ: 0.40–0.60(4H, m), 1.25–1.45(1H, m), 4.15(2H, d, J=7.2Hz), 6.99(1H, s), 7.35(1H, dd, J=8.7Hz, 2.1Hz), 7.76(1H, d, J=8.7Hz), 8.23(1H, d, J=2.1Hz), 8.89(1H, s). |
| 53 | (d$_6$-DMSO)δ: 1.32(3H, t, J=7.2Hz), 3.83(3H, s), 4.32(2H, q, J=7.2Hz), 5.65(2H, s), 7.00(1H, s), 7.34(1H, dd, J=8.7Hz, 2.1Hz), 7.51(1H, t, J=7.5Hz), 7.59(1H, d, J=7.5Hz), 7.66(1H, d, J=8.7Hz), 7.89(1H, d, J=7.5Hz), 7.97(1H, s), 8.23(1H, d, J=2.1Hz), 9.11(1H, s). | (d$_6$-DMSO)δ: 3.83(3H, s), 5.63(2H, s), 7.00(1H, s), 7.33(1H, dd, J=8.7Hz, 2.1Hz), 7.51(1H, t, J=7.5Hz), 7.59(1H, brt, J=7.2Hz), 7.67(1H, d, J=8.7Hz), 7.84–8.00(2H, m), 8.23(1H, d, J=2.1Hz), 9.10(1H, s), 13.0(1H, brs). |
| 54 | (d$_6$-DMSO)δ: 1.32(3H, t, J=7.2Hz), 3.83(3H, s), 4.32(2H, q, J=7.2Hz), 5.66(2H, s), 7.00(1H, s), 7.32(1H, dd, J=9.0Hz, 2.1Hz), 7.43(2H, d, J=8.1Hz), 7.60(1H, d, J=9.0Hz), 7.93(2H, d, J=8.1Hz), 8.23(1H, d, J=2.1Hz), 9.08(1H, s). | (d$_6$-DMSO)δ: 3.83(3H, s), 5.64(2H, s), 6.99(1H, s), 7.32(1H, dd, J=9.0Hz, 1.8Hz), 7.44(2H, d, J=8.1Hz), 7.62(1H, d, J=9.0Hz), 7.93(2H, d, J=8.1Hz), 8.23(1H, d, J=1.8Hz), 9.07(1H, s). |

TABLE 4-6

| Example | ester derivative (I c) | carboxylic acid (I d) |
|---|---|---|
| 55 | (d$_6$-DMSO)δ: 1.33(3H, t, J=7.2Hz), 3.76(3H, s), 4.32(2H, q, J=7.2Hz), 5.82(2H, s), 6.98(1H, s), 7.28(1H, d, J=2.4Hz), 7.39(1H, d, J=8.7Hz), 7.68(1H, d, J=2.4Hz), 7.79(1H, d, J=8.7Hz), 8.23(1H, s), 9.06(1H, s). | (d$_6$-DMSO)δ: 3.77(3H, s), 5.81(2H, s), 6.97(1H, s), 7.29(1H, d, J=3.9Hz), 7.33(1H, dd, J=8.7Hz, 2.1Hz), 7.68(1H, d, J=3.9Hz), 7.79(1H, d, J=8.7Hz), 8.23(1H, d, J=2.1Hz), 9.05(1H, s), 13.9(1H, brs). |
| 56 | (d$_6$-DMSO)δ: 1.33(3H, t, J=6.9Hz), 4.35(2H, q, J=6.9Hz), 7.12(1H, s), 7.18–7.70(6H, m), 8.21(1H, d, J=8.7Hz), 8.29(1H, d, J=2.4Hz), 9.34(1H, s) | (d$_6$-DMSO)δ: 7.12(1H, s), 7.17–7.72(6H, m), 8.25(1H, d, J =8.6Hz), 8.31(1H, d, J=2.0Hz), 9.36(1H, s), 13.5(1H, brs). |
| 57 | (d$_6$-DMSO)δ: 3.66(3H, s), 5.34(2H, s), 5.89(1H, s), 6.94(2H, d, J=7.5Hz), 7.23(1H, s), 7.25(1H, d, J=7.8Hz), 7.28–7.40(2H, m), 7.48(2H, dd, J=7.5Hz, 1.5Hz), 7.52–7.68(3H, m), 7.70(1H, d, J= 7.8Hz), 8.34–8.42(1H, m). | (d$_6$-DMSO)δ: 5.35(2H, s), 5.94(1H, s), 6.92(2H, d, J=7.8Hz), 7.23(1H, s), 7.24(1H, d, J=7.8Hz), 7.30–7.40(2H, m), 7.44–7.78(6H, m), 8.38–8.40(1H, m), 13.5(1H, brs). |
| 58 |  | (d$_6$-DMSO)δ: 5.64(1H, s), 7.35(2H, t, J=8.7Hz), 7.45(1H, t, J=7.8Hz), 7.50–7.65(7H, m), 7.68–7.78(1H, m), 8.17(1H, d, J=7.8Hz), 8.23(1H, d, J=8.7Hz), 13.2(1H, brs). |
| 59 | (d$_6$-DMSO)δ: 3.83(3H, s), 4.64(2H, s), 5.51(2H, s), 6.93–7.00(3H, m), 7.05–7.40(10H, m), 7.51(1H, d, J=7.8Hz), 8.03(1H, d, J=7.8Hz). | (d$_6$-DMSO)δ: 4.64(2H, s), 5.48(2H, s), 6.88–6.98(3H, m), 7.12–7.38(10H, m), 7.48(1H, d, J=7.8Hz), 8.00(1H, d, J=7.8Hz) |

TABLE 5-1

| Example | ester derivative (I c) | carboxylic acid (I d) |
|---|---|---|
| 2 |  | for C$_{12}$H$_9$NO$_4$<br>Calcd (%): C, 62.34; H, 3.92; N, 6.06.<br>Found (%): C, 62.02; H, 4.13; N, 5.73. |
| 3 |  | for C$_{12}$H$_8$ClNO$_4$·0.2H$_2$O<br>Calcd (%): C, 53.53; H, 3.14; N, 5.20; Cl, 13.17.<br>Found (%): C, 53.42; H, 3.27; N, 5.43; Cl, 13.10. |
| 4 | for C$_{13}$H$_{10}$FNO$_4$<br>Calcd (%): C, 59.32; H, 3.89; N, 5.32; F, 7.22.<br>Found (%): C, 59.13; H, 3.99; N, 5.34; F, 6.94. | for C$_{12}$H$_8$FNO$_4$<br>Calcd (%): C, 57.84; H, 3.24; N, 5.62; F, 7.62.<br>Found (%): C, 57.94; H, 3.37; N, 5.76; F, 7.63. |
| 5 | for C$_{14}$H$_{12}$BrNO$_4$<br>Calcd (%): C, 49.72; H, 3.58; N, 4.14; Br, 23.63.<br>Found (%): C, 49.79; H, 3.50; N, 4.11; Br, 23.55. | for C$_{12}$H$_4$BrNO$_4$<br>Calcd (%): C, 46.48; H, 2.60; N, 4.52; Br, 25.77.<br>Found (%): C, 46.33; H, 2.68; N, 4.62; Br, 25.46. |
| 6 | for C$_{13}$H$_{10}$ClNO$_4$<br>Calcd (%): C, 55.83; H, 3.60; N, 5.01; Cl, 12.68.<br>Found (%): C, 55.65; H, 3.73; N, 5.02; Cl, 12.39. | for C$_{12}$H$_8$ClNO$_4$<br>Calcd (%): C, 54.26; H, 3.04; N, 5.29; Cl, 13.35.<br>Found (%): C, 54.13; H, 3.17; N, 5.55; Cl, 13.49. |
| 7 | for C$_{13}$H$_{10}$ClNO$_4$<br>Calcd (%): C, 55.83; H, 3.60; N, 5.01; Cl, 12.68.<br>Found (%): C, 55.54; H, 3.75; N, 5.00; Cl, 12.55. | for C$_{12}$H$_8$ClNO$_4$<br>Calcd (%): C, 54.26; H, 3.04; N, 5.29; Cl, 13.35.<br>Found (%): C, 54.01; H, 3.23; N, 5.51; Cl, 13.20. |
| 8 | for C$_{14}$H$_{13}$NO$_5$·0.1H$_2$O<br>Calcd (%): C, 60.69; H, 4.80; N, 5.09.<br>Found (%): C, 60.64; H, 4.88; N, 5.22. | for C$_{13}$H$_{11}$NO$_5$<br>Calcd (%): C, 59.77; H, 4.24; N, 5.36.<br>Found (%): C, 59.97; H, 4.42; N, 5.34. |
| 9 |  | for C$_{19}$H$_{15}$NO$_5$<br>Calcd (%): C, 67.65; H, 4.48; N, 4.15.<br>Found (%): C, 67.44; H, 4.57; N, 4.10. |
| 10 | for C$_{21}$H$_{18}$ClNO$_4$<br>Calcd (%): C, 65.71; H, 4.73; N, 3.65; Cl, 9.24.<br>Found (%): C, 65.83; H, 4.73; N, 3.88; Cl, 9.11. | for C$_{20}$H$_{16}$ClNO$_4$·C$_2$H$_5$OH<br>Calcd (%): C, 63.54; H, 5.33; N, 3.37; Cl, 8.53.<br>Found (%): C, 63.70; H, 5.46; N, 3.61; Cl, 8.50. |
| 11 | for C$_{19}$H$_{14}$FNO$_4$<br>Calcd (%): C, 67.25; H, 4.16; N, 4.13; F, 5.60.<br>Found (%): C, 67.28; H, 4.21; N, 4.13; F, 5.59. | for C$_{18}$H$_{12}$FNO$_4$<br>Calcd (%): C, 66.46; H, 3.72; N, 4.31; F, 5.84.<br>Found (%): C, 66.43; H, 3.79; N, 4.32; F, 5.79. |

TABLE 5-2

| Example | ester derivative (I c) | carboxylic acid (I d) |
|---|---|---|
| 12 | for $C_{19}H_{15}ClN_2O_4 \cdot 0.6H_2O$<br>Calcd (%): C, 59.80; H, 4.28; N, 7.34; Cl, 9.29.<br>Found (%): C, 59.70; H, 3.94; N, 7.70; Cl, 9.19. | for $C_{18}H_{13}ClN_2O_4 \cdot 0.2H_2O$<br>Calcd (%): C, 59.99; H, 3.75; N, 7.77; Cl, 9.84.<br>Found (%): C, 59.85; H, 4.03; N, 7.78; Cl, 9.71. |
| 13 | for $C_{20}H_{16}N_2O_6 \cdot 0.1H_2O$<br>Calcd (%): C, 62.86; H, 4.27; N, 7.33.<br>Found (%): C, 62.73; H, 4.45; N, 7.48. | for $C_{19}H_{14}N_2O_6$<br>Calcd (%): C, 62.30; H, 3.85; N, 7.65.<br>Found (%): C, 62.02; H, 4.03; N, 7.61. |
| 14 | for $C_{28}H_{15}NO_5 \cdot 0.5H_2O$<br>Calcd (%): C, 72.40; H, 5.64; N, 3.05.<br>Found (%): C, 72.27; H, 5.72; N, 3.39. | for $C_{27}H_{23}NO_5$<br>Calcd (%): C, 72.57; H, 5.32; N, 3.13.<br>Found (%): C, 72.50; H, 5.47; N, 3.36. |
| 15 | for $C_{26}H_{21}NO_7S$<br>Calcd (%): C, 63.53; H, 4.31; N, 2.85; S, 6.52.<br>Found (%): C, 63.58; H, 4.42; N, 3.03; S, 6.56. | for $C_{25}H_{19}NO_7S$<br>Calcd (%): C, 62.89; H, 4.01; N, 2.93; S, 6.72.<br>Found (%): C, 62.86; H, 4.05; N, 2.97; S, 6.43. |
| 16 | for $C_{19}H_{14}ClNO_4$<br>Calcd (%): C, 64.14; H, 3.97; N, 3.94; Cl, 9.96.<br>Found (%): C, 64.03; H, 4.01; N, 3.93; Cl, 9.76. | for $C_{18}H_{12}ClNO_4 \cdot 0.1H_2O$<br>Calcd (%): C, 62.93; H, 3.58; N, 4.08; Cl, 10.32.<br>Found (%): C, 62.88; H, 3.64; N, 4.03; Cl, 10.18. |
| 17 | for $C_{19}H_{14}ClNO_4$<br>Calcd (%): C, 64.14; H, 3.97; N, 3.94.<br>Found (%): C, 64.20; H, 4.08; N, 3.97. | for $C_{18}H_{12}ClNO_4 \cdot 0.4C_4H_8O_2$<br>Calcd (%): C, 62.44; H, 4.06; N, 3.72; Cl, 9.40.<br>Found (%): C, 62.57; H, 4.26; N, 3.68; Cl, 9.26. |
| 18 | for $C_{19}H_{14}FNO_4$<br>Calcd (%): C, 67.25; H, 4.16; N, 4.13; F, 5.60.<br>Found (%): C, 67.28; H, 4.35; N, 4.22; F, 5.55. | for $C_{18}H_{12}FNO_4 \cdot 0.1C_4H_8O_2$<br>Calcd (%): C, 66.15; H, 3.86; N, 4.19; F, 5.69.<br>Found (%): C, 65.93; H, 4.00; N, 4.38; F, 5.73. |
| 19 | for $C_{19}H_{14}ClNO_4$<br>Calcd (%): C, 64.14; H, 3.97; N, 3.94; Cl, 9.96.<br>Found (%): C, 64.10; H, 4.15; N, 3.94; Cl, 9.63. | for $C_{18}H_{12}ClNO_4 \cdot C_4H_8O_2$<br>Calcd (%): C, 61.47; H, 4.69; N, 3.26; Cl, 8.25.<br>Found (%): C, 61.52; H, 4.69; N, 3.37; Cl, 8.18. |
| 20 | for $C_{20}H_{17}NO_5$<br>Calcd (%): C, 68.37; H, 4.88; N, 3.99.<br>Found (%): C, 68.13; H, 4.97; N, 3.91. | for $C_{19}H_{15}NO_5$<br>Calcd (%): C, 67.65; H, 4.48; N, 4.15.<br>Found (%): C, 67.49; H, 4.61; N, 4.10. |

TABLE 5-3

| Example | ester derivative (I c) | carboxylic acid (I d) |
|---|---|---|
| 21 | for $C_{21}H_{20}N_2O_4 \cdot 0.2H_2O$<br>Calcd (%): C, 68.54; H, 5.59; N, 7.61.<br>Found (%): C, 68.47; H, 5.38; N, 7.54. | for $C_{20}H_{18}N_2O_4$ HCl<br>Calcd (%): C, 62.10; H, 4.95; N, 7.24.<br>Found (%): C, 62.02; H, 4.68; N, 7.26. |
| 22 | for $C_{20}H_{16}ClNO_4 \cdot 0.1C_4H_8O_2$<br>Calcd (%): C, 64.72; H, 4.47; N, 3.70; Cl, 9.36.<br>Found (%): C, 64.68; H, 4.63; N, 3.70; Cl, 9.19. | for $C_{19}H_{14}ClNO_4$<br>Calcd (%): C, 64.14; H, 3.97; N, 3.94; Cl, 9.40.<br>Found (%): C, 62.57; H, 4.13; N, 3.91; Cl, 9.70. |
| 24 | | for $C_{14}H_{12}FNO_6S$<br>Calcd (%): C, 55.53; H, 3.11; N, 3.60; F, 4.88; S, 8.24.<br>Found (%): C, 55.35; H, 3.21; N, 3.69; F, 4.86; S, 8.26. |
| 25 | for $C_{19}H_{14}BrNO_6S$<br>Calcd (%): C, 49.15; H, 3.04; N, 3.02; Br, 17.21; S, 6.91.<br>Found (%): C, 49.07; H, 3.05; N, 2.94; Br, 17.06; S, 6.91. | for $C_{18}H_{12}BrNO_6S$<br>Calcd (%): C, 48.02; H, 2.69; N, 3.11; Br, 17.75; S, 7.12.<br>Found (%): C, 48.06; H, 2.82; N, 3.23; Br, 17.62; S, 7.12. |
| 26 | for $C_{19}H_{14}ClNO_6S$<br>Calcd (%): C, 54.36; H, 3.36; N, 3.34; Cl, 8.44; S, 7.64.<br>Found (%): C, 54.28; H, 3.48; N, 3.39; Cl, 8.33; S, 7.52. | for $C_{14}H_{12}ClNO_6S$<br>Calcd (%): C, 53.28; H, 2.98; N, 3.45; Cl, 8.74; S, 7.90.<br>Found (%): C, 53.34; H, 3.08; N, 3.88; Cl, 8.48; S, 7.80. |

TABLE 5-3-continued

| Example | ester derivative (I c) | carboxylic acid (I d) |
|---|---|---|
| 27 | | for $C_{25}H_{19}NO_7S$<br>Calcd (%): C, 62.89; H, 4.01; N, 2.93; S, 6.72.<br>Found (%): C, 62.72; H, 4.09; N, 3.01; S, 6.66. |
| 28 | for $C_{20}H_{15}ClFNO_6S \cdot 0.25H_2O$<br>Calcd (%): C, 52.64; H, 3.42; N, 3.07; Cl, 7.77; F, 4.16; S, 7.03.<br>Found (%): C, 52.59; H, 2.33; N, 3.12; Cl, 7.80; F, 4.00, S, 7.11. | for $C_{18}H_{11}ClFNO_6S$<br>Calcd (%): C, 51.01; H, 2.62; N, 3.30; Cl, 8.37; F, 4.48; S, 6.72.<br>Found (%); C, 51.21; H, 2.73; N, 3.30; Cl, 8.21; F, 4.51, 8, 7.59. |
| 29 | for $C_{20}H_{15}ClFNO_6S \cdot 0.25H_2O$<br>Calcd (%): C, 52.64; H, 3.42; N, 3.07; Cl, 7.77; F, 4.16; S, 7.03.<br>Found (%): C, 52.55; H, 3.50; N, 3.09; Cl, 7.80; F, 4.31, S, 7.23. | for $C_{18}H_{11}ClFNO_6S \cdot 0.25H_2O$<br>Calcd (%): C, 50.48; H, 2.71; N, 3.27; Cl, 8.28; F, 4.44; 8, 7.49.<br>Found (%): C, 50.29; H, 3.06; N, 3.11; Cl, 8.08; F, 4.85, S, 7.62. |
| 30 | for $C_{20}H_{14}ClF_2NO_6S \cdot 0.25H_2O$<br>Calcd (%): C, 50.64; H, 3.08; N, 2.95; Cl, 7.47; F, 8.01; S, 6.76.<br>Found (%): C, 50.59; H, 3.20; N, 3.00; Cl, 7.47; F, 8.11, S, 6.82. | for $C_{18}H_{10}ClF_2NO_6S \cdot 0.1C_4H_{10}O$<br>Calcd (%)C, 49.20; H, 2.47; N, 3.12; Cl, 7.89; F, 8.46; S, 7.14.<br>Found (%): C, 48.94; H, 2.69; N, 3.03; Cl, 7.67; F, 8.07, S, 6.98. |
| 31 | for $C_{20}H_{15}C_{12}NO_6S \cdot 0.25H_2O$<br>Calcd (%): C, 50.81; H, 3.30; N, 2.96; Cl, 15.00; 3, 6.78.<br>Found (%): C, 50.73; H, 3.41; N, 3.03; Cl, 15.15; S, 6.89. | for $C_{18}H_{11}Cl_2NO_6S \cdot 0.5H_2O$<br>Calcd (%): C, 48.12; H, 2.69; N, 3.12; Cl, 15.78; S, 7.14.<br>Found (%): C, 48.28; H, 2.81; N, 2.98; Cl, 15.31; 3, 7.10. |
| 32 | for $C_{20}H_{14}Cl_3NO_4S \cdot 0.5H_2O$<br>Calcd (%): C, 46.93; H, 2.95; N, 2.72; Cl, 20.78; S, 6.27.<br>Found (%): C, 46.50; H, 2.86; N, 2.72; Cl, 21.52; S, 6.57. | for $C_{18}H_{12}Cl_3NO_6S \cdot C_2H_5OH$<br>Calcd (%): C, 46.13; H, 3.10; N, 2.69; Cl, 20.42; 3, 6.16.<br>Found (%): C, 46.30; H, 2.91; N, 2.63; Cl, 20.26; S, 6.02. |

TABLE 5-4

| Example | ester derivative (I c) | carboxylic acid (I d) |
|---|---|---|
| 33 | | for $C_{18}H_{11}BrClNO_6S \cdot 0.2C_4H_{10}O$<br>Calcd (%): C, 45.20; H, 2.62; N, 2.80; Br, 16.10; Cl, 7.10; S, 6.42.<br>Found (%): C, 45.08; H, 2.85; N, 2.69; Br, 16.12; Cl, 7.02; S, 6.46. |
| 34 | for $C_{20}H_{15}ClN_2O_8S \cdot 0.5H_2O$<br>Calcd (%): C, 49.24; H, 3.31; N, 5.74; Cl, 7.27; S, 6.57.<br>Found (%): C, 49.04; H, 2.23; N, 5.82; Cl, 7.52; S, 7.31. | for $C_{18}H_{11}ClN_2O_8S$<br>Calcd (%): C, 47.96; H, 2.46; N, 6.21; Cl, 7.86; 3, 7.11.<br>Found (%): C, 48.21; H, 2.64; N, 6.14; Cl, 7.89; S, 7.23. |
| 35 | for $C_{22}H_{19}ClN_2O_7S \cdot 0.5H_2O$<br>Calcd (%): C, 52.85; H, 4.03; N, 5.60.<br>Found (%): C, 52.69; H, 3.93; N, 5.61. | for $C_{18}H_{13}ClN_2O_6S \cdot H_2O$<br>Calcd (%): C, 50.18; H, 3.51; N, 6.50; Cl, 8.23; S, 7.44.<br>Found (%): C, 49.92; H, 3.43; N, 6.47; Cl, 8.58; S, 7.58. |
| 36 | for $C_{27}H_{22}ClNO_6S$<br>Calcd (%): C, 61.89; H, 4.23; N, 2.67; Cl, 6.77; S, 6.12.<br>Found (%): 0, 61.78; H, 4.40; N, 2.65; Cl, 6.61; S, 6.29. | for $C_{25}H_{18}ClNO_4S \cdot 0.25H_2O$<br>Calcd (%C, 60.00; H, 3.73; N, 2.80; Cl, 7.08; S, 6.41.<br>Found (%)0, 60.13; H, 4.25; N, 2.70; Cl, 6.48; S, 6.09. |
| 37 | for $C_{211}H_{18}ClNO_7S \cdot 0.5H_2O$<br>Calcd (%): C, 53.34; H, 4.05; N, 2.96; Cl, 7.50; 3, 6.78.<br>Found (%): C, 53.51; H, 4.03; N, 2.82; Cl, 7.82; S, 7.28. | for $C_{19}H_{14}ClNO_7S \cdot 0.5H_2O$<br>Calcd (%)C, 51.30; H, 3.40; N, 3.15; Cl, 7.97; S, 7.21.<br>Found (%)C, 51.46; H, 3.59; N, 2.98; Cl, 7.68; S, 7.48. |
| 38 | for $C_{22}H_{18}ClNO_8S \cdot 0.5C_4H_{10}O$<br>Calcd (%): 0, 53.72; H, 3.69; N, 2.85; Cl, 7.21; S, 6.52.<br>Found (%): C, 53.56; H, 3.91; N, 3.01; Cl, 7.53; S, 6.15. | for $C_{20}H_{14}ClNO_8S \cdot 0.5C_4H_{10}O$<br>Calcd (%)C, 52.75; H, 3.82; N, 2.80; Cl, 7.08; S, 6.40.<br>Found (%)C, 52.30; H, 4.31; N, 2.76; Cl, 6.85; S, 6.15. |

TABLE 5-4-continued

| Example | ester derivative (I c) | carboxylic acid (I d) |
|---|---|---|
| 39 | for $C_{23}H_{22}ClNO_6S$<br>Calcd (%): C, 58.04; H, 4.66; N, 2.94; Cl, 7.45; 3, 6.74.<br>Found (%): C, 57.76; H, 4.71; N, 2.84; Cl, 7.62; S, 7.13. | for $C_{21}H_{18}ClNO_6S \cdot 0.25H_2O$<br>Calcd (%): C, 55.75; H, 4.12; N, 3.10; Cl, 7.84; 3, 7.09.<br>Found (%): C, 55.86; H, 4.14; N, 2.94; Cl, 7.71; 3, 6.69. |
| 40 | | (Mass: m/z=372 (M$^+$)) |
| 41 | for $C_{16}H_{17}ClN_2O_6S \cdot 0.5H_2O$<br>Calcd (%): C, 46.89; H, 4.43; N, 6.84; Cl, 8.65; S, 7.82.<br>Found (%): C, 47.02; H, 4.32; N, 6.74; Cl, 8.55; 3, 7.85. | for $C_{14}H_{13}ClN_2O_6S$<br>Calcd (%): C, 45.11; H, 3.51; N, 7.51; Cl, 9.51; 3, 8.60.<br>Found (%): C, 45.53; H, 3.71; N, 6.99; Cl, 9.21; 3, 8.69. |
| 42 | for $C_{18}H_{19}ClN_2O_7S$<br>Calcd (%): C, 48.82; H, 4.32; N, 6.33; Cl, 8.00; S, 7.24.<br>Found (%): C, 48.76; H, 4.40; N, 6.60; Cl, 8.01; 3, 7.19. | for $C_{16}H_{15}ClN_2O_7S \cdot 0.4H_2O$<br>Calcd (%): C, 45.54; H, 3.77; N, 6.64; Cl, 8.40; 3, 7.60.<br>Found (%): C, 45.57; H, 3.94; N, 6.67; Cl, 8.22; S, 8.04. |

TABLE 5-5

| Example | ester derivative (I c) | carboxylic acid (I d) |
|---|---|---|
| 43 | | for $C_{13}H_{11}NO_4$<br>Calcd (%): C, 63.67; H, 4.52; N, 5.71.<br>Found (%): C, 63.54; H, 4.52; N, 5.77. |
| 44 | | for $C_{13}H_{10}ClNO_4$<br>Calcd (%): C, 55.83; H, 3.60; N, 5.00; Cl, 12.68.<br>Found (%): C, 55.58; H, 3.90; N, 5.22; Cl, 12.40. |
| 45 | | for $C_{13}H_{10}ClNO_4 \cdot 0.2C_2H_5OH \cdot 0.1H_2O$<br>Calcd (%): C, 55.37; H, 3.95; N, 4.82; Cl, 12.20.<br>Found (%): C, 55.61; H, 4.00; N, 5.00; Cl, 11.86. |
| 46 | for $C_{17}H_{18}BrNO_4$<br>Calcd (%): C, 53.70; H, 4.77; N, 3.68; Br, 21.01.<br>Found (%): C, 53.71; H, 4.81; N, 3.72; Cl, 20.98. | for $C_{16}H_{16}BrNO_4$<br>Calcd (%): C, 52.48; H, 4.40; N, 3.83; Br, 21.82.<br>Found (%): C, 52.43; H, 4.33; N, 3.84; Br, 21.86. |
| 47 | for $C_{21}H_{18}ClNO_4 \cdot 0.1H_2O$<br>Calcd (%): C, 65.71; H, 4.73; N, 3.65; Cl, 9.24.<br>Found (%): C, 65.73; H, 4.83; N, 3.70; Cl, 9.17. | for $C_{13}H_{14}ClNO_4 \cdot 0.1H_2O$<br>Calcd (%): C, 63.82; H, 4.00; N, 3.92; Cl, 9.91.<br>Found (%): C, 63.68; H, 4.08; N, 4.03; Cl, 9.88. |
| 48 | | for $C_{19}H_{13}BrN_4O_4$<br>Calcd (%): C, 51.71; H, 2.90; N, 12.70; Br, 18.11.<br>Found (%): C, 51.46; H, 2.96; N, 12.74; Br, 18.22. |
| 49 | for $C_{25}H_2OClNO_4$<br>Calcd (%): C, 69.21; H, 4.65; N, 3.23; C1, 8.17.<br>Found (%): C, 69.31; H, 4.77; N, 3.11; Cl, 8.01. | for $C_{23}H_{16}ClNO_4$<br>Calcd (%): C, 68.07; H, 3.97; N, 3.45; Cl, 8.74.<br>Found (%): C, 68.44; H, 3.99; N, 3.51; Cl, 8.22. |
| 50 | for $C_{27}H_{22}ClNO_4 \cdot 0.7H_2O$<br>Calcd (%): C, 68.63; H, 4.99; N, 2.96; Cl, 7.50.<br>Found (%): C, 68.77; H, 5.18; N, 3.13; Cl, 6.92. | for $C_{25}H_{18}ClNO_4$<br>Calcd (%): C, 69.53; H, 4.20; N, 3.24; Cl, 8.21.<br>Found (%): C, 69.54; H, 4.28; N, 3.48; Cl, 8.12. |
| 51 | for $C_{26}H_2OClNO_4$<br>Calcd (%): C, 70.04; H, 4.52; N, 3.14; Cl, 7.95.<br>Found (%): C, 69.93; H, 4.65; N, 3.32; Cl, 7.66. | for $C_{25}H_{18}ClNO_4$<br>Calcd (%): C, 69.53; H, 4.20; N, 3.24; Cl, 8.21.<br>Found (%): C, 69.51; H, 4.32; N, 3.54; Cl, 8.03. |

TABLE 5-6

| Example | ester derivative (I c) | carboxylic acid (I d) |
|---|---|---|
| 52 | for $C_{18}H_{18}ClNO_4 \cdot 0.5H_2O$<br>Calcd (%): C, 61.36; H, 5.29; N, 3.98; Cl, 10.06.<br>Found (%): C, 61.41; H, 5.30; N, 4.09; Cl, 9.89. | for $C_{16}H_{14}ClNO_4$<br>Calcd (%): C, 60.10; H, 4.41; N, 4.38; Cl, 11.29.<br>Found (%): C, 59.95; H, 4.57; N, 4.35; Cl, 10.90. |

TABLE 5-6-continued

| Example | ester derivative (I c) | carboxylic acid (I d) |
|---|---|---|
| 53 | for $C_{23}H_{20}ClNO_6 \cdot 0.25H_2O$<br>Calcd (%): C, 61.88; H, 4.63; N, 3.14; Cl, 7.94.<br>Found (%): C, 61.70; H, 4.69; N, 3.26; Cl, 7.67. | for $C_{21}H_{16}ClNO_5 \cdot 0.5H_2O$<br>Calcd (%): C, 59.15; H, 4.05; N, 3.31; Cl, 8.38.<br>Found (%): C, 59.42; H, 4.09; N, 3.54; Cl, 8.71. |
| 54 | | for $C_{21}H_{16}ClNO_2 \cdot H_2O$<br>Calcd (%): C, 58.41; H, 4.20; N, 3.24; Cl, 8.21.<br>Found (%): C, 58.75; H, 4.09; N, 3.30; Cl, 8. 31. |
| 55 | for $C_{21}H_{18}ClNO_6S \cdot 0.25H_2O$<br>Calcd (%): C, 55.75; H, 4.12; N, 3.10; Cl, 7.84; S, 7.09.<br>Found (%): C, 55.79; H, 4.18; N, 3.12; Cl, 7.64; S, 7.12. | for $C_{19}H_{14}ClNO_6S \cdot 0.5H_2O$<br>Calcd (%): C, 53.21; H, 3.53; N, 3.29; Cl, 8.27; S, 7.48.<br>Found (%): C, 53.59; H, 3.70; N, 3.19; Cl, 8.05; S, 7.42. |
| 56 | for $C_{21}H_{17}ClN_2O_5$<br>Calcd (%): C, 61.10; H, 4.15; N, 6.79; Cl, 8.59.<br>Found (%): C, 60.97; H, 4.31; N, 6.64; Cl, 8.38. | for $C_{19}H_{13}ClN_2O_5 \cdot 0.5C_4H_6O_2$<br>Calcd (%): C, 58.82; H, 4.00; N, 6.53; Cl, 8.27.<br>Found (%): C, 58.78; H, 4.10; N, 6.70; Cl, 8.11. |
| 57 | for $C_{26}H_{20}ClNO_4$<br>Calcd (%): C, 70.03; H, 4.52; N, 3.14; Cl, 7.95.<br>Found (%): C, 69.82; H, 4.65; N, 3.10; Cl, 8.20. | for $C_{25}H_{18}ClNO_4 \cdot 0.3H_2O$<br>Calcd (%): C, 68.67; H, 4.29; N, 3.20; Cl, 8.11.<br>Found (%): C, 68.90; H, 4.37; N, 3.28; Cl, 8.31. |
| 58 | | for $C_{24}H_{16}FNO_6S$<br>Calcd (%): C, 61.93; H, 3.46; N, 3.01; F, 4.08; S, 6.89.<br>Found (%): C, 62.00; H, 3.66; N, 3.26; F, 3.98, S, 6.61. |
| 59 | for $C_{27}H_{23}NO_4$<br>Calcd (%): C, 76.22; H, 5.45; N, 3.29.<br>Found (%): C, 76.1, S; H, 5.52; N, 3.32. | for $C_{26}H_{21}NO_4$<br>Calcd (%): C, 75.90; H, 5.14; N, 3.44.<br>Found (%): C, 75.85; H, 5.30; N, 3.32. |

EXAMPLE 60

4-[1-(4-Carboxybenzyl)-5-chloroindol-3-yl]-2-hydroxy-4-oxo-2-butenoic acid

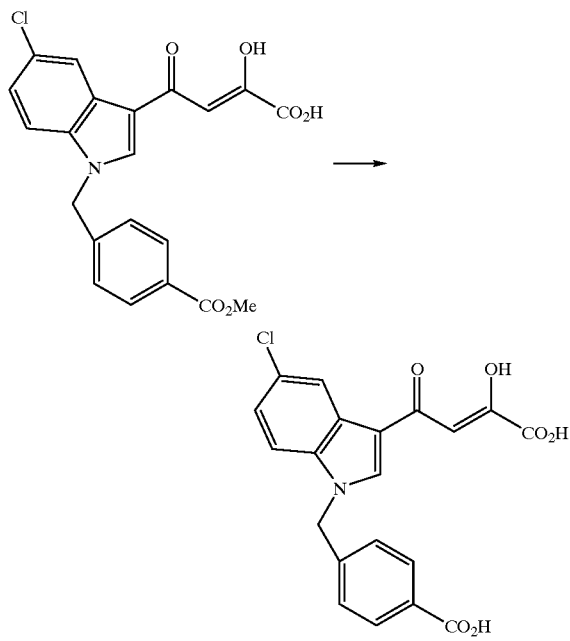

To a solution of 82 mg (0.2 mmol) of 4-[5-chloro-1-(4-methoxycarbonylbenzyl)indol-3-yl]-2-hydroxy-4-oxo-2-butenoic acid, prepared in a manner similar to that described in Example 23, in 75% MeOH (35 ml) was added 42 mg (1.0 mmol) of LiOH. After the mixture was stirred for 5 hours at room temperature, the solvent was removed under reduced pressure. The residue was acidified with 1 N hydrochloric acid and the mixture was extracted with ethyl acetate. The organic layer was washed with water and saturated brine, and then dried. The solvent was evaporated and the residue was recrystallized from ethyl acetate/ether to give 63 mg of the titled compound. Yield: 79%.

m.p.: 245° C. (decomposition) NMR ($d_6$-DMSO) δ: 5.63 (2H, s), 7,00 (1H, s), 7.32 (1H, dd, J=8.7 Hz, 2.1 Hz), 7.42 (2H, d, J=8.1 Hz), 7.63 (1H, d, J=8.7 Hz), 7.91 (2H, d, J=8.1 Hz), 8.23 (1H, d, J=2.1 Hz), 9.07 (1H, s). Elemental Analysis for $C_{20}H_{14}ClNO_6$ $0.25C_4H_8O_2$ Calcd. (%):C,59.80; H,3.82; N,3.32; Cl,8.40. Found. (%):C,59.85; H,4.10; N,3.30; Cl,8.16.

The compounds in Example 61–62 were prepared in accordance with Example 60.

EXAMPLE 61

4-[1-(3-Carboxybenzyl)-5-chloroindol-3-yl]-2-hydroxy-4-oxo-2-butenoic acid

NMR ($d_6$-DMSO) δ: 5.62 (2H, s), 7.00 (1H, s), 7.33 (1H, dd, J=8.7 Hz, 2.1 Hz), 7.48 (1H, t, J=8.1 Hz), 7.59 (1H, d, J=7.5 Hz), 7.67 (1H, d, J=8.7 Hz), 7.87–8.20 (2H, m), 8.23 (1H, (d, J=2.1 Hz), 9.10 (1H, s), 13.0 (2H, brs). Elemental Analysis for $C_{20}H_{14}ClNO_6$ Calcd. (%):C,60.09; H,3.53; N,3.550; Cl,8.87. Found. (%):C,60.16; H,3.94; N,3.49; Cl,8.66.

EXAMPLE 62

4-[1-(5-Carboxythiophen-2-ylmethyl)-5-chloroindol-3-yl]-2-hydroxy4-oxo2-butenoic acid NMR (d$_6$-DMSO) δ: 5.78 (2H, s), 6.97 (1H, s), 7.25 (1H, d, J=3.9 Hz), 7.38 (1H, dd, J=8.7 Hz, 2.1 Hz), 7.59(1H, d, J=3.9 Hz), 7.79(1H, d, J=8.7 Hz), 8.23(1H, d, J=2.1 Hz), 9.04 (1H, s), 13.0 (1H, brs). Elemental Analysis for C$_{18}$H$_{12}$ClNO$_6$S 0.25C$_4$H$_8$O$_2$ 0.5H$_2$O Calcd. (%):C,52.24; H,3.46; N,3.21; Cl,8.11; S,7.34. Found. (%):C,52.56; H,3.46; N,3.34; Cl,8.09; S,7.47.

The Compounds in Example 63–66 were prepared in accordance with synthetic route shown below.

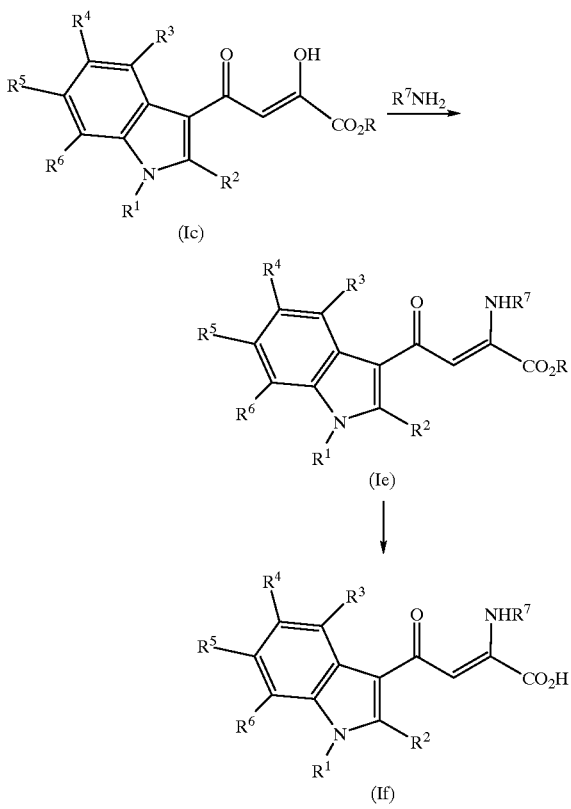

EXAMPLE 63

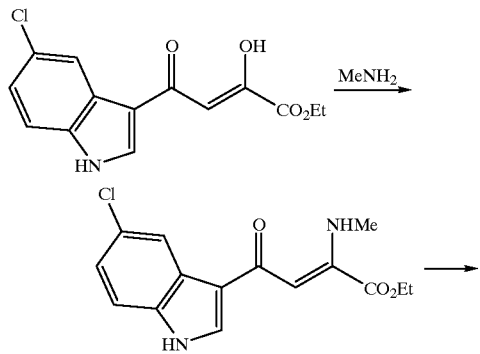

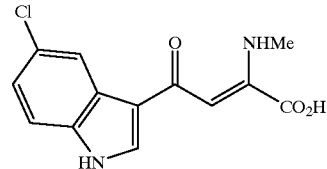

(1) 4-(5-Chloroindol-3-yl)-2-methylamino-4-oxo-2-butenoic acid ethyl ester

To a solution of 0.59 g (2.0 mmol) of 4-(5-chloroindol-3-yl)-2-hydroxy-4-oxo-2-butenoic acid ethyl ester prepared in Example 1(1) in 95% EtOH (10 ml) was added 0.55 g (6.0 mmol) of methylamine acetate. After refluxing for 2.5 hours, the reaction mixture was concentrated and the residue was dissolved in ethyl acetate. The ethyl acetate was washed with water, dried, and then concentrated. The resulting residue was chromatographed on silica gel (ethyl acetate as eluant) to give 0.23 g of the titled compound as oil. Yield: 38%.

NMR (d$_6$-DMSO) δ: 1.33 (3H, t, J=7.0 Hz), 2.96 (3H, d, J=5.4 Hz), 4.32 (2H, q, J=7.0 Hz), 5.99 (1H, s), 7.19 (1H, dd, J=8.6 Hz, 2.0 Hz), 7.45 (1H, d, J=8.6 Hz), 8.27 (1H, d, J=2.0 Hz), 8.28 (1H, s), 9.96 (1H, brm), 11.9 (1H, brs).

(2) 4-(5-Chloroindol-3-yl)-2-methylamino-4-oxo-2-butenoic acid

To a solution of 0.22 g of the ester described in above (1) in dioxane (2.2 ml) was added 1 N NaOH (0.9 ml). After stirring for 2 hours, the mixture was treated with 1 N hydrochloric acid (0.9 ml), and concentrated under reduced pressure. The residue was diluted with water. The obtained crystal was collected by filtration, and washed with water and 95% EtOH to give 0.15 g of the titled compound. Yield: 80%.

m.p.: 228–229° C. (decomposition) NMR (d$_6$-DMSO) δ: 3.00 (3H, d, J=5.6 Hz), 6.04 (1H, s), 7.22 (1H, dd, J=8.8 Hz, 2.0 Hz), 7.53 (1H, d, J=8.8 Hz), 8.17 (1H, d, J=2.0 Hz), 8.66 (1H, brm), 8.75 (1H, d, J=3.0 Hz), 12.5 (1H, brs). Elemental Analysis for C$_{13}$H$_{11}$ClN$_2$O$_3$ Calcd. (%):C,56.04; H,3.98; N,10.05; Cl,12.72. Found. (%):C,56.06; H,4.05; N,10.32; Cl,12.62.

In Example 64–66, the other ester derivatives (Ie) and the corresponding carboxylic acid (If) were prepared in accordance with Example 63.

EXAMPLE 64

(1) 4-(1-Benzyl-5-chloroindol-3-yl)-2-methylamino-4-oxo-2-butenoic acid ethyl ester m.p.: 131–132° C. (recrystallized from 95% EtOH) NMR (CDCl$_3$) δ: 1.40 (3H, t, J=7.0 Hz), 3.10 (3H, d, J=5.2 Hz), 4.36 (2H, q, J=7.0 Hz), 5.32 (2H, s), 5.99 (1H, s), 7.08–7.35 (7H, m), 7.71 (1H, s), 8.44 (1H, t, J=1.2 Hz). Elemental Analysis for C$_{22}$H$_{21}$ClN$_2$O$_3$ Calcd. (%):C,66.58; H,5.33; N,7.06; Cl,8.93. Found. (%):C,66.53; H,5.39; N,8.77; Cl,7.11.

(2) 4-(1-Benzyl5-chloroindol-3-yl)-2-methylamino-4-oxo-2-butenoic acid m.p.: 205–210° C. (decomposition) (recrystallized from 95% EtOH) NMR (d$_6$-DMSO) δ: 3.02 (3H, d, J=5.4 Hz), 5.56 (2H, s), 6.03 (1H, s), 7.25–7.38 (6H, m), 7.62 (1H, d, J=9.0 Hz), 8.20 (1H, d, J=2.1 Hz), 8.72 (1H, brq, J=5.4 Hz), 8.90(1H, s). Elemental Analysis for C$_{20}$H$_{17}$ClN$_2$O$_3$ Calcd. (%):C,65.13; H,4.65; N,7.60; Cl,9.61. Found. (%):C,65.04; H,4.60; N,7.77; Cl,9.36.

EXAMPLE 65

(1) 4-(1-Benzyl-5-chloroindol-3-yl)-2-(2-ethoxyethylamino)-4-oxo-2-butenoic acid ethyl ester m.p.: 73–74° C. (recrystallized from i-Pr$_2$O) NMR (CDCl$_3$) δ: 1.22 (3H, t, J=7.2 Hz), 1.37 (3H, t J=7.2 Hz), 3.46–3.67 (6H, m), 4.34 (2H, q, J=7.2 Hz), 5.32 (2H, s), 6.01 (1H, s), 7.08–7.36 (7H, m), 7.72 (1H, s), 8.44 (1H, t, J=1.2 Hz). Elemental Analysis for C$_{25}$H$_{27}$ClN$_2$O$_4$ Calcd. (%):C, 66.00; H,5.98; N,6.16; Cl,7.79. Found. (%):C,66.10; H,6.26; N,6.18; Cl, 7.66.

(2) 4-(1-Benzyl-5-chloroindol-3-yl)-2-(2-ethoxyethylamino)-4-oxo-2-butenoic acid m.p.: 184–186° C. (decomposition) (recrystallized from 95% EtOH) NMR (d$_6$-DMSO) δ:1.10 and 1.15 (3H, t J=7.0 Hz), 3.40–3.70 (6H, m), 5.47 and 5.56 (2H, s), 6.01 and 6.03 (1H, s), 7.18–7.64 (7H, m), 8.20 and 8.29 (1H, d, J=2.1 Hz), 8.54 and 8.96 (1H, s), 8.26 and 10.2 (1H, brs). Elemental Analysis for C$_{23}$H$_{23}$ClN$_2$O$_4$ 0.2H$_2$O Calcd. (%):C,64.17; H,5.48; N,6.51; Cl,8.24. Found. (%):C,64.27; H,5.71; N,6.71; Cl,8.13.

EXAMPLE 66

(1) 2-Amino-4-(indol-3-yl)-4-oxo-2-butenoic acid ethyl ester m.p.: 200–205° C. (recrystallized from ethyl acetate) NMR (CDCl$_3$) δ: 1.41 (3H, t, J=7.0 Hz), 4.38 (2H, q, J=7.0 Hz), 6.51 (1H, s), 7.25–7.45 (4H, m), 7.89 (1H, d, J=3.0 Hz), 8.42–8.60 (2H, brm). Elemental Analysis for C$_{14}$H$_{14}$N$_2$O$_3$ Calcd. (%/):C,65.11; H,5.46; N,10.85. Found. (%):C,65.08; H,5.54; N,10.66.

(2) The above ethyl ester in dioxane was treated with an equivalent of 1 N NaOH. After stirring for 3 hours at room temperature, the mixture was concentrated under reduced pressure to dryness to give 2-amino-4-(indol-3-yl)-4-oxo-2-butenoic acid sodium salt NMR (d$_6$-DMSO) δ: 6.29 (1H, s), 6.73 (1H, d, J=7.8 Hz), 7.01–7.20 (2H, m), 7.36–7.48 (1H, m), 7.95 (1H, s), 8.22–8.35 (1H, m), 9.22 (1H, d, J=7.8 Hz), 11.6 (1H, brs). Elemental Analysis for C$_{12}$H$_9$N$_2$O$_3$Na 0.6H$_2$O Calcd. (%):C,54.80; H,3.91; N,10.65. Found. (%):C,54.71; H,3.92; N,10.62.

The compounds in Example 67–71 were prepared in accordance with the following reaction route.

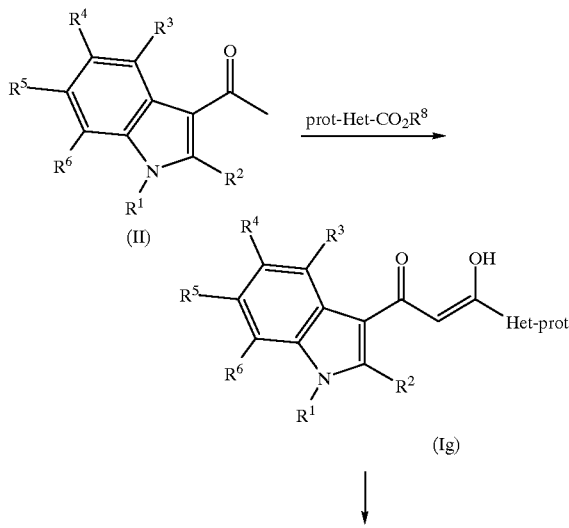

EXAMPLE 67

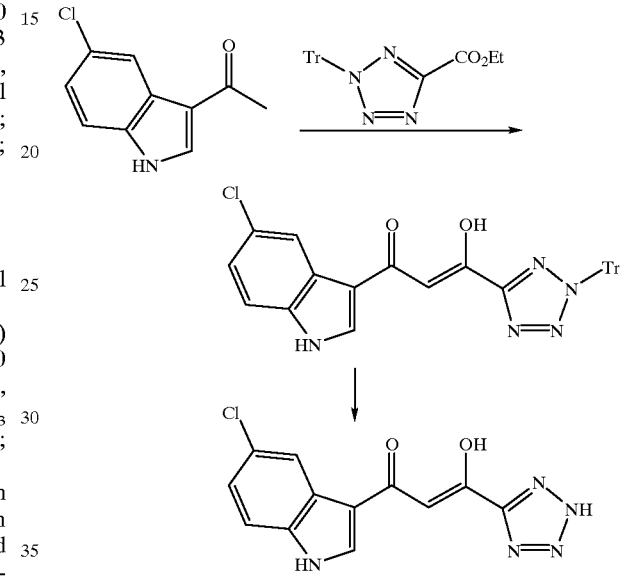

(1) 1-(5-Chloroindol-3-yl)-3-hydroxy3-(2-trityl-2H-tetrazol-5-yl)-propenone

To a solution of 0.58 g (3.0 mmol) of 3-acetyl-5-chloroindole in THF (9 ml) was added dropwise 1M LHMDS (9 ml, 9 mmol) in THF under −65° C. The mixture was warmed to −20° C., and stirred at the same temperature for 1 hour. After cooling down to −65° C., a solution of 1.73 g (4.5 mmol) or 2-trityl-2H-tetrazole-5-carboxylic acid ethyl ester in THF (3 ml) was added thereto. The reaction mixture was gradually warmed to room temperature and stirred for 2 hours. The reaction mixture was poured into excess amount of saturated aqueous ammonium chloride. The precipitated was collected by filtration and dissolved in THF (100 ml), and then dried. Furthermore, the aqueous layer was extracted twice with ethyl acetate. The ethyl acetate was washed with water, and dried. The combined solutions were concentrated and the resulting residue was washed with ethyl acetate to give 1.40 g of the titled compound as an yellow powder. Yield: 88%.

NMR(d$_6$-DMSO) δ: 6.66 (1H, s), 7.05–7.08 (5H, m), 7.14 (1H, dd, J=8.4 Hz, 2.1 Hz), 7.39–7.44 (11H, m), 8.01 (1H, s), 8.29 (1H, d, J=2.1 Hz), 11.7 (1H, brs).

(2) 1-(5-Chloroindol-3-yl)-3-hydroxy-3-(2H-tetrazol-5-yl)-propenone

To a suspension of 0.64 g (1.2 mmol) of the compound obtained above (1) in dioxane (9 ml) was added 1 N hydrochloric acid (7 ml) and the mixture was refluxed for 1 hour. After cooling, the precipitated crystal was collected by filtration and washed successively with ethyl acetate and water, and then dried to give 0.26 g of the titled compound as yellow crystal. Yield: 75%.

m.p. : 250° C. (decomposition) NMR (d$_6$-DMSO) δ: 7.26 (1H, s), 7.32 (1H, dd, J=8.7 Hz, 2.1 Hz), 7.56 (1H, d, J=8.7 Hz), 8.21 (1H, d, J=2.1 Hz), 8.84 (1H, d, J=3.3 Hz), 12.6(1H, brs). Elemental Analysis for C$_{12}$H$_8$ClN$_5$O$_2$ Calcd. (%):C, 49.76; H,2.78; N,24.18; Cl,12.24. Found. (%):C,49.43; H,3.08; N,23.83; Cl,11.93.

EXAMPLE 68–71

The compound (Ih) wherein Y is a heteroaryl was prepared in accordance with Example 67. The structure and physical properties of each compound were shown below.

TABLE 6-1

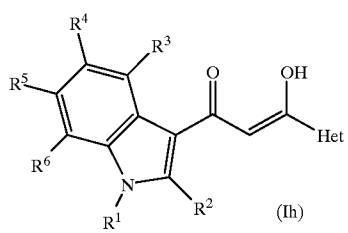

| Example | Het | R$^1$ | R$^2$ | R$^3$ | R$^4$ | R$^5$ | R$^6$ | Recrystallization | m.p. (° C.) |
|---|---|---|---|---|---|---|---|---|---|
| 68 | Tet | H | Ph(2-Cl) | H | H | H | H | i-Pr$_2$O | 209–210 |
| 69 | Tet | H | Bn(4-F) | H | Cl | H | H | Et$_2$O | 138 |
| 70 | Tet | H | Bn(4-Cl) | H | Cl | H | H | Et$_2$O | 200 |
| 71 | Tri | H | H | H | Cl | H | H | EtOAc | 277–279 |

Tet: 2H-tetrazol-5-yl;
Tri: 1H[1,2,4]-triazol-3-yl

TABLE 6-2

| Example | NMR chemical shift |
|---|---|
| 68 | (d$_6$-DMSO)δ: 6.37(1H, s), 7.32–7.37(2H, m), 7.51–7.59(2H, m), 7.65–7.77(3H, m), 8.25-8.28(1H, m), 12.7(1H, s). |
| 69 | (d$_6$-DMSO)δ: 7.01–7.55(8H, m), 8.01(1H, s), 12.5(1H, s), 15.2(1H, br). |
| 70 | (d$_6$-DMSO)δ: 4.54(2H, s), 6.99(1H, s), 7.27–7.42(5H, m), 7.53(1H, d, J=8.6Hz), 8.01(1H, d, J=1.6Kz), 12.6(1H, s). |
| 71 | (d$_6$-DMSO)δ: 7.09(1H, s), 7.28(1H, dd, J=8.7Hz, 2.4Hz), 7.54(1H, d, J=8.7Hz), 8.21(1H, d, J=2.4Hz), 8.69(2H, brs), 12.5(1H, s). |

TABLE 6.3

| Example | Elementary Analysis |
|---|---|
| 68 | C$_{18}$H$_{12}$ClN$_5$O$_2$ 0.075CHCl$_3$<br>Calcd.(%): C, 57.93; H, 3, 25; N, 18.69; Cl, 11.59.<br>Found.(%): C, 57.90; H, 3.46; N, 18.42; Cl, 11.47. |
| 69 | C$_{19}$H$_{13}$ClFN$_5$O$_2$ 0.4C$_4$H$_{10}$O<br>Calcd.(%): C, 57.88; H, 4.01; N, 16.35; Cl, 8.29; F, 4.44.<br>Found.(%): C, 57.50; H, 4.12; N, 16.21; Cl, 8.01; F, 4.33. |

TABLE 6.3-continued

| Example | Elementary Analysis |
|---|---|
| 70 | C$_{19}$H$_{13}$Cl$_2$N$_5$O$_2$ 0.5C$_4$H$_{10}$O<br>Calcd.(%): C, 55.89; H, 4.02; N, 15.52; Cl, 15.71.<br>Found.(%): C, 55.75; H, 4.07; N, 15.62; Cl, 15.50. |
| 71 | C$_{13}$H$_9$ClN$_4$O$_2$ 0.2H$_2$O 0.1C$_4$H$_8$O$_2$<br>Calcd.(%): C, 53.45; H, 3.41; N, 18.61; Cl, 11.77.<br>Found.(%): C, 53.64; H, 3.42; N, 18.52; Cl, 11.74. |

The compound(s in Example 75–84 were prepared in accordance with the following scheme.

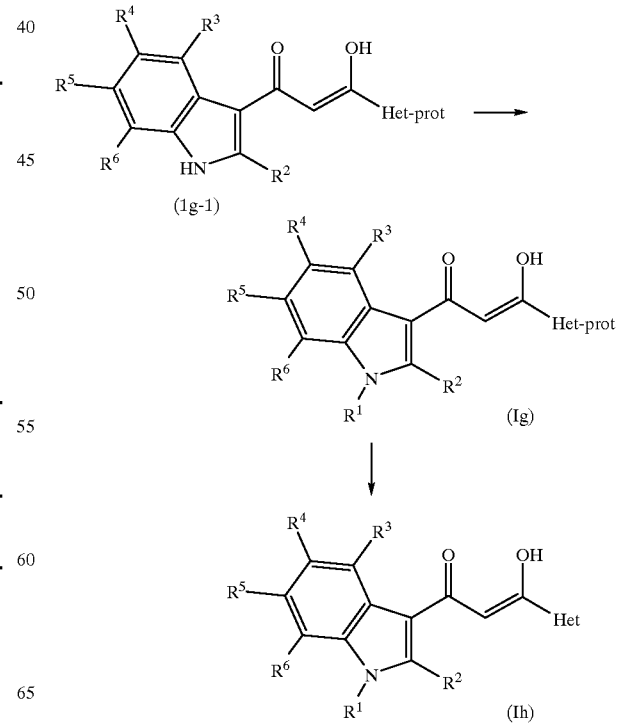

EXAMPLE 75

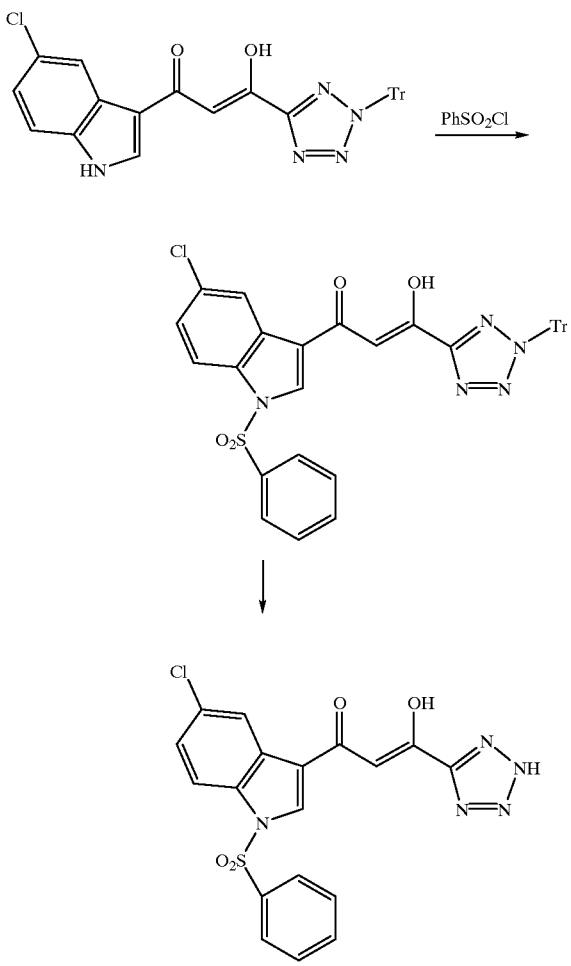

(1) 1-(1-Benzenesulfonyl-5-chloroindol-3-yl)-3-hydroxy-3-(2-trityl-2H-tetrazol-5-yl)-propenone To a suspension of 0.19 g (4.8 mmol) of NaH (60% dispersion in mineral oil) in THF (16 ml) was added 0.85 g (1.6 mmol) of 1-(5-chloroindol-3-yl)-3-hydroxy-3-(2-trityl-2H-tetrazol-5-yl)-propenone prepared in Example 67. Subsequently, the mixture was stirred for 15 minutes at room temperature and then mixed with 0.62 g (3.5 mmol) of benzenesulfonyl chloride. After stirring for 1 hour at room temperature, the mixture was poured into excess amount of saturated aqueous ammonium chloride and extracted with ethyl acetate (50 ml). The organic layer washed with water, and dried. The solvent was removed and the residue was washed with n-hexane, followed by crystallization from ether to give 0.73 g of the titled compound as white powder. Yield: 68%.

NMR ($d_6$-DMSO) δ: 7.09–7.12 (5H, m), 7.42–7.46 (10H, m), 7.53 (1H, dd, J=9.0 Hz, 2.4 Hz), 7.55 (1H, s), 7.67 (2H, m), 7.79 (1H, m), 8.05 (1H, d, J=9.0 Hz), 8.26 (1H, d, J=2.4 Hz), 9.38 (1H, s).

(2) 1-(1-Benzenesulfonyl-5-chloroindol-3-yl)-3-hydroxy-3-(2H-tetrazol-5-yl)-propenone To a solution of 0.67 g (1.0 mmol) of the compound obtained in above (1) in dioxane (5 ml) was added hydrochloric acid (5 ml). The mixture was refluxed for 1 hour. After cooling, the precipitated crystal was collected by filtration and washed successively with ethyl acetate and water, and then dried to give 0.32 g of the titled compound. Yield: 74%.

m.p.: 240° C. (decomposition) NMR ($d_6$-DMSO) δ: 7.52 (1H, dd, J=9.0 Hz, 2.1 Hz), 7.58 (1H, s), 7.66–7.71 (2H, m), 7.77–7.82 (1H, m), 8.06 (1H, d, J=9.0 Hz), 8.22–8.25 (3H, m), 9.39 (1H, s). Elemental Analysis for $C_{18}H_{12}ClN_5O_4S$ $0.4H_2O$ Calcd. (%):C,49.47; H,2.95; N,16.02; Cl,8.11, S,7.34. Found. (%):C,49.56; H,3.14; N,15.97; Cl,7.96. S,7.46.

EXAMPLE 76–84

The compound wherein Y represents heteroaryl was prepared in accordance with Example 75. The structure and the physical data of each compound are shown below.

TABLE 7-1

| Example | Het | $R^1$ | $R^2$ | $R^3$ | $R^4$ | $R^5$ | $R^6$ | Recrystallization Solvent | m.p. (° C.) |
|---|---|---|---|---|---|---|---|---|---|
| 76 | Tet | —SO$_2$Ph | H | H | CF$_3$ | H | H | EtOAc—Et$_2$O | >250 |
| 77 | Tet | —SO$_2$Ph(3-CF$_3$) | H | H | Cl | H | H | EtOAc | 256 |
| 78 | Tet | —SO$_2$Ph(3,5-CF$_3$) | H | H | Cl | H | H | EtOAc | >250 |
| 79 | Tet | —SO$_2$Ph(2,4,6-iPr) | H | H | Cl | H | H | Et$_2$O—Hex | 211 |
| 80 | Tet | —SO$_2$-2-thienyl | H | H | Cl | H | H | EtOAc-i-Pr$_2$O | 243 |
| 81 | Tet | —CH$_2$Ph | H | H | Cl | H | H | aq.dioxane | >240 |
| 82 | Tet | —CH$_2$Ph(4-N$_3$) | H | H | Cl | H | H | aq.dioxane | >210 |
| 83 | Tri | —SO$_2$Ph | H | H | Cl | H | H | aq.dioxane | 282–284 |
| 84 | Imi | —SO$_2$Ph | H | H | Cl | H | H | aq.dioxane | 252–254 |

(note)
the compound in Example 84 is 0.9HCl salt;
Imi: 2-imidazolyl

TABLE 7-2

| Example | NMR chemical shifts |
|---|---|
| 76 | ($d_6$-DMSO)δ: 7.63–7.85(5H, m), 8.29(3H, m), 8.60(1H, s), 9.52(1H, s). |
| 77 | ($d_6$-DMSO)δ: 7.53–7.55(2H, m), 7.90–7.97(1H, m), 8.08–8.26(3H, m), 8.51–8.59(2H, m), 9.44(1H, s). |
| 78 | ($d_6$-DMSO)δ: 7.52(1H, s), 7.53(1H, dd, J=9.0Hz, 2.0Hz), 8.24 (1H, d, J=9.0Hz),8.25(1H, d, J=2.0Hz), 8.59(1H, s), 8.93(2H, s), 9.47(1H, s). |
| 79 | (CDCl$_3$)δ: 1.13(12H, d, J=7.0Hz), 1.26(6H, J=6.8Hz), 2.94(1H, sept, J=6.8Hz), 4.08(2H, sept, J=7.0Hz), 7.23(5H, m), 8.32(1H, s), 8.43(1H, s), 12.5(2H, brs). |
| 80 | ($d_6$-DMSO)δ: 7.26–7.30(1H, m), 7.55–7.60(2H, m), 8.00–8.28(4H, m), 9.34(1H, s). |
| 81 | ($d_6$-DMSO)δ: 5.56(2H, s), 7.24(1H, s), 7.28–7.37(6H, m), 7.79(1H, d, J=9.0Hz), 8.22(1H, d, J=2.4Hz), 9.11(1H, s). |
| 82 | ($d_6$-DMSO)δ: 5.55(2H, s), 7.11(2H, d, J=8.4Hz), 7.23(1H, s), 7.35(1H, dd, J=9.0Hz, 2.4Hz), 7.44(2H, d, J=8.4Hz), 7.70(1H, d, J=9.0Hz), 8.22(1H, d, J=2.4Hz), 9.10(1H, s). |
| 83 | ($d_6$-DMSO)δ: 7.36(1H, s), 7.51(1H, dd, J=8.7Hz, 2.4Hz), 7.64–7.71(2H, m), 7.76–7.82(1H, m), 8.05(1H, d, J=8.7Hz), 8.12–8.17(1H, m), 8.22–8.27(2H, m), 8.80(1H, brs), 9.22(1H, s). |
| 84 | ($d_6$-DMSO)δ: 7.45–7.54(3H, m), 7.65–7.70(3H, m), 7.77–7.82 (1H, m), 8.00–8.07(1H, m), 8.12–8.22(3H, m), 9.10(1H, s). |

TABLE 7-3

| Example | Compound (Ih) |
|---|---|
| 76 | $C_{19}H_{12}F_3N_5O_4S$ 0.2$H_2O$<br>Calcd.(%): C, 48.87; H, 2.68; N, 15.00; F, 12.20; S, 6.87.<br>Found.(%): C, 48.78: H.2.87; N, 15.00; F, 11.83; S, 6.82. |
| 77 | $C_{19}H_{11}ClF_3N_5O_4S$<br>Calcd.(%): C, 45.84; H, 2.23; N, 14.07; Cl, 7.12; F, 11.45; S, 6.44.<br>Found.(%): C, 45.76; H, 2.51: N, 14.02; Cl, 7.29: F, 11.45; S, 6.46. |
| 78 | $C_{20}H_{10}ClF_6N_5O_4S$<br>Calcd.(%): C, 42.45; H, 1.78; N, 12.38; Cl, 6.27; F, 20.15; S, 5.67.<br>Found.(%): C, 44.40; H, 1.88: N, 12.26; Cl, 6.27; F, 20.37; S, 5.71. |
| 79 | $C_{27}H_3OClN_5O_4S$<br>Calcd.(%): C, 58.32; H, 5.44; N, 12.59; Cl, 6.38; S, 5.77.<br>Found.(%): C, 58.37; H, 5.45: N, 12.30; Cl, 6.43; S, 5.66. |
| 80 | $C_{16}H_{10}ClN_5O_4S2$ 0.25$C_4H_8O_2$<br>Calcd.(%): C, 44.59; H, 2.64; N, 15.29; Cl, 7.74; S, 14.01.<br>Found.(%): C, 44.55; H, 2.85; N, 15.04; Cl, 7.98; S, 14.06. |
| 81 | $C_{19}H_{14}ClN_5O_2$<br>Calcd.(%): C, 60.09; H, 3.72; N, 18.44; Cl, 9.33.<br>Found.(%): C, 60.06: H. 3.89; N, 18.42; Cl, 9.13. |
| 82 | $C_{19}H_{13}ClN_8O_2$<br>Calcd.(%): C, 54.23; H, 3.11; N, 26.63; Cl, 8.42.<br>Found.(%): C, 54.56; H, 3.37; N, 26.59; Cl, 7.94. |
| 83 | $C_{19}H_{13}ClN_4O_4S$<br>Calcd.(%): C, 53.21; H, 3.06; N, 13.06; Cl, 8.27; S, 7.48.<br>Found.(%): C, 53.43; H, 3.36; N, 12.85; Cl, 8.17; S, 7.40. |
| 84 | $C_{20}H_{14}ClN_3O_4S$ 0.9HCl<br>Calcd.(%): C, 52.15; H, 3.26; N, 9.12; Cl, 14.62; S, 6.96.<br>Found.(%): C, 51.99; H, 3.49; N, 9.08; Cl, 14.34; S, 7.19. |

EXAMPLE 85

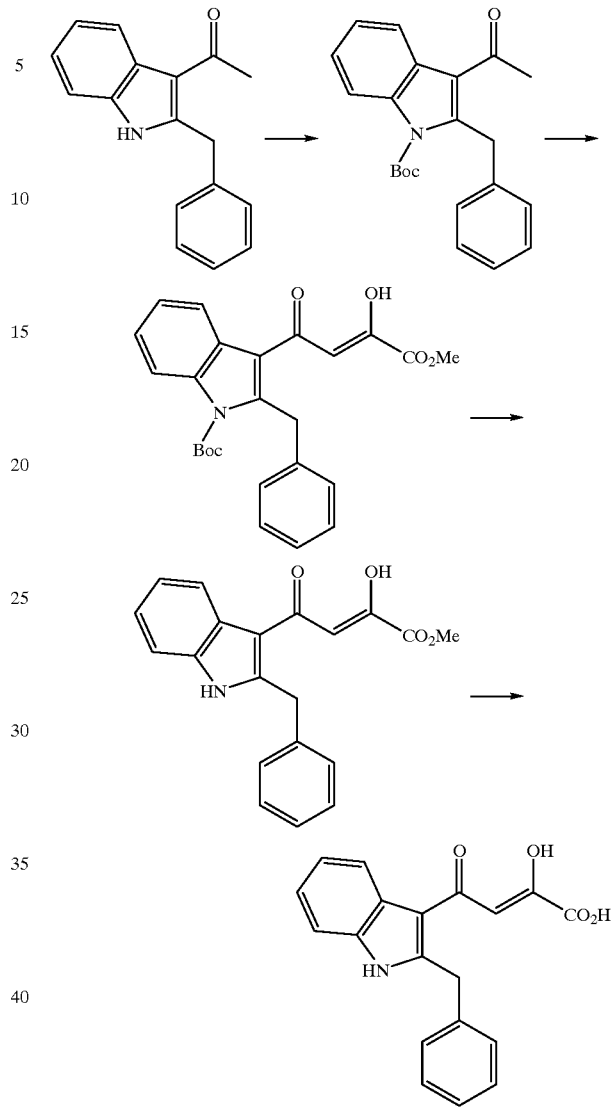

(1) 4-(2-Benzylindol-3-yl)-2-hydroxy-4-oxo-2-butenoic acid methyl ester (a) To a solution of 2.70 g (10.8 mmol) of 3-acetyl-2-benzylindole prepared in the reference example 1 in THF (20 ml) was added under ice-cooling, 122 mg (1 mmol) of 4-dimethylaminopyridine, and subsequently added dropwise a solution of 2.8 g (13 mmol) of di-tert-butyl dicarbonate in THF (5 ml). After stirring for 1 hour at room temperature, the reaction mixture was partitioned between ethyl acetate and water. The ethyl acetate was washed with water, dried, and then concentrated to give 1.8 g of 3-acetyl-1-tert-buthoxycarbonyl-2-benzylindole as a crystal. Yield: 48%.

NMR ($d_6$-DMSO) δ: 1.40 (9H, s), 2.63 (3H, s), 4.81 (2H, s), 7.01 (2H, d, J=7.0 Hz), 7.10–7.46 (5H, m), 7.98–8.10 (2H, m).

(b) To a solution of 1.75 g (5.0 mmol) of the compound obtained in above (a) in THF (50 ml) was added 1M LHMDS (6 ml, 6 mmol) in THF at −70° C. Subsequently, the mixture was warmed to 0° C. and stirred for 1 hour at the same temperature. The mixture was cooled again to −70° C. and treated with 709 mg (6.0 mmol) of oxalic acid diethyl ester in THF (6 ml). The reaction mixture was gradually warmed and stirred for 1 hour at −30° C. The reaction mixture was poured into saturated aqueous ammonium chloride and extracted with ethyl acetate. The extract was washed with water and dried. The solvent was removed to give 4-(2-benzyl-1-tert-butoxycarbonyl-indol-3-yl)-2-hydroxy-4-oxo-2-butenoic acid methyl ester as an oil.

NMR(CDCl$_3$) δ:1.45 (9H, s), 3.90 (3H, s), 4.83 (2H, s), 6.85 (1H, s), 7.00–7.10 (2H, m), 7.15–7.32 (3H, m), 7.34–7.46 (2H, m), 7.90–8.02 (1H, m).

(c) To 2.1 g (4.8 mmol) of the compound obtained in above (b) was added 2 ml of trifluoroacetic acid. After stirring for 2 hours at room temperature, the mixture was concentrated under reduced pressure. The residue was poured into ice water, and extracted with ethyl acetate. The extract was washed successively with sodium bicarbonate and water, and then dried. The solvent was removed and the obtained yellow powder was recrystallized from ethyl acetate-n-hexane to give 0.96 g of the titled compound. Yield: 60%. m.p.: 197–199° C. (decomposition).

NMR (d$_6$-DMSO) δ: 3.83 (3H, s), 4.51 (2H, s), 6.86 (1H, s), 7.05–7.40 (7H, m), 7.44–7.56 (1H, m), 7.90–8.04 (1H, m), 12.5 (1H, brs). Elementary Analysis (for C$_{20}$H$_{17}$NO$_4$) Calcd. (%):C,71.63; H,5.11; N,4.18. Found. (%):C,71.62; H,5.23; N,4.22.

(2) 4-(2-Benzylindol-3-yl)-2-hydroxy-4-oxo-2-butenoic acid

To a solution of 0.51 g (15 mmol) of methyl ester obtained in above (1) in dioxane (20 ml) was added 15 ml of 1 N hydrochloric acid. The mixture was refluxed for 1 hour. After cooling, the precipitated crystal was collected by filtration and washed with water. Subsequently, the obtained crystal was dissolved into saturated aqueous sodium bicarbonate and washed with ethyl acetate. The aqueous layer was acidified with 1N hydrochloric acid to pH 4 and extracted with ethyl acetate. The extract was washed, dried, and concentrated to give a yellow powder. The powder was recrystallized from ethyl acetate-n-hexane to give 0.31 g of the title compound. Yield: 64%. m.p.:165–167° C.

NMR (d$_6$-DMSO) δ: 4.52 (2H, s), 6.90 (1H, s), 7.18–7.38 (7H, m), 7.44–7.52 (1H, m), 7.90–8.00 (1H, m), 12.4 (1H, brs), 13.8 (1H, brs). Elemental Analysis for C$_{19}$H$_{15}$NO$_4$ Calcd. (%):C,71.02; H,4.70; N,4.36. Found. (%):C,70.97; H,4.72; N,4.43.

EXAMPLE 86–90

The other ester derivatives (Ic, R=Me) and their corresponding carboxylic acids (R=H) were prepared in the same manner as Example 85. The structure and physical data of each compound were shown below.

TABLE 8-1

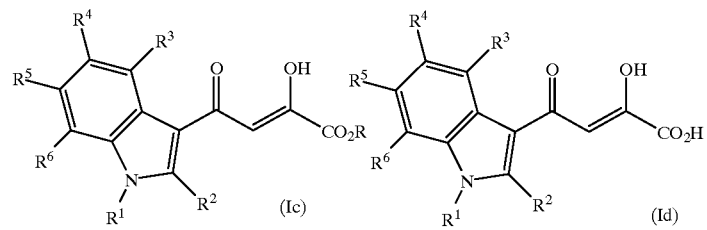

| | | | | | | | Recrystallization/m.p. (° C.) | |
|---|---|---|---|---|---|---|---|---|
| Example | R$^1$ | R$^2$ | R$^3$ | R$^4$ | R$^5$ | R$^6$ | ester (Ic, R = Me) | carboxylic acid (Id) |
| 86 | H | —CH$_2$Ph(4-F) | H | H | H | H | EtOAc—Hex 187–190 | EtOAc—Hex 168–170 |
| 87 | H | Ph(2-Cl) | H | Cl | H | H | EtOAc—Hex 224–226 | EtOAc—Hex 230–235 |
| 88 | H | Ph(2-F) | H | Cl | H | H | EtOAc—Hex 225–227 | EtOAc—Hex 203–208 |
| 89 | H | —COPh | H | Cl | H | H | EtOAc—Hex 207–210 | CHCl$_3$ 190–193 |
| 90 | H | Bu | H | H | H | H | oil | toluene 172–173 |

TABLE 8-2

| Example | Ic | Id |
|---|---|---|
| 86 | (d$_6$-DMSO)δ: 3.84(3H, s), 4.50(2H, s), (3.86(1H, s), 7.18(2H, t, J=9.0Hz), 7.21–7.40(5H, m), 7.46–7.55(1H, m), 792–8.00(iH, m). | (d$_6$-DMSO)δ: 4.50(2H, s), 6.89(1H, s), 7.14(2H, t, J=7.5Hz), 7.20–7.30(2H, m), 7.30–7.38(2H, m), 7.44–7.52(1H, m), 7.86–7.98(1H, m), 12.4(1H, s), 13.9(1H, brs). |
| 87 | (d$_6$-DMSO)δ: 3.65(3H, S), 5.95(1H, s), 7.36(1H, dd, J=8.6Hz, 2.0Hz), 7.50–7.80(5H, m), 8.30(1H, d, J=2.0Hz), 12.9(1H, brs). | (d$_6$-DMSO)δ: 5.98(1H, s), 7.35(1H, dd, J=10.2Hz, 1.6Hz), 7.46·7.80(5H, m), 8.29(1H, s), 12.8(1H, s), 13.4(1H, brs). |
| 88 | (d$_6$-DMSO)δ: 3.67(3H, s), 6.15(1H, s), 7.35(1H, dd, J=7.0Hz, 1.6Hz), 7.40–7.60(3H, m), 7.62–7.82(2H, m), 8.27(1H, d, J=1.6Hz), 12.9(1H, brs). | (d$_6$-DMSO)δ: 6.15(1H, s), 7.35(1H, dd, J=6.3Hz, 2.4Hz), 7.40–7.58(3H, m), 7.62–7.76(2H, m), 8.24(1H, d, J=1.6Hz), 12.8(1H, s), 13.6(1H, brs). |

TABLE 8-2-continued

| Example | Ic | Id |
|---|---|---|
| 89 | ($d_6$-DMSO)δ: 3.77(3H, s), 6.47(1H, s), 7.45(1H, dd, J=8.0Hz, 1.2Hz), 7.50–7.96(6H, m), 8.14(1H, s), 13.2(1H, brs) | ($d_6$-DMSO)δ: 6.56(1H, s), 7.31(1H, dd, J=7.8Hz, 2.1Hz), 7.42–7.54(4H, m), 7.62(1H, t, J=7.8Hz), 7.86(2H, d, J=6.9Hz), 8.12(1H, d, J=2.1Hz), 12.5(1H, s). |
| 90 | ($d_6$-DMSO)δ: 0.94(3H, t, J=7.2Hz), 1.30–1.49(2H, m), 1.65–1.80(2H, m), 3.12(2H, t, J=7.2Hz), 6.87(1H, s), 7.19–7.24(2H, m), 7.42–7.47(1H, m), 7.93–7.98(1H, m), 12.3(1H, s), 13.8(1H, brs). | |

TABLE 8-3

| Example | Ic | Id |
|---|---|---|
| 86 | $C_{20}H_{16}FNO_4$ 0.2$H_2O$<br>Calcd.(%): C, 67.30; H, 4.63; N, 3.92; F, 5.32.<br>Found.(%): C, 67.07; H, 4.63; N, 3.81; F, 5.24. | $C_{19}H_{14}FNO_4$ 0.1$H_2O$<br>Calcd.(%): C, 66.90; H, 4.20; N, 4.11; F, 5.57.<br>Found.(%): C, 66.91; H, 4.21; N, 4.15; F, 5.57. |
| 87 | $C_{19}H_{13}Cl_2NO_4$ 0.1$C_4H_8O_2$<br>Calcd.(%): C, 58.39; H, 3.49; N, 3.51; Cl, 17.77.<br>Found.(%): C, 58.08; H, 3.47; N, 3.45; Cl, 17.73. | $C_{18}H_{11}Cl_2NO_4$<br>Calcd.(%): C, 57.47; H, 2.95; N, 3.72; Cl, 18.85.<br>Found.(%): C, 57.38; H, 3.02; N, 3.65; Cl, 18.56. |
| 88 | $C_{19}H_{13}ClFNO_4$<br>Calcd.(%): C, 61.06; H, 3.51; N, 3.75; Cl, 9.49; F, 5.08.<br>Found.(%): C, 61.10; H, 3.59; N, 3.73; Cl, 9.26; F, 5.06. | $C_{18}H_{11}ClFNO_4$<br>Calcd.(%): C, 60.10; H, 3.08; N, 3.82; Cl, 9.86; F, 5.28.<br>Found.(%): C, 59.66; H, 3.24; N, 3.84; Cl, 9.66; F, 5.12. |
| 89 | $C_{20}H_{14}ClNO_5$<br>Calcd.(%): C, 62.59; H, 3.68; N, 3.65; Cl, 9.24.<br>Found.(%): C, 62.51; H, 3.74; N, 3.69; Cl, 9.15. | $C_{19}H_{12}ClNO_5$ 0.1$CHCl_3$<br>Calcd.(%): C, 60.10; H, 3.20; N, 3.67.<br>Found.(%): C, 60.23; H, 3.42; N, 3.71. |
| 90 | | $C_{16}H_{17}NO_4$<br>Calcd.(%): C, 66.89; H, 5.96; N, 4.88.<br>Found, (%): C, 66.88; H, 5.98; N, 4.92. |

EXAMPLE 91

4-(5-Chloroindol-3-yl)-2-hydroxy-4-oxo-2-butenoic acid diphenylmethyl ester

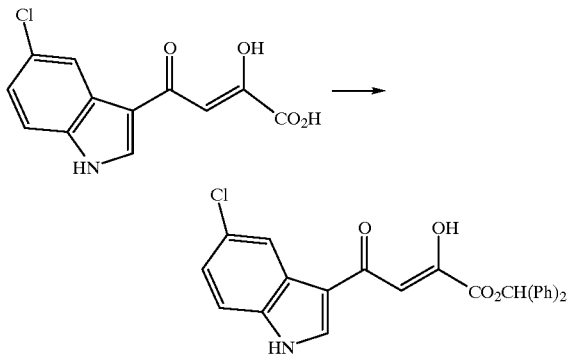

To a solution of 0.69 g (2.6 mmol) of 4-(5-chloroindol-3-yl)-2-hydroxy-4-oxo-2-butenoic acid obtained in above Example 1 in THF (14 ml) was added 0.76 g (3.9 mmol) of diphenyl diasomethane. The mixture was stirred for 30 minutes at room temperature. Furthermore to the mixture was added 0.25 g (1.3 mmol) of diphenyl diazomethane. The mixture was stirred for 1 hour at room temperature and refluxed for 30 minutes. The solvent was removed and the obtained crystal was washed with diisopropyl ether to give 0.93 g of the titled compound. Yield: 82%.

m.p.: 165-168° C. (decomposition). NMR ($d_6$-DMSO) δ: 7.02 (1H, s), 7.12 (1H, s), 7.28–7.59 (12H, m), 8.21 (1H, d, J=1.8 Hz), 8.87 (1H, s), 12.8 (1H, brm). Elemental Analysis (for $C_{25}H_{18}ClN_2O_4$) Calcd. (%):C,69.53; H,4.20; N,3.24; Cl,8.21. Found. (%):C,69.60; H,4.18; N,3.28; Cl,8.17.

EXAMPLE 92

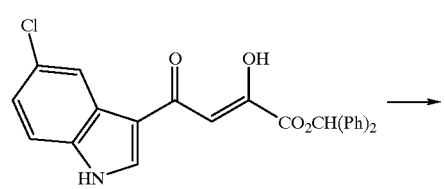

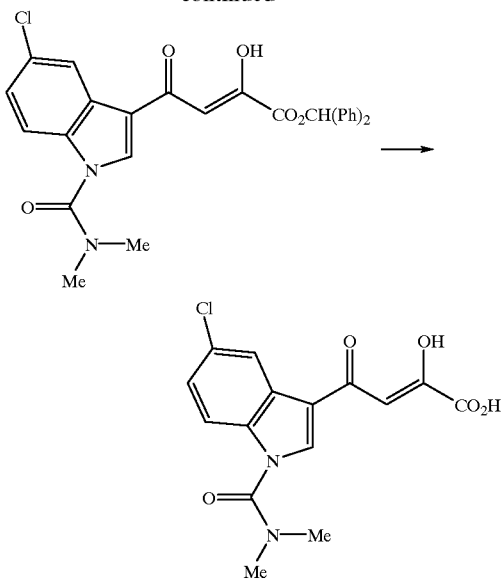

(1) 4-[1-(N,N-dimethylcarbamoyl)-5-chloroindol-3-yl]-2-hydroxy-4-oxo-2-butenoic acid diphenylmethyl ester To a solution of 0.432 g (1 mmol) of diphenylmethyl ester obtained in Example 91 in THF (5 ml) was added under ice-cooling, 88 mg (2.2 mmol) of sodium hydride (60% dispersion in mineral oil). The mixture was stirred for 30 minutes at room temperature. Subsequently, to the mixture was added 110 μl (1.2 mmol) of dimethylcarbamoyl chloride under ice-cooling and stirred for 1 hour at room temperature. The reaction mixture was poured into aqueous ammonium chloride and extracted with ethyl acetate. The extract was washed with water and dried. The solvent was removed and the residue was crystallized from ether. The crystal was collected by filtration and washed with ether to give 0.39 g of the titled compound. Yield: 77%.

m.p.: 178–183° C. (decomposition). NMR (d$_6$-DMSO) δ: 3.11 (6H, s), 6.88 (1H, s), 7.06 (1H, s), 7.30–7.52 (12H, m), 8.05 (1H, s), 8.39 (1H, d, J=1.8 Hz). Elemental Analysis for C$_{28}$H$_{23}$ClN$_2$O$_5$ 0.4H$_2$O Calcd. (%):C,65.92; H,4.70; N,5.49; Cl,6.95. Found. (%):C,65.90; H,4.80; N,5.83; Cl,6.92.

(2) 4-[1-(N,N-dimethylcarbamoyl)-5-chloroindol-3-yl]-2-hydroxy-4-oxo-2-butenoic acid To a solution of 356 mg (0.7 mmol) of the ester derivative obtained in above (1) in dichloromethane (3.6 ml) was added under ice-cooling, 0.5 ml of trifluoroacetic acid. The mixture was stirred for 30 minutes under ice-cooling. The reaction solution was concentrated under reduced pressure. The residues was dissolved in ethyl acetate. The ethyl acetate was washed successively with water and brine, and then dried. The obtained residue was crystallized from ether and recrystallized from 95% ethanol to give 0.16 g of the titled compound. Yield: 67%.

m.p.: 200–206° C. (decomposition). NMR (d$_6$-DMSO) δ: 3.06 (6H, s), 7.12 (1H, brs), 7.42 (1H, dd, J=9.0 Hz, 2.1 Hz), 7.66 (1H, d, J=9.0 Hz), 8.28 (1H, d, J=2.1 Hz), 9.06 (1H, s), 13.8 (1H, brs). Elemental Analysis for C$_{15}$H$_{13}$ClN$_2$O$_5$ Calcd. (%):C,53.50; H,3.89; N,8.32; Cl,10.53. Found. (%):C,53.28; H,3.92; N,8.25; Cl,10.34.

EXAMPLE 93

The following compounds were prepared in accordance with Example 92.

(1) 4-[5-Chloro-1-(4-fluorobenzoyl)-indol-3-yl]-2-hydroxy-4-oxo-2-butenoic acid diphenylmethyl ester m.p.: 198–200° C. (recrystallized from ether) NMR (CDCl$_3$) δ: 6.77 (1H, s), 7.00 (1H, s), 7.26–7.46 (13H, m), 7.77–7.82 (2H, m), 7.98 (1H, s), 8.21 (1H, d, J=8.7 Hz), 8.39 (1H, d, J=2.1 Hz). Elemental Analysis for C$_{32}$H$_{21}$ClFNO$_5$ Calcd. (%):C,69.38; H,3.82; N,2.53; Cl,6.40; F,3.43. Found. (%):C,69.22; H,3.91; N,2.79; Cl,6.47; F,3.66.

(2) 4-[5-Chloro-1-(4-fluorobenzoyl)-indol-3-yl]-2-hydroxy-4-oxo-2-butenoic acid m.p.: 213–218° C. (recrystallized from ethyl acetate) NMR(d$_6$-DMSO) δ:7.11 (1H, s), 7.50 (2H, t J=8.7 Hz), 7.55 (1H, dd, J=8.7 Hz, 2.4 Hz), 7.94–7.99 (2H, m), 8.23 (1H, d, J=8.7 Hz), 8.34 (1H, d, J=2.4 Hz), 8.86 (1H, s). Elemental Analysis for C$_{19}$H$_{11}$ClFNO$_5$ Calcd. (%):C,58.72; H,2.88; N,3.60; Cl,9.12; F,4.89. Found. (%):C,58.97; H,3.10; N,3.75; Cl,8.84; F,5.15.

EXAMPLE 94

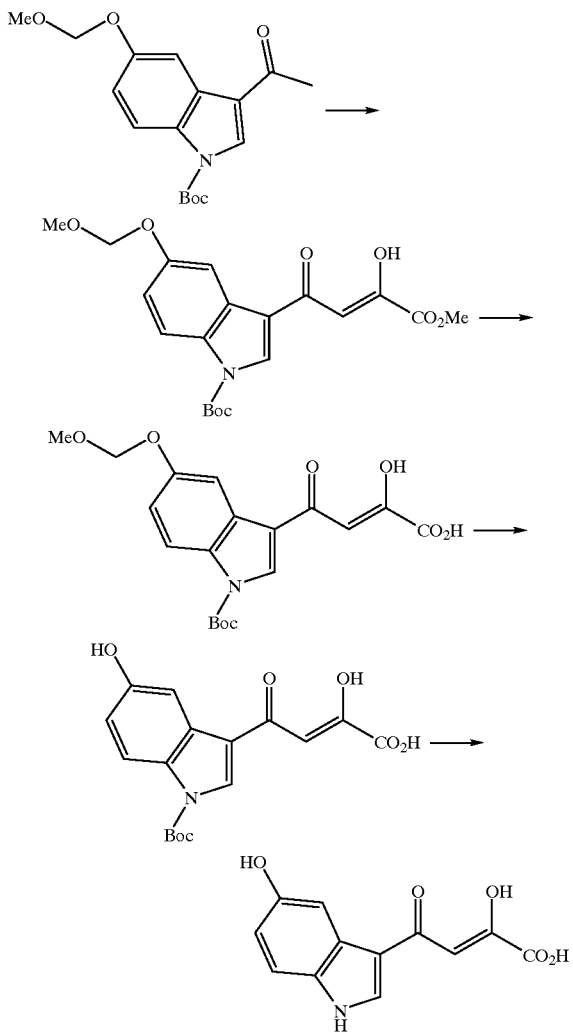

(1) 4-(1-tert-Butoxycarbonyl-5-methoxymethyloxy-indol-3-yl)-2-hydroxy-4oxo-2-butenoic acid methyl ester Starting from 3-acetyl-1-tert-butoxycarbonyl-5-methoxymethyloxy-indole obtained in the reference example 5, the titled compound was prepared according to the method described in Example 85.

NMR(CDCl$_3$) δ: 1.72 (9H, s), 3.53 (3H, s), 3.95 (3H, s), 5.27 (2H, s), 6.91 (1H, s), 7.12 (1H, dd, J=9.0 Hz, 2.6 Hz), 8.02–8.07 (2H, m), 8.32 (1H, s).

(2) 4-(1-tert-Butoxycarbonyl-5-methoxymethyloxy-indol-3-yl)-2-hydroxy-4-oxo-2-butenoic acid To a solution of 0.345 g (0.85 mmol) of the ester derivative obtained in above (1) in dioxane (7 ml) was added 1.7 ml of 1 N lithium hydroxide. The mixture was stirred for 1.5 hours at room temperature. The solvent was removed under reduced pressure at room temperature and the residue was dissolved in water. The aqueous layer was washed twice with ethyl acetate and neutralized with 1 N hydrochloric acid (1.7 ml) and extracted with ethyl acetate. The organic layer was washed with water and brine, and then dried. The solvent was removed and the obtained crystal was washed with ethyl acetate to give 0.28 g of the titled compound. Yield: 84%. m.p.: 165–170° C. (decomposition)

NMR (d$_6$-DMSO) δ: 1.67 (9H, s), 3.42 (3H, s), 5.25 (2H, s), 7.15 (1H, s), 7.20 (1H, dd, J=9.0 Hz, 2.6 Hz), 7.95 (1H, d, J=2.6 Hz), 8.04 (1H, d, J=9.0 Hz), 8.86 (1H, s).

(3) 4-(1-tert-Butoxycarbonyl-5-hydroxy-indol-3-yl)-2-hydroxy-4-oxo-2-butenoic acid To a solution of 0.25 g (0.64 mmol) of carboxylic acid obtained in above (2) in THF (3 ml) and isopropyl alcohol (1.5 ml) was added 0.25 ml of concentrated hydrochloric acid. The mixture was stirred for 16 hours at room temperature. The reaction solution was concentrated under reduced pressure. The obtained residue was dissolved in ethyl acetate. The ethyl acetate was washed with brine and dried. The solvent was removed and the obtained crystal was recrystallized from ethyl acetate to give 0.12 g of the titled compound. Yield: 43% m.p.: 210–214° C. (decomposition)

NMR (d$_6$-DMSO) δ: 1.18 (3H, t J=7.2 Hz), 1.66 (9H, s), 1.99 (3H, s), 4.02 (2H, q, J =7.2 Hz), 6.89 (1H, dd, J=9.0 Hz, 2.6 Hz), 7.10 (1H, s), 7.69 (1H, d, J=2.6 Hz), 7.92 (1H, d, J =9.0 Hz), 8.76 (1H, s), 9.50 (1H, 5). Elemental Analysis for C$_{17}$H$_{17}$NO$_7$ C$_4$H$_8$O$_2$ Calcd. (%):C,57.93; H,5.79; N,3.22. Found. (%):C,57.86; H,5.76; N,3.45.

(4) 2-Hydroxy-4-(5-hydroxy-indol-3-yl)-4-oxo-2-butenoic acid

To trifluoroacetic (4 ml) acid was added 0.2 g (0.45 mmol) of 4-(1-tert-butoxycarbonyl-5-hydroxy-indol-3-yl)-2-hydroxy-4-oxo-2-butenoic acid obtained in above (3). The mixture was stirred for 3.5 hours at room temperature. The reaction mixture was concentrated under reduced pressure. The obtained residue was dissolved in aqueous sodium bicarbonate. The water layer was washed twice with ethyl acetate and acidified with hydrochloric acid to pH 3, and then extracted with ethyl acetate. The organic layer was washed with brine and dried. The solvent was removed and the obtained crystal was recrystallized from ethanol to give 70 mg of the titled compound. Yield: 49%. m.p.: 220–225° C. (decomposition)

NMR (d$_6$-DMSO) δ: 6.75 (1H, dd, J=8.8 Hz, 2.4 Hz), 6.95 (1H, s), 7.20 (1H, d, J=2.4 Hz), 7.29 (1H, d, J=8.8 Hz), 8.56 (1H, d, J=3.2 Hz), 9.15 (1H, brm), 12.2 (1H, s). Elemental Analysis for C$_{12}$H$_9$NO$_5$ Calcd. (%):C,58.30; H,3.67; N,5.67. Found. (%):C,58.20; H,3.85; N,5.84.

EXAMPLE 95

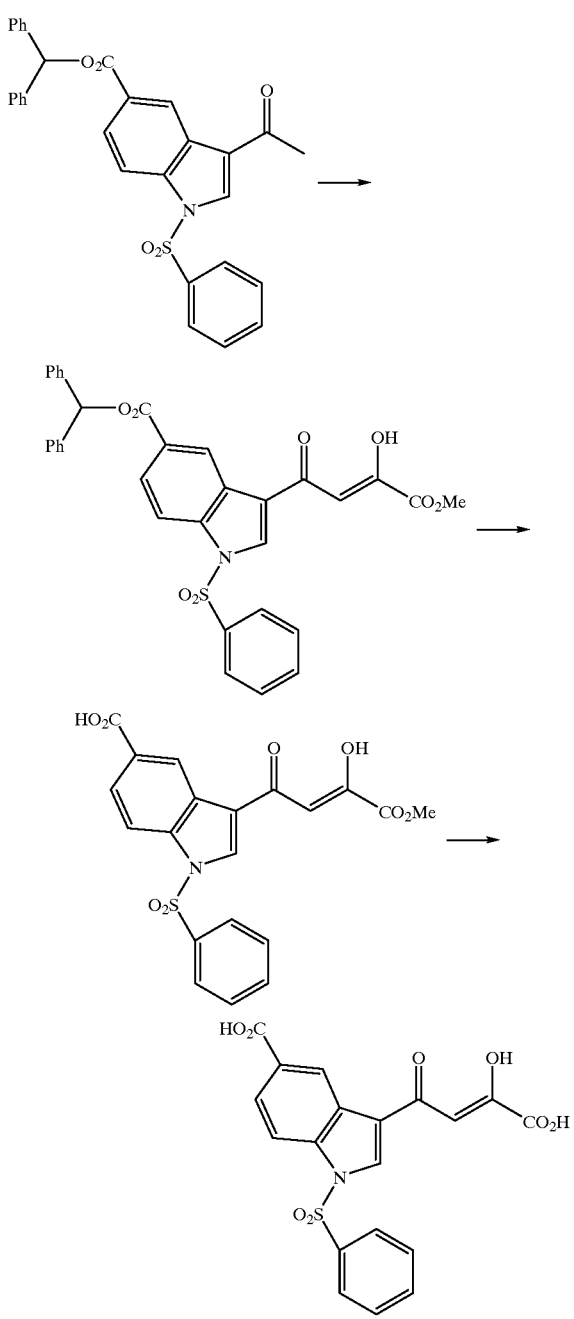

(1) 4-(1-Benzenesulfonyl-5-carboxy-indol-3-yl)-2-hydroxy-4-oxo-2-butenoic acid methyl ester (a) Starting from 3-acetyl-1-benzenesulfonyl-indol-5-carboxylic acid diphenyl ester obtained in the reference example 2, 4-(1-Benzenesulfonyl-5-diphenylmethyloxycarbonyl-indol-3-yl)-2-hydroxy-4-oxo-2-butenoic acid methyl ester was prepared according to the method described in Example 85.

NMR(CDCl$_3$) δ: 3.97 (3H, s), 6.93 (1H, 3), 7.15 (1H, 5), 7.26–7.67 (13H, m), 7.96–7.99 (2H, m), 8.04 (1H, d, J=8.0 Hz), 8.20 (1H, dd, J=8.0 Hz, 1.8 Hz), 8.39 (1H, s), 9.13 (1H, d, J=1.8 Hz).

(b) To a solution of 237 mg (0.4 mmol) of the above described compound and 86 mg (0.8 mmol) of anisole in dichloromethane (2.4 ml) was added under ice-cooling, 0.3 ml of trifluoroacetic acid. Subsequently, the mixture was stirred for 1 hour at room temperature. The reaction mixture was concentrated under reduced pressure. The obtained residue was washed with ether to give 125 mg of the titled compound (1). Yield: 73%. m.p.: 222–232° C. (decomposition)

NMR (d$_6$-DMSO) δ: 3.89 (3H, s), 7.38 (1H, s), 7.63–8.28 (7H, m), 8.90 (1H, d, J=1.4 Hz), 9.42 (1H, s). Elemental Analysis for C$_{20}$H$_{15}$NO$_8$S Calcd. (%):C,55.94; H,3.52; N,3.26; S,7.47. Found. (%):C,55.97; H,3.74; N,3.37; S,7.32.

(2) 4-(1-Benzenesulfonyl-5-carboxy-indol-3-yl)-2-hydroxy-4-oxo-2-butenoic acid

The titled compound was prepared from the ester derivative obtained in above (1) in a manner similar to that described in with Example 23.

m.p.: 224–228° C. (decomposition) NMR (d$_6$-DMSO) δ: 7.31 (1H, s), 7.65–7,82 (4H, m), 8.03 (1H, dd, J=9.0 Hz, 1.8 Hz), 8.13 (1H, d, J=9.0 Hz), 8.23 (1H, d, J=7.6 Hz), 8.89 (1H, d, J=1.8 Hz), 9.35 (1H, s). Elemental Analysis for C$_{19}$H$_{13}$NO$_8$S 0.15H$_2$O Calcd. (%):C,54.59; H,:3.21; N,3.35; S,7.67. Found. (%):C,54.85; H,3.53; N,3.45; S,7.53.

The compounds in Example 96–101 were prepared in accordance with the following route.

was gradually warmed to room temperature. The mixture was cooled again to −78° C. and treated with 525 mg (3.6 mmol) of phthalic anhydride. The reaction solution was warmed to room temperature and mixed with ice water. The solution was acidified with 1N hydrochloric acid and extracted with ethyl acetate. The extract was washed with water and dried, and then concentrated. The obtained residue was crystallized from ethyl acetate-n-hexane to give 362 mg of the titled compound. Yield: 30%.

NMR (CDCl$_3$) δ: 1.68 (9H, s), 6.99 (1H, s), 7.20–7.50 (2H, m), 7.50–7.88 (4H, m), 7.94–8.38 (2H, m), 8.60–8.80 (1H, m), 13.2 (1H, brs).

m.p.: 138–141° C. NMR (d$_6$-DMSO) δ:7.11 (1H, s), 7.51–7.87 (7H, m), 8.05–8.21 (5H, m), 8.94 (1H, s), 10.3 (1H, brs). Elemental Analysis for C$_{23}$H$_{21}$NO$_6$ 0.3H$_2$O Calcd. (%):C,66.92; H,5.27; N,3.39. Found. (%):C,66.81; H,5.31; N,3.43.

EXAMPLE 97

1-(1-Benzenesulfonyl-5chloroindol-3-yl)-3-(1-carboxyphenyl)-3-hydroxy-propen-1-one was prepared in accordance with Example 96.

NMR (d$_6$-DMSO) δ:7.10 (1H, s), 7.49–8.25 (11H, m), 9.02 (1H, s), 9.23 (1H, s), 13.2 (1H, brs). Elemental Analysis

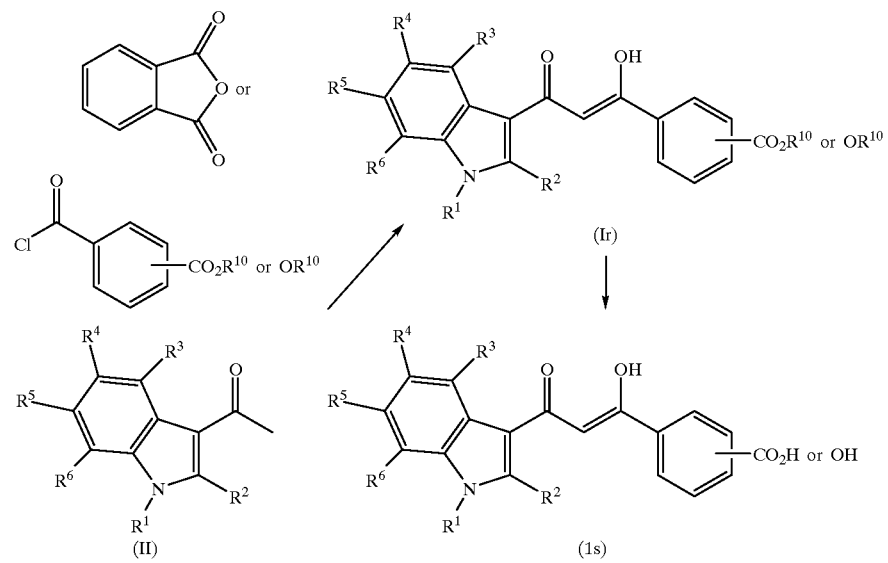

EXAMPLE 96

1-(1-tert-Butoxycarbonyl-indol-3-yl)-3-(1-carboxyphenyl)-3-hydroxy-propen-1-one

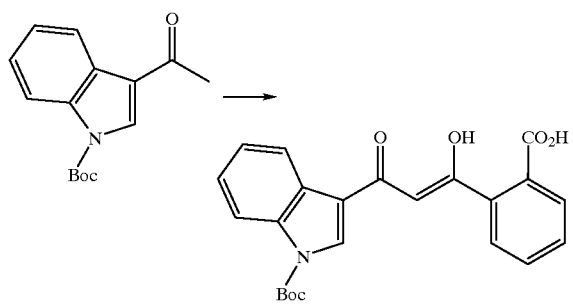

To a solution of 777 mg (3 mmol) of 3-acetyl-1-tert-butoxycarbonyl-indole in THF (10 ml) was added 3.6 ml (3.6 mmol) of 1M LHMDS in THF at −78° C. The mixture for C$_{26}$H$_{16}$ClNO$_6$S Calcd. (%):C,59.82; H,3.35; N,2.91; Cl,7.36; S,6.65. Found. (%):C,59.89; H,3.51; N,2.88; Cl,7.22; S,6.73.

EXAMPLE 98

1-(Indol-3-yl)-3-(1-carboxyphenyl)-3-hydroxy-prppen-1one

The titled compound was prepared by the hydrolysis of 1-(1-tert-butoxycarbonyl-indol-3-yl)-3-(1-carboxylphenyl)-3-hydroxy-propen-1-one obtained in above Example 96 with hydrochloric acid.

m.p.: 175–177° C. (decomposition) NMR (d$_6$-DMSO) δ: 6.73 (1H, s), 7.16–7.32 (2H, m), 7.40–7.86 (5H, m), 7.88–8.28 (1H, m), 8.34–8.60 (1H, m), 11.8–12.3 (1H, brs), 12.5 (1H, brs). Elemental Analysis for C$_{18}$H$_{13}$NO$_4$ Calcd. (%):C,70.35; H,4.26; N,4.56. Found. (%):C,70.21; H,4.43; N,4.58.

EXAMPLE 99

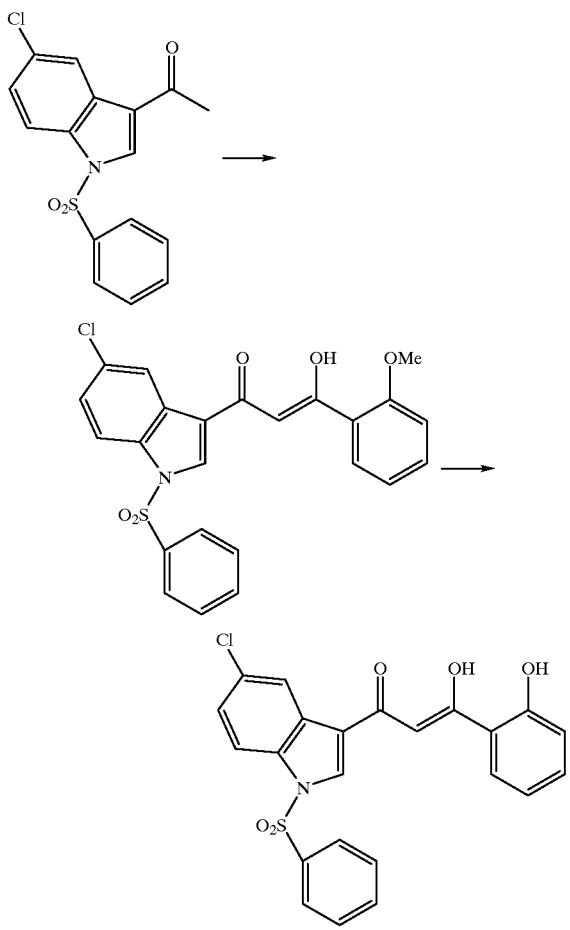

(1) 1-(1-Benzensulfonyl-5-(chloroindol-3-yl)-3-(2-methoxyphenyl)-propan-1,3-dione A solution of 500 mg (1.5 mmol) of 3-acetyl-1-benzenesulfonyl-5-chloroindole in THF (5 ml) was cooled at −78° C. Subsequently, to the reaction mixture was added 1.8 ml (1.8 mmol) of 1M LHMDS in THF. The solution was gradually warmed to 0° C. and cooled again to −78° C. To the solution was added 310 mg (1.8 mmol) of 2-methoxybenzoylchloride. The reaction mixyure was warmed to room temperature. Alter 30 minutes, the mixture was treated with water and acidified with 6 N hydrochloric acid. The mixture was extracted with ethyl acetate and washed with water, and then dried. The solvent was removed and the obtained residue was chromatographed on silica gel with ethyl acetate-n-hexane as eluent. The fraction of the objective was concentrated to give 160 mg of the titled compound as a foam. Yield: 23%.

NMR (CDCl$_3$) δ:4.04 (3H, s), 4.55 (2H, s), 7.02 (13H, m).

(2) 1-(1-Benzenesulfonyl-5-chloroindol-3-yl)-3-hydroxy-3-(2-hydroxyphenyl)-propen-1-one To a solution of 0.1 g (0.2 mmol) of the compound obtained in above (1) in chloroform (3 ml) was added 1 ml (7 mmol) of trimethylsilyl iodide. The reaction mixture was stirred at 40° C. for 4 hours. After cooling, an aqueous a sodium thiosulfate was added to the reaction mixture. The solution was neutralized with an aqueous sodium bicarbonate and extracted with ethyl acetate. The extract was washed with water, dried, and then removed. The obtained crystal was collected by filtration and washed with ethyl acetate-isopropylether. Recrystallization from THF gave 23 mg of the titled compound. Yield 24%.

m.p.: 241–244° C. NMR (d$_6$-DMSO) δ: 7.11 (1H, s), 7.51–7.87 (7H, m), 8.05–8.21 (5H, m), 8.94 (1H, s), 10.3 (1H, brs). Elemental Analysis for C$_{23}$H$_{16}$ClNO$_5$S 0.5C$_4$H$_8$O Calcd. (%):C,61.29; H,4.11; N,2.86; Cl,7.23; S,6.54. Found. (%):C,61.48; H,3.94; N,3.20; Cl,7.42; S,6.77.

EXAMPLE 100

1-(1-Benzenesulfonyl-5-chloroindol-3-yl)-3-(3-carboxyphenyl)-3-hydroxy-propen-1-one In accordance with Example 99, 3-acetyl-1-benzenesulfonyl-5-chloroindole reacted with 3-methoxycarbonyl benzoylchloride, followed by hydrolysis with hydrochloric acid to give the titled compound.

m.p.: 245–255° C. (decomposition) NMR (d$_6$-DMSO) δ:6.80 (1H, brs), 7.40–7.80 (6H, m), 8.00–8.60 (6H, m), 9.60 (1H, brs). Elemental Analysis for C$_{24}$H$_{16}$ClNO$_6$S H$_2$O 0.5C$_4$H$_8$O$_2$ Calcd. (%):C,57.51; H,3.90; N,2.58; Cl,6.53; S,5.90. Found. (%):C,57.36; H,3.56; N,2.70; Cl,6.32; S,5.74.

EXAMPLE 101

1-(5-Chloroindol-3-yl)-3-(3-carboxyphenyl)-3-hydroxy-propen-1-one

The carboxylic acid in Example 100 was esterified to 1-(1-benzenesulfonyl-5-chloroindol-3-yl)-3-(3-methoxycarbonylphenyl)-3-hydroxy-propen-1-one. The compound was hydrolyzed with lithium hydroxide in methanol to give the tiled compound.

m.p.: >270° C. (decomposition) NMR (d$_6$-DMSO) δ: 6.60 (1H, brs), 7.00–7.60 (4H, m), 8.10–8.70 (5H, m), 11.9 (1H, brs). Elemental Analysis for C$_{18}$H$_{12}$ClNO$_4$ 3.3H$_2$O Calcd. (%):C,53.88; H,4.67; N,3.49; Cl,8.84. Found. (%):C,53.96; H,4.09; N,3.44; Cl,7.68.

EXAMPLE 102

1-(5-Chloroindol-3-yl)-3-hydroxy-2-(3,5-dichlorophenylsulfenyl)-3-(2H-tetrazol-5-yl)-propenone

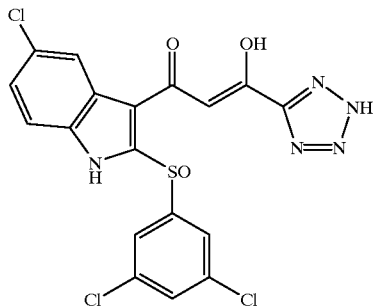

To a solution of 0.03 g (0.064 mmol) of 1-(5-chloroindol-3-yl)-3-hydroxy2-(3,5-dichlorophenylthio)-3-(2H-tetrazol-5-yl)-propenone in methanol (6 ml) was added dropwise 0.068 g of Oxone in water (0.2 ml). The solution was stirred for 18 hours. The solvent was removed under reduced pressure. The residue was dissolved in ethyl acetate and the ethyl acetate was washed with water, and dried. The solvent was removed and the residue was crystallized from ether, and then recrystallized from ethyl acetate to give the titled compound.

m.p.: 200–204° C. (decomposition) Recrystallized from EtOAc Elemental Analysis for $C_{18}H_{10}Cl_3N_5O_3S \cdot H_2O$ Calcd. (%):C,43.17; H,2.42; N,13.99; Cl,21.24; S,6.40. Found. (%):C,43.04; H,2.66; N,13.85; Cl,20.74; S,6.36. NMR($d_6$-DMSO) δ:7.13 (1H, s), 7.45 (1H, dd, J=9.0 Hz, 2.1 Hz), 7.67 (1H, d, J=9.0 Hz), 7.84 (1H, t J=1.8 Hz), 7.97 (2H, d, 1.8 Hz), 7.99(1H, d, J=2.1 Hz), 13.5 (1H, s).

EXAMPLE 103

2-Benzenesulfonyl-1-(5-chloroindol-3-yl)-3-hydroxy-3-(2H-tetrazol-5-yl)-propenone

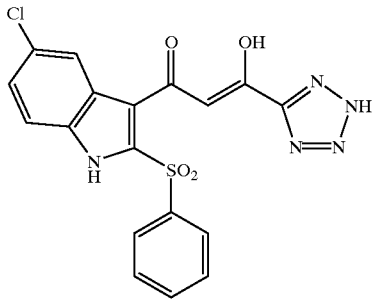

(1) To a solution of 1.15 g of 2H-tetrazole-5-carboxylic acid ethyl ester in dichloromethane (12 ml) were added 1.02 g of dihypropyrane and 0.1 g of pyridinium p-toluene sulfonate. The mixture was stirred for 2 hours at room temperature and poured into an aqueous sodium bicarbonate. The mixture was extracted with ethyl acetate. The extract was washed with brine, and dried. The solvent was removed to give an oil which was a mixture of 1-tetrahydropyranyl-1H-tetrazole-5-carboxylic acid ethyl ester and 2-tetrahydropyranyl-2H-tetrazole-5-carboxylicacid ethyl ester.

(2) 3-Acetyl-5-chloro-2-benzenesulfonyl-indol (0.167 g, 0.5 mmol) obtained in Example 9 reacted with 0.25 g (0.65 mmol) of the mixture obtained in above (1) in accordance with Example 67 to give the title compound.

m.p.: 219–222° C. (decomposition) Recrystallized from EtOAc Elemental Analysis for $C_{18}H_{12}ClN_5O_4S \cdot 0.3C_4H_8O_2$ Calcd. (%):C,50.54; H,3.18; N,15.35; Cl,7.77; S,7.03. Found. (%):C,50.64; H,3.49; N,15.11; Cl,7.56; S,6.81. NMR ($d_6$-DMSO) δ: 7.29 (1H, s), 7.47–7.78 (5H, m), 8.04 (1H, d, J=2.0 Hz), 8.08–8.14 (2H, m), 13.7 (1H, s).

EXAMPLE 104

1-(5-Chloroindol-3-yl)-3-hydroxy-3-(2H-tetrazol-5-yl)-propenone magnesium salt 1-(5-Chloroindol-3-yl)-3-hydroxy-3-(2H-tetrazol-5-yl)-propenone obtained in Example 67(2) was treated with 2 mole equivalent of 1N sodium hydroxide, and then the solution was mixed with excess amount of aqueous magnesium chloride. The obtained precipitate was collected by filtration and recrystallized from ethanol to the titled compound.

Elementary Analysis for $C_{12}H_6ClMgN_5O_2 \cdot 2H_2O$ Calcd. (%):C,41.42; H,2.90; N,20.12; Cl,10.19; Mg,6.98. Found. (%):C,42.88; H,2.97; N,20.74; Cl,10.37; Mg,6.87.

The compounds in Example 105–136 were prepared in accordance with the above-described Example. The structure and the physical data are shown below.

EXAMPLE 105

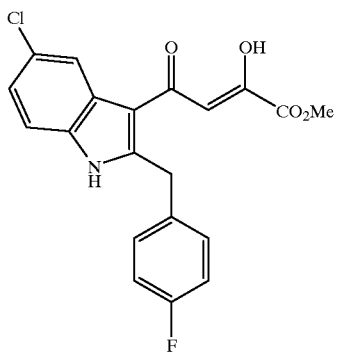

m.p.: 235–238° C. Recrystallized from EtOAc-THF Elemental Analysis for $C_{20}H_{15}ClFNO_4$ Calcd. (%):C,61.95; H,3.90; N,3.61; Cl,9.14, F;4.90. Found. (%):C,61.57; H,3.95; N,3.61; Cl8.90, F;4.70. NMR ($d_6$-DMSO) δ:3.84 (3H, s), 4.49 (2H, S), 6.74 (1H, s), 7.16 (2H, t, J=8.7 Hz), 7.25–7.34 (3H, m), 7.51 (1H, d, J=8.7 Hz), 7.99 (1H, d, J=2.1 Hz), 12.6 (1H, s).

EXAMPLE 106

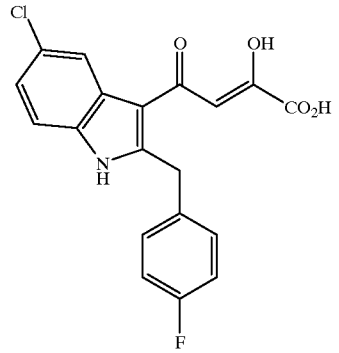

m.p.: 185–190° C. Recrystallized from EtOAc-THF Elemental Analysis for $C_{19}H_{13}ClFNO_4 \cdot 0.2C_4H_8O_2 \cdot 0.2C_4H_8O$ Calcd. (%):C,60.70; H,4.24; N,3.31; Cl,8.37, F;4.49. Found. (%):C,60.68; H,4.34; N,3.28; Cl,8.16, F;4.37. NMR ($d_6$-DMSO) δ: 4.49 (2H, S), 6.78 (1H, s), 7.15 (2H, t, J =8.7 Hz), 7.24–7.36 (3H, m), 7.50 (1H, d, J=8.7 Hz), 7.96 (1H, d, J=2.1 Hz), 13.5–14.0 (1H, brs).

EXAMPLE 107

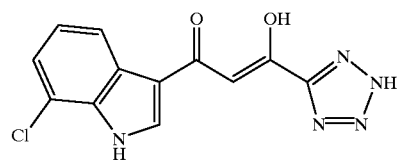

m.p.: >250° C. Recrystallized from EtOAc-$Et_2O$ Elemental Analysis for $C_{12}H_{18}ClN_5O_2 \cdot 0.25C_4H_8O_2$ Calcd. (%):C, 50.03; H,3.15; N,22.79; Cl,11.54. Found. (%):C,50.00; H,3.20; N,23.07; Cl,11.23. NMR ($d_6$-DMSO) δ: 7.24–7.41 (3H, m), 8.20 (1H, d, J=7.8 Hz), 8.86 (1H, d, J=3.2 Hz), 12.8 (1H, s).

EXAMPLE 108

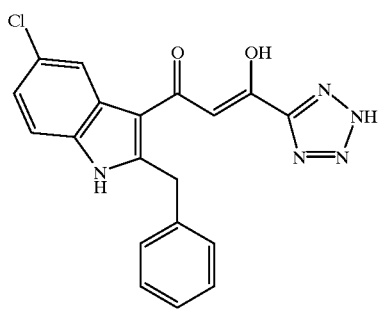

m.p.: 237–239° C. Recrystallized from THF-CHCl₃ Elemental Analysis for $C_{19}H_{14}ClN_5O_2$ 0.075CHCl₃ Calcd. (%):C,58.93; H,3.65; N,18.01; Cl,11.17. Found. (%):C, 58.58; H,3.76; N,17.93; Cl,11.25. NMR (d₆-DMSO) δ:4.54 (2H, s), 7.02 (1H, s), 7.21–7.33 (6H, m), 7.52 (1H, d, J=8.4 Hz), 8.02 (1H, d, J=1.8 Hz), 12.6 (1H, s).

EXAMPLE 109

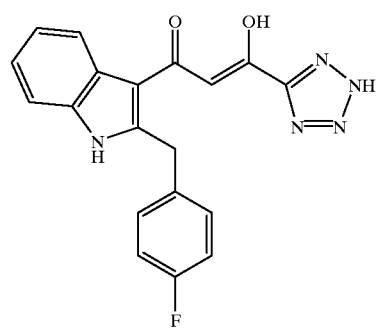

m.p.: 216–218° C. Recrystallized from CHCl₃ Elemental Analysis for $C_{19}H_{14}FN_5O_2$ 0.01CHCl₃ 0.25H₂O Calcd. (%):C,61.87; H,3.96; N,18.98; F,5.15. Found. (%):C,61.88; H,3.89; N,19.05; F,5.00. NMR (d₆-DMSO) δ: 4.54 (2H, 5), 7.11 (1H, s), 7.12–7.18 (2H, m), 7.25–7.31 (2H, m), 7.33–7.39 (2H, m), 7.49–7.52 (1H, m), 7.98–8.01 (1H, m), 12.4 (1H, s).

EXAMPLE 110

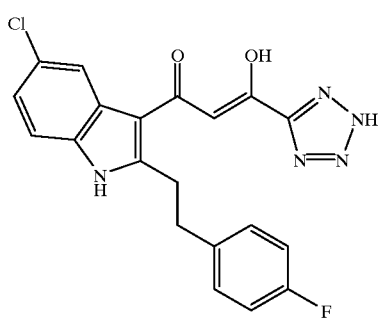

m.p.: 205–207° C. Recrystallized from Et₂O Elemental Analysis for $C_{20}H_{15}ClFN_5O_2$ 0.2C₄H₁₀O 0.2H₂O Calcd. (%):C,58.07; H,4.08; N,16.28; Cl,8.24; F,4.42. Found. (%):C,58.00; H,4.25; N,16.22; Cl,8.08; F,4.28. NMR(d₆-DMSO) δ: 3.03–3.10 (2H, m), 3.37–3.44 (2I-1, m), 7.01 (1H, s), 7.11 (2H, t J=8.7 Hz), 7.28 (1H, dd, J=8.6 Hz, 2.1 Hz), 7.30–7.36 (2H, m), 7.51 (1H, d, J=8.6 Hz), 8.00 (1H, d, J=2.1 Hz), 12.5 (1H, s).

EXAMPLE 111

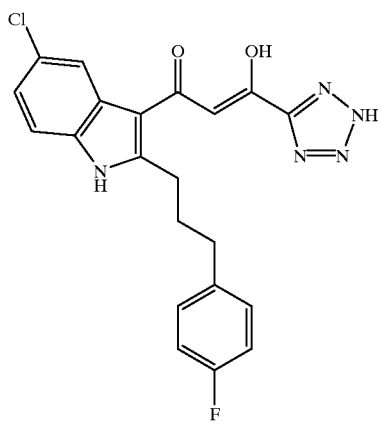

m.p.: 181–182° C. (decomposition) Recrystallized from MeOH-Et₂O Elemental Analysis for $C_{21}H_{17}ClFN_5O_2$ 0.4CH₄O Calcd. (%):C,58.59; H,4.27; N,15.97; Cl,8.08; F,4.33. Found. (%):C,58.39; H,4.29; N, 16.15; Cl,8.36; F, 4.31. NMR (d₆-DMSO) δ: 2.07 (2H, m), 2.75 (2H, t, J=7.2 Hz), 3.18 (2H, t, J=7.0 Hz), 6.98 (1H, s), 7.04–7.33 (5H, m), 7.49 (1H, d, J=8.6 Hz), 8.00 (1H, s), 12.5 (1H, s).

EXAMPLE 112

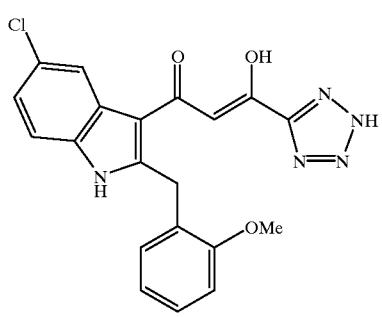

m.p.: 245° C. (decomposition) Recrystallized form EtOAc-Et₂O Elemental Analysis for $C_{20}H_{16}ClN_5O_3$ Calcd. (%):C,58.61; H,;3.93; N,17.09; Cl8.65. Found. (%):C,58.36; H,4.30; N,16.75; Cl8.15. NMR (d₆-DMSO) δ: 3.86 (3H, s), 4.47 (2H, s), 6.83–6.93 (3H, m), 7.06 (1H, d, J=8.4 Hz), 7.23–7.31 (2H, m), 7.51 (1H, d, J=8.6 Hz), 8.07 (1H, s), 12.3 (1H, s).

EXAMPLE 113

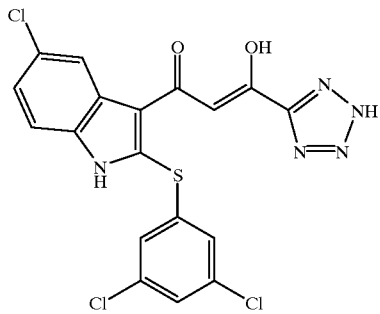

m.p.: 225–227° C. (decomposition) Recrystallized from EtOAc Elemental Analysis for $C_{18}H_{10}Cl_3N_5O_2S$ $0.2C_4H_8O_2$ Calcd. (%):C,46.62; H,2.41; N,14.46; Cl,21.96; S,6.62. Found. (%):C,46.36; H,2.66; N,14.52; Cl,21.64; S,6.56. NMR ($d_6$-DMSO) δ: 7.06–7.10 (1H, m), 7.32–7.70 (6H, m), 8.15 (1H, d, J=1.8 Hz), 12.7 (1H, s).

EXAMPLE 114

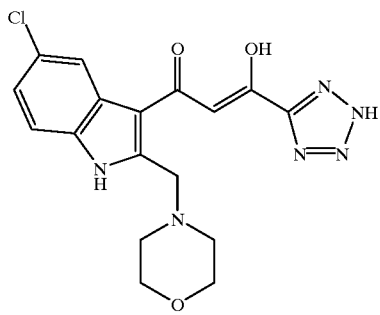

m.p.: 250–255° C. (decomposition) Recrystallized from EtOAc Elemental Analysis for $C_{17}H_{17}ClN_6O_3$ $0.2H_2O$ Calcd. (%):C,52.03; H,4.47; N,21.42; Cl,9.03. Found. (%):C,52.07; H,4.56; N,21.27; Cl,8.98. NMR($d_6$-DMSO) δ: 2.69 (2H, brm), 3.69 (2H, brm), 4.15 (2H, s), 7.30 (1H, dd, J=8.7 Hz, 2.1 Hz), 7.38 (1H, brs), 7.56 (1H, d, J=8.7 Hz), 8.08 (1H, d, J=2.1 Hz), 12.6 (1H, brs).

EXAMPLE 115

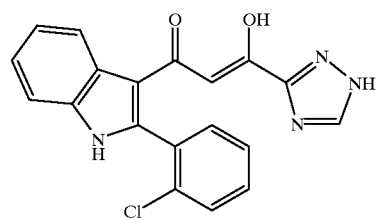

m.p.: 166–169° C. (decomposition) Recrystallized from EtoAc-Et$_2$O Elemental Analysis (or $C_{19}H_{13}ClN_4O_2$ $0.5C_4H_{10}O$ $0.2H_2O$ Calcd. (%):C,62.21; H,4.57; N,13.82; Cl,8.74. Found. (%):C,62.28; H,4.52; N,13.80; Cl,8.79. NMR ($d_6$-DMSO) δ: 6.37(1H, s), 7.29–7.31 (2H, m), 7.48–7.73 (5H, m), 8.22–8.26 (1H, m), 8,48 (1H, brs), 12.5 (1H, brs), 14.6 (1H, brs).

EXAMPLE 116

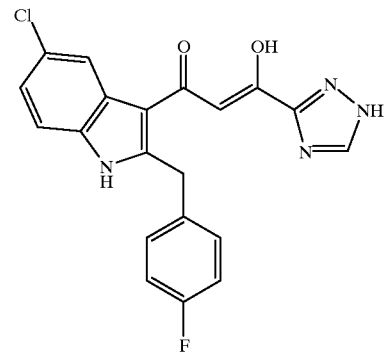

m.p.: 134–138° C. (decomposition) Recrystallized from EtOAc-Hex Elemental Analysis for $C_{20}H_{14}ClFN_4O_2$ $0.25C_4H_8O_2$ $0.25H_2O$ Calcd. (%):C,59.58; H,3.93; N,13.23; Cl,8.37; F,4.49. Found. (%):C,59.72; H,3.83; N,13.23; Cl,8.43; F,4.48. NMR ($d_6$-DMSO) δ: 4.51 (2H, s), 7.00 (1H, s), 7.12–7.18 (2H, m), 7.26 (1H, dd, J=8.7 Hz, 1.8 Hz), 7.35–7.40 (2H, m), 7.50 (1H, d, J=8.7 Hz), 7.95 (1H, d, J=1.8 Hz), 8.76 (1H, brs), 12.4 (1H, brs), 14.7 (1H, brs).

EXAMPLE 117

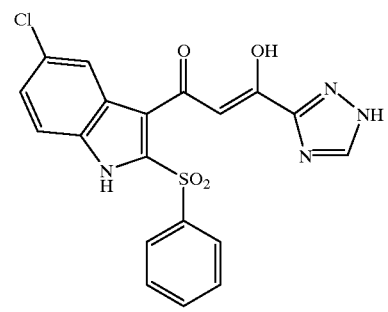

m.p.:185–187° C. (decomposition) Recrystallized from EtOAc Elemental Analysis for $C_{19}H_{13}ClN_4O_4S$ $0.2H_2O$ Calcd. (%):C,52.77; H,3.12; N,12.96; Cl,8.20; S,7.41. Found. (%):C,52.81; H,3.32; N,12.86; Cl,7.99; S,7.33. NMR ($d_6$-DMSO) δ: 7.22 (1H, s), 7.48 (1H, dd, J=8.7 Hz, 2.1 Hz), 7.60–7.77 (4H, m), 7.99 (1H, d, J=2.1 Hz), 8.08–8.14 (2H, m), 8.82 (1H, brs), 13.6 (1H, brs).

EXAMPLE 118

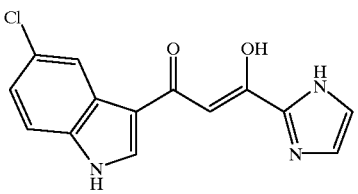

m.p.: 272–276° C. Recrystallized from EtOAc Elemental Analysis for $C_{14}H_{10}ClN_3O_2$ Calcd. (%):C,58.45; H,3.50; N,14.61; Cl,12.32. Found. (%):C,58.40; H,3.50; N,14.44; Cl,12.11. NMR ($d_6$-DMSO) δ: 7.02–7.47 (4H,m), 7.54 (1H, s), 8.14 (1H, d, J=1.8 Hz), 8.58 (1H, s), 12.3 (1H, brs), 13.2 (1H, brs).

EXAMPLE 119

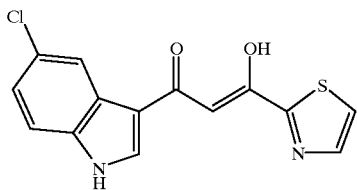

m.p.: 226–227° C. Recrystallized from MeOH Elemental Analysis for $C_{14}H_9ClN_2O_2S$ Calcd. (%):C,55.18; H,2.98; N,9.19; Cl,11.63; S,10.52. Found. (%):C,55.07; H,3.02; N,9.09; Cl,11.39; S,10.64. NMR ($d_6$-DMSO) δ: 7.18 (1H, s), 7.29 (1H, dd, J=8.7 Hz, 2.1 Hz), 7.54 (1H, d, J=8.7 Hz), 8.13 (2H, m), 8.17 (1H, d, J=2.1 Hz), 8.76 (1H, s), 12.3 (1H, brs).

EXAMPLE 120

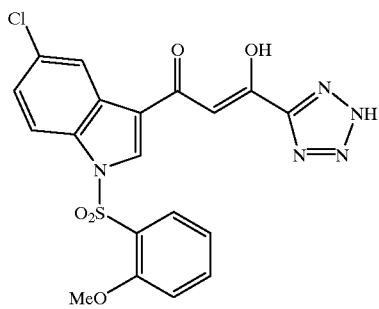

m.p.: 239° C. (decomposition) Recrystallized from MeOH Elemental Analysis for $C_{19}H_{14}ClN_5O_5S$ 0.4$CH_4O$ 0.5$H_2O$ Calcd. (%):C,48.37; H,3.47; N,14.54; Cl,7.36; S,6.66. Found. (%):C,48.15; H,3.26; N,14.74; Cl,7.42; S,6.92. NMR ($d_6$-DMSO) δ: 3.73 (3H, m), 7.20–7.49 (3H, m), 7.63 (1H, s), 7.69–7.81 (2H, m), 8.15–8.28 (2H, m), 9.27 (1H, s).

EXAMPLE 121

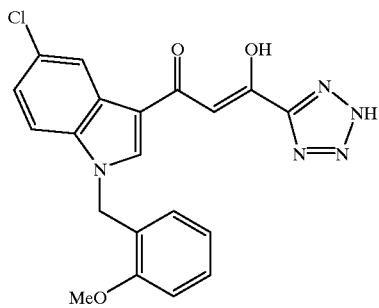

m.p.: 256° C. (decomposition) Recrystallized from EtOAc Elemental Analysis for $C_{20}H_{16}ClN_5O_3$ 0.3$H_2O$ Calcd. (%):C,57.85; H,4.03; N,16.87; Cl,8.54. Found. (%):C,57.85; H,4.16; N,17.02; Cl,8.25. NMR ($d_6$-DMSO) δ: 3.85 (3H, s), 5.49 (2H, s), 6.87–7.36 (6H, m), 7.69 (1H, d, J=8.8 Hz), 8.21 (1H, d, J=2.0 Hz), 8.95(1H, s).

EXAMPLE 122

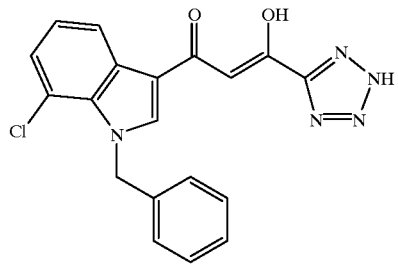

m.p.: 252° C. (decomposition) Recrystallized from EtOAc Elemental Analysis for $C_{19}H_{14}ClN_5O_2$ 0.1$C_4H_8O_2$ Calcd. (%):C,59.96; H,3.84; N,18.02; Cl,9.12. Found. (%):C,59.64; H,3.75; N,18.07; Cl,8.99. NMR ($d_6$-DMSO) δ: 5.89 (2H, s), 7.09–7.35 (7H, m), 8.29–8.33 (1H, m), 9.12 (1H, s).

EXAMPLE 123

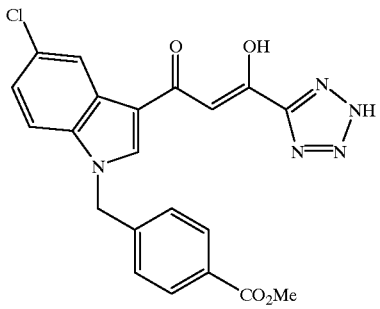

m.p.: 244–245° C. Recrystallized from EtOAc Elemental Analysis for $C_{21}H_{16}ClN_5O_4$ Calcd. (%):C,57.61; H,3.68; N,16.00; Cl,8.10. Found. (%):C,57.34; H,3.71; N,15.80; Cl,7.94. NMR ($d_6$-DMSO) δ: 3.83 (3H, s), 5.67 (2H, S), 7.24 (1H, s), 7.34 (1H, dd, J=8.7 Hz, 2.1 Hz), 7.46 (2H, d, J=8.1 Hz), 7.65 (1H, d, J=8.7 Hz), 7.94 (2H, d, J=8.1 Hz), 8.23(1H, d, J=2.1 Hz), 9.12 (1H, s).

EXAMPLE 124

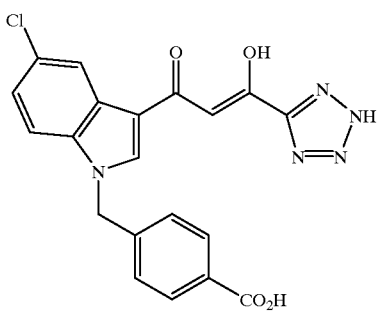

m.p.: 282–284° C. Recrystallized from EtOAc Elemental Analysis for $C_{20}H_{14}ClN_5O_4$ 0.3$C_4H_8O_2$ 0.3$H_2O$ Calcd. (%):C,55.87; H,3.81; N,15.22; Cl,7.71. Found. (%):C,55.87; H,3.56; N,14.89; Cl,8.09. NMR ($d_6$-DMSO) δ: 5.60 (2H, S), 7.25 (1H, dd, J=9.3 Hz, 2.1 Hz), 7.36 (2H, d, J=8.4 Hz), 7.54 (1H, d, J=8.7 Hz), 7.90 (2H, d, J=8.4 Hz), 7.86–7.92 (1H, m), 8.64 (1H, s).

EXAMPLE 125

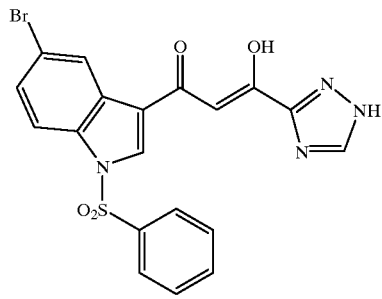

m.p.: 290–295° C. (decomposition) Recrystallized from EtOAc. Elemental Analysis for $C_{19}H_{13}BrN_4O_4S$ Calcd. (%):C,48.22; H,2.77; N,11.96; Br,16.88; S,6.77. Found. (%):C,48.39; H,3.04; N,11.96; Br,16.75; S,6.84. NMR($d_6$-DMSO) δ:7.35(1H, s), 7.60–7.83(4H, m), 7.99(1H, d, J=9.0 Hz), 8.22–8.25(2H, m), 8.42(1H, d, J=2.1 Hz), 8.75(1H, brs), 9.20(1H, s).

EXAMPLE 126

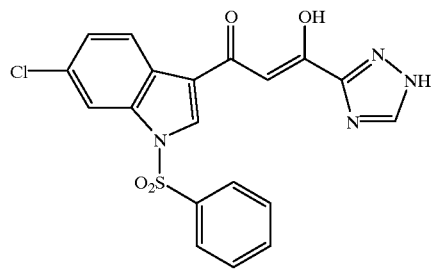

m.p.: 265–270° C. Recrystallized from EtOAc-THF Elemental Analysis for $C_{19}H_{13}ClN_4O_4S$ Calcd. (%):C, 53.21; H,3.06; N,13.06; Cl,8.27; S,748. Found. (%):C, 53.25; H,3.24; N,13.07; Cl,8.07; S,7.43. NMR($d_6$-DMSO) δ:7.35(1H, s), 7.46–8.29(8H, m), 8.80(1H, brs), 9.19(1H, s).

EXAMPLE 127

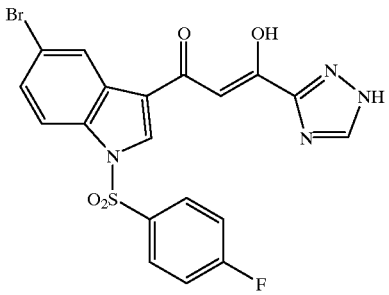

m.p.: 266–270° C. Recrystallized from EtOAc. Elemental Analysis for $C_{19}H_{12}BrFN_4O_4S$ Calcd. (%):C,46.45; H,2.46; N,11.40; Br,16.26; F,3.87; S,6.53. Found. (%):C,46.36; H,2.59; N,11.50; Br,16.45; F,3.86; S,6.55. NMR ($d_6$-DMSO) δ:7.34(1H, s), 7.49–7.65(3H, m), 8.01(1H, d, J=9.2 Hz), 8.32–8.44(3H, m), 8.55(1H, brs), 9.19(1H, s).

EXAMPLE 128

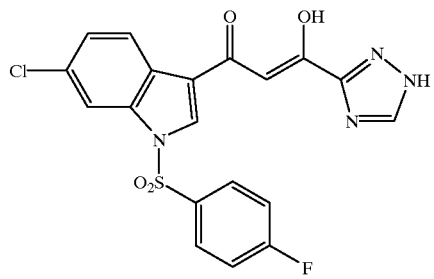

m.p.: 293–298° C. (decomposition) Recrystallized from THF. Elemental Analysis for $C_{19}H_{12}ClFN_4O_4S$ Calcd. (%):C,51.07; H,2.71; N,12.54; Cl,7.93; F,4.25; S,7.18. Found. (%):C,51.03; H,2.82; N,12.67; Cl,7.81; F,4.30; S,7.11. NMR($d_6$-DMSO) δ:7.34(1H, s), 7.47–7.57(3H, m), 8.04(1H, d, J=1.5 Hz), 8.27(1H, d, J=8.4 Hz), 8.38–8.43(2H, m), 8.74(1H, brs), 9.18(1H, s).

EXAMPLE 129

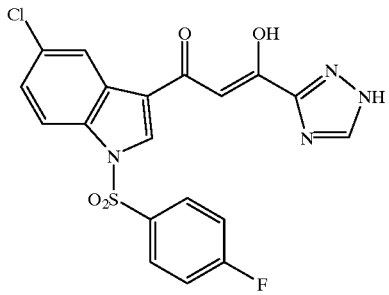

m.p.: 262–263° C. Recrystallized from EtOAc. Elemental Analysis for $C_{19}H_{12}ClFN_4O_4S$ $0.4H_2O$ Calcd. (%):C,50.26; H,2.84; N,12.34; Cl,7.81; F,4.18; S,7.06. Found. (%):C, 49.98; H,2.65; N,12.07; Cl,8.04; F,4.12; S,7.38. NMR($d_6$-DMSO) δ:7.35(1H, s), 7.50–7.56(3H, m), 8.06(1H, d, J=9.0 Hz), 8.27–8.38(3H, m), 8.83(1H, s), 9.20(1H, s), 14.7(1H, s).

EXAMPLE 130

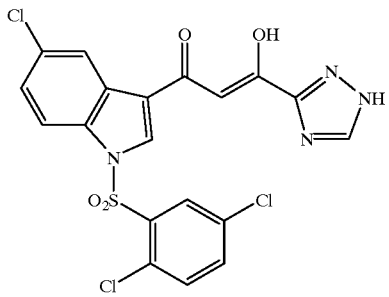

m.p.301–302° C. Recrystallized from EtOAc. Elemental Analysis (or $C_{19}H_{11}Cl_3N_4O_4S$ Calcd. (%):C,45.85; H,2.23; N,11.26; Cl,21.37; S,6.44. Found. (%):C,46.05; H,2.30; N,11.13; Cl,21.06; S,6.41. NMR($d_6$-DMSO) δ:7.31(1H, brs), 7.45–7.50(1H, m), 7.75(1H, d, J=8.7 Hz), 7.80–7.95 (2H, m), 8.32(1H, d, J=2.4 Hz), 8.52(1H, d, J=2.4 Hz), 9.12(1H, s), 9.21(1H, brs).

EXAMPLE 131

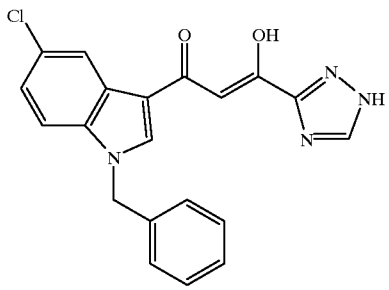

m.p.: 264–265° C. Recrystallized from EtOAc. Elemental Analysis for $C_{20}H_{15}ClN_4O_2$ Calcd. (%): C,63.41; H,3.99; N,14.79; Cl,9.36. Found. (%): C,63.52; H,4.17; N,14.48; Cl,9.15. NMR($d_6$-DMSO) δ:5.55(2H, s), 7.09(1H, s), 7.26–7.36(6H, m), 7.65(1H, d, J=8.7 Hz), 8.23(1H, d, J=2.1 Hz), 8.63(1H, brs), 8.98(1H, s).

EXAMPLE 132

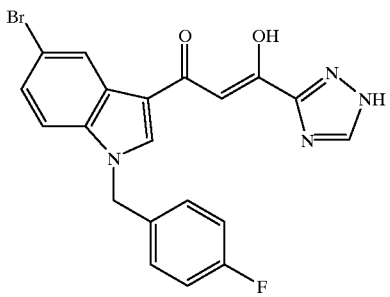

m.p.: 265–268° C. Recrystallized from EtOAc. Elemental Analysis for $C_{20}H_{14}BrFN_4O_2$ 2.3$H_2O$ Calcd. (%): C,49.77; H,3.88; N,11.61; Br,16.55; F,3.94. Found. (%): C,49.64; H,3.76; N,11.70; Br,16.73; F,4.02. NMR($d_6$-DMSO) δ:5.54 (2H, s), 7.09(1H, s), 7.18(2H, t, J=9.0 Hz), 7.40–7.47(3H, m), 7.64(1H, d, J=8.7 Hz), 8.39(1H, d, J=2.1 Hz), 8.64(1H, s), 8.97(1H, s).

EXAMPLE 133

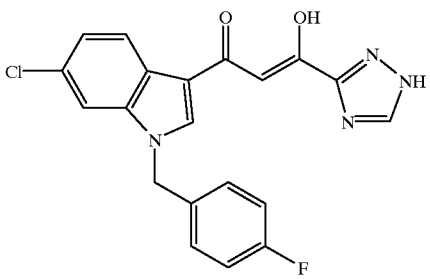

m.p.: 260–263° C. Recrystallized from EtOAc-dioxane. Elemental Analysis for $C_{20}H_{14}ClFN_4O_2$ Calcd. (%): C,60.54; H,3.56; N,14.12; Cl,8.93; F,4.79. Found. (%): C,60.39; H,3.61; N,14.25; Cl,8.87; F,4.80. NMR($d_6$-DMSO) δ:5.54(2H, s), 7.10(1H, s), 7.16–7.26(2H, m), 7.30(1H, dd, J=8.7 Hz, 1.8 Hz), 7.43–7.50(2H, m), 7.82(1H, d, J=1.8 Hz), 8.22(1H, d, J=8.7 Hz), 8.64(1H, s), 8.95(1H, s).

EXAMPLE 134

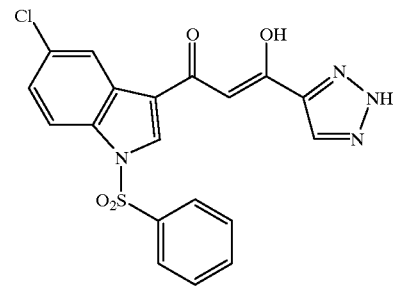

m.p.: 236–239° C. Recrystallized from EtOAc. Elemental Analysis for $C_{19}H_{13}ClN_4O_4S$ 0.25$C_4H_8O_2$ Calcd. (%) : C,53.28; H,3.35; N,12.43; Cl,7.86; S,7.11. Found. (%): C,53.43; H,3.43; N,12.23; Cl,8.00; S,7.38. NMR($d_6$-DMSO) δ:7.33(1H, s), 7.51(1H, dd, J=9.0 Hz, 2.4 Hz), 7.65–7.71(2H, m), 7.76–7.81(1H, m), 8.04(1H, d, J=9.0 Hz), 8.18–8.21(2H, m), 8.25(1H, d, J=2.4 Hz), 8.66(1H, brs), 9.19(1H, s).

EXAMPLE 135

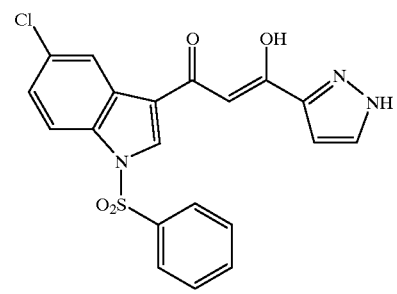

m.p.: 219–212° C. Recrystallized from EtOAc-$Et_2O$. Elemental Analysis (for $C_{20}H_{14}ClN_3O_4S$ 0.2$C_4H_8O_2$ 0.2$H_2O$) Calcd. (%): C,55.63; H,3.59; N,9.36; Cl,7.89; S,7.14. Found. (%): C,55.62; H,3.37; N,9.25; Cl,7.88; S,7.22. NMR($d_6$-DMSO) δ:6.95(1H, s), 7.22(1H, s), 7.49 (1H, dd, J=9.0 Hz, 2.1 Hz), 7.65–7.70(2H, m), 7.76–7.82 (1H, m), 7.93–8.05(2H, m), 8.12–8.25(3H, m), 9.13(1H, s), 13.6(1H, brs).

EXAMPLE 136

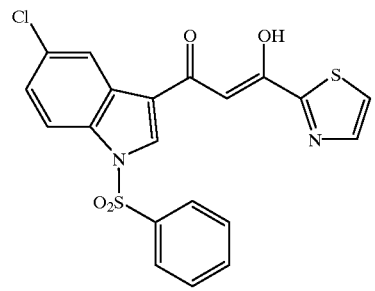

m.p.:191–194° C. Recrystallized from MeOH Elemental Analysis for $C_{20}H_{13}ClN_2O_4S_2$ Calcd. (%):C,53.99; H,2.95; N,6.30; Cl,7.97; S, 14.41. Found. (%):C,50.89; H,2.80; N,6.39; Cl,7.51; S,14.24. NMR($d_6$-DMSO) δ:7.15(1H, s), 7.40(1H, dd, J=8.7 Hz, 2.1 Hz), 7.51–7.56(2H, m), 7.63–7.68(1H, m), 7.86(1H, d, J=3.3 Hz), 7.95(1H, d, J=8.7 Hz), 8.00–8.04(2H, m), 8.25(1H, d, J=3.3 Hz), 8.29(1H, d, J=2.1 Hz), 8.51(1H, s).

EXPERIMENTAL EXAMPLE

The inhibitory effects of the compounds of the present invention for HIV-1 integrase have been determined by the assay described below.

(1) Preparation of DNA solutions.

Substrate DNA and target DNA, which sequences were indicated below, were synthesized by Amersham Pharmacia Biotech and dissolved in KTE buffer (composition: 100 mM KCl, 1 mM EDTA, 10 mM Tris-HCl (pH 7.6)) at concentration of 2 pmol/μl and 5 pmol/μ, respectively. The DNA solutions were annealed with each complement by slowly cooling after heating.

```
(Substrate DNA)
5'-Biotin-ACC CTT TTA GTC AGT GTG GAA AAT CTC TAG CAG T-3'
3'-          GAA AAT CAG TCA CAC CTT TTA GAG ATC GTC A-5'

(Target DNA)
5'-          TGA CCA AGG GCT AAT TCA CT-Dig-3'
3'-Dig-      ACT GGT TCC CGA TTA AGT GA    -5'
```

(2) Calculations of the percent inhibitions (the IC$_{50}$ values of test compounds)

Streptavidin, obtained from Vector Laboratories, was dissolved in 0.1 M carbonate buffer (composition: 90 mM Na$_2$CO$_3$, 10 mM NaHCO$_3$) at concentration of 40 μg/ml. After coating each well of microtiter plates (obtained from NUNC) with 50 μl of the above solution at 4° C. over night, each well was washed twice with PBS (composition: 13.7 mM NaCl, 0.27 mM KCl, 0.43 mM Na$_2$HPO$_4$, 0.14 mM KH$_2$PO$_4$) and blocked with 300 μl of 1% skim milk in PBS for 30 min. Additionally, each well was washed twice with PBS and added 50 μl of substrate DNA solution (2 pmol/μl). The microtiter plates were kept at room temperature for 30 min. Then, each well was washed twice with PBS and once with H$_2$O.

Subsequently, in the each well prepared above were added 45 μl of the reaction buffer prepared from 12 μl of the buffer (composition: 150 mM MOPS (pH 7.2), 75 mM MnCl$_2$, 50 mM 2-mercaptoethanol, 25% glycerol, 500 μg/ml bovine serum albumin-fraction V), 1 μl of target DNA, and 32 μl of the distilled water. Additionally, 6 μl of either a test compound in DMSO or DMSO for positive control(PC) was mixed with the above reaction buffer, then 9 μl of integrase solution (30 pmol) was added and mixed well. In the well of negative control (NC) was added 9 μl of integrase dilution buffer (composition: 20 mM MOPS (pH7.2), 400 mM potassium glutamete, 1 mM EDTA, 0.1% NP-40, 20% glycerol, 1 mM DTT, 4M urea).

The microtiter plates were incubated at 30° C. for 1 hour. After incubation, the reaction solution was removed and each well was washed twice with PBS. Subsequently, each well of the microtiter plates was filled with 100 μl of anti-digoxigenin antibody labeled with alkaline phosphatase (Lamb Fab fragment: obtained from Boehringer) and incubated at 30° C. for 1 hour. Then, each well was washed twice with 0.05% Tween20 in PBS and once with PBS. Next, 150 μl of the Alkaline phosphatase reaction buffer (composition: 10 mM p-Nitrophenylphosphate (obtained from Vector Laboratories), 5 mM MgCl$_2$, 100 mM NaCl, 100 mM Tris-HCl (pH 9.5))was added in each well. The microtiter plates were incubated at 30° C. for 2 hours and the reaction was terminated by the addition of 50 μl of 1 N NaOH solution. The optical density (OD) at 405 nm of each well was measured and the percent inhibition was determined by the following expression.

The percent inhibition (%)=100[1-{(C abs.-NC abs.)/(PC abs.-NC abs.)}]

C abs.; the OD of the well of the compounds

NC abs.: the OD of the negative control (NC)

PC abs.: the OD of the positive control (PC)

The IC$_{50}$ values, the concentration of the compounds at percent inhibition 50%, are shown below.

TABLE 9

| No. of examples | IC$_{50}$ (μg/ml) |
|---|---|
| 1(2) | 0.31 |
| 23(2) | 0.13 |
| 67(2) | 0.55 |
| 71 | 1.49 |
| 72 | 0.48 |
| 80 | 3.30 |
| 81 | 3.60 |

(Note)
For instance, "1(2 )" means the compound which was prepared at the process(2) of example 1.

What is claimed is:

1. A compound of the formula:

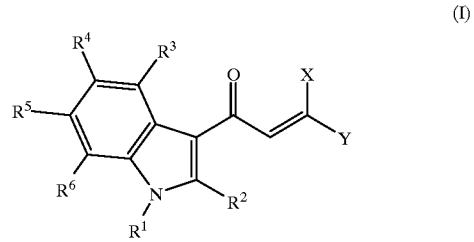

(I)

wherein

R$^1$ is hydrogen, lower alkyl, cycloalkyl lower alkyl, lower alkylsulfonyl, lower alkylcarbonyl, optionally substituted aryl, optionally substituted aralkyl, optionally substituted arylsulfonyl, optionally substituted arylcarbonyl, optionally substituted heteroaryl, optionally substituted heteroaralkyl, optionally substituted heteroarylsulfonyl, lower alkoxy carbonyl, optionally substituted sulfamoyl, or optionally substituted carbamoyl;

R² is hydrogen, lower alkyl, lower alkylcarbonyl, optionally substituted aryl, optionally substituted aralkyl, optionally substituted arylcarbonyl, optionally substituted heteroaryl, optionally substituted heteroaralkyl, optionally substituted arylthio, optionally substituted arylsulfinyl, optionally substituted arylsulfonyl, optionally substituted heterocyclyl lower alkyl, or optionally substituted heterocyclyl sulfonyl;

R³, R⁴, R⁵, and R⁶ each is independently hydrogen, halogen, trihalogenated lower alkyl, hydroxy, lower alkoxy, nitro, amino, optionally esterified carboxy, optionally substituted aralkyloxy, or optionally substituted arylsulfonyloxy;

X is hydroxy or optionally substituted amino;

Y is optionally substituted aryl or optionally substituted heteroaryl, a tautomer, or pharmaceutically acceptable salt, or a hydrate thereof.

2. The compound according to claim 1 wherein R¹ is hydrogen or optionally substituted arylsulfonyl.

3. The compound according to claim 1 wherein R² is hydrogen, optionally substituted aryl, or optionally substituted aralkyl.

4. The compound according to claim 1 wherein R³, R⁴, R⁵, and R⁶ each is independently hydrogen or halogen.

5. The compound according to claim 4 wherein R³, R⁵, and R⁶ are all hydrogens.

6. The compound according to claim 1 wherein X is hydroxy.

7. The compound according to claim 1 wherein Y is optionally substituted heteroaryl.

8. The compound according to claim 7 wherein said heteroaryl is a 5- or 6-membered ring containing at least one nitrogen atom.

9. The compound according to claim 8 wherein said heteroaryl is tetrazolyl, triazolyl, or imidazolyl.

10. The compound according to claim 1 wherein R¹ is hydrogen or optionally substituted arylsulfonyl; R² is hydrogen, optionally substituted aryl, or optionally substituted aralkyl; R³, R⁴, R⁵, and R⁶ each is independently hydrogen or halogen; X is hydroxy.

11. The compound according to claim 1 wherein R¹ is hydrogen or optionally substituted arylsulfonyl; R² is hydrogen, optionally substituted aryl, or optionally substituted aralkyl; R³, R⁴, R⁵, and R⁶ each is independently hydrogen or halogen; X is hydroxy; Y is optionally substituted heteroaryl.

12. The compound according to claim 11 wherein R¹ is hydrogen or phenylsulfonyl optionally substituted with halogen; R² is hydrogen, phenyl optionally substituted with halogen, or phenylmethyl optionally substituted with halogen; R⁴ is halogen; R³, R⁵, and R⁶ are all hydrogens at the same time; X is hydroxy; Y is tetrazolyl.

13. A pharmaceutical composition containing the compound according to any one of claims 1–12 as an active ingredient and a carrier.

14. A composition for inhibiting integrase which contains the compound according to any one of claims 1–12.

15. An antiviral composition which contains the compound according to any one of claims 1–12.

16. An anti-HIV composition which contains the compound according to any one of claims 1–12.

* * * * *